(12) United States Patent
Westenskow et al.

(10) Patent No.: US 7,693,697 B2
(45) Date of Patent: Apr. 6, 2010

(54) ANESTHESIA DRUG MONITOR

(75) Inventors: Dwayne Westenskow, Salt Lake City, UT (US); James Agutter, Salt Lake City, UT (US); Noah Syroid, Salt Lake City, UT (US); David Strayer, Salt Lake City, UT (US); Robert Albert, Salt Lake City, UT (US); Frank Drews, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1098 days.

(21) Appl. No.: 10/269,422

(22) Filed: Oct. 11, 2002

(65) Prior Publication Data

US 2003/0156143 A1 Aug. 21, 2003

Related U.S. Application Data

(63) Continuation-in-part of application No. 09/457,068, filed on Dec. 7, 1999, now abandoned.

(60) Provisional application No. 60/328,878, filed on Oct. 12, 2001.

(51) Int. Cl.
*G06G 7/58* (2006.01)
*G06G 7/48* (2006.01)
(52) U.S. Cl. .......................................... 703/11; 703/12
(58) Field of Classification Search ................... 703/11, 703/12
See application file for complete search history.

(56) References Cited

U.S. PATENT DOCUMENTS

| 4,671,953 | A | 6/1987 | Stanley et al. | |
| 4,752,893 | A | 6/1988 | Guttag et al. | 345/133 |
| 4,772,882 | A | 9/1988 | Mical | 345/146 |
| 4,813,013 | A | 3/1989 | Dunn | 395/159 |
| 4,823,283 | A | 4/1989 | Diehm et al. | 345/352 |
| 4,885,173 | A | 12/1989 | Stanley et al. | |
| 4,915,757 | A | 4/1990 | Rando | 156/64 |
| 4,926,868 | A | 5/1990 | Larsen | |
| 5,021,976 | A | 6/1991 | Wexelblat et al. | 345/356 |
| 5,088,981 | A | 2/1992 | Howson et al. | |
| 5,121,469 | A | 6/1992 | Richards et al. | 345/429 |

(Continued)

OTHER PUBLICATIONS

Frenkel et al. "Pharmacokinetics and pharmacodynamics of propofol/alfentanil infusions for sedation in ICU patients" 1995 Intensive Care Med.*

(Continued)

*Primary Examiner*—Kamini Shah
*Assistant Examiner*—Saif Alhija
(74) *Attorney, Agent, or Firm*—Thorpe North & Western LLP

(57) ABSTRACT

A method, system and apparatus for the monitoring, diagnosis and evaluation of the state of a dynamic drug display system is disclosed. This invention provides for the rapid cognitive grasp of the overall state of drug combination effects with respect to a dynamic system. The system provides for displayed objects, which change in real-time to show the changes of the functions of the system. In particular, this invention is directed to the processing and display of drug data for the use of doctors in the process of monitoring or administering drugs to patients.

27 Claims, 45 Drawing Sheets

U.S. PATENT DOCUMENTS

| | | | |
|---|---|---|---|
| 5,262,944 A | 11/1993 | Weisner et al. | 600/300 |
| 5,317,321 A | 5/1994 | Sass | 342/176 |
| 5,484,602 A | 1/1996 | Stanley et al. | |
| 5,485,850 A | 1/1996 | Dietz | |
| 5,491,779 A | 2/1996 | Bezjian | 395/140 |
| 5,515,301 A | 5/1996 | Corby, Jr. et al. | 364/578 |
| 5,522,798 A * | 6/1996 | Johnson et al. | 604/65 |
| 5,588,104 A | 12/1996 | Lanier et al. | 395/326 |
| 5,592,195 A | 1/1997 | Misono et al. | 345/146 |
| 5,596,694 A | 1/1997 | Capps | 395/152 |
| 5,651,775 A | 7/1997 | Walker et al. | |
| 5,680,590 A | 10/1997 | Parti | |
| 5,751,931 A | 5/1998 | Cox et al. | 395/140 |
| 5,768,552 A | 6/1998 | Jacoby | 395/334 |
| 5,774,878 A | 6/1998 | Marshall | 705/35 |
| 5,796,398 A | 8/1998 | Zimmer | 345/339 |
| 5,812,134 A | 9/1998 | Pooser et al. | 345/356 |
| 5,812,688 A | 9/1998 | Gibson | 381/119 |
| 5,830,150 A | 11/1998 | Palmer et al. | 600/523 |
| 5,873,731 A | 2/1999 | Prendergast | |
| 5,875,108 A | 2/1999 | Hoffberg et al. | |
| 5,901,246 A | 5/1999 | Hoffberg et al. | |
| 5,923,330 A | 7/1999 | Tarlton et al. | 345/419 |
| 5,925,014 A | 7/1999 | Teeple Jr. | |
| 5,957,860 A | 9/1999 | Rodiera | |
| 6,009,346 A | 12/1999 | Ostrow | |
| 6,042,548 A | 3/2000 | Giuffre | |
| 6,067,542 A | 5/2000 | Carino, Jr. | |
| 6,081,266 A | 6/2000 | Sciammarella | 345/341 |
| 6,184,876 B1 | 2/2001 | Miller | 345/302 |
| 6,222,547 B1 | 4/2001 | Schwuttke et al. | 345/419 |
| 6,289,299 B1 | 9/2001 | Daniel, Jr. et al. | |
| 6,542,858 B1 | 4/2003 | Grass et al. | |
| 6,647,358 B2 | 11/2003 | Grass et al. | |

OTHER PUBLICATIONS

Sheiner, "Learning Versus Confirming in Clinical Drug Development", Mar. 1997.*

Peck et al. "Opportunities for Integration of Pharmacokinetics, Pharmacodynamics, and Toxicokinetics in Rational Drug Development" vol. 9, No. 6, 1992.*

Shafer et al. "Algorithms to Rapidly Achieve and Maintain Stable Drug Concentrations at the Site of Drug Effect with a Computer-Controlled Infusion Pump", Journal of Pharmacokinetics and Biopharmaceutics, vol. 20, No. 2, 1992.* van Meurs et al., "Pharmacokinetic-pharmacodynamic model for educational simulations," IEEE Trans Biomed Eng. May 1998, 45(5): 582-90.

Glombitza et al., "Virtual Surgery in a (tele-)radiology Framework," IEEE Trans. Information Technology in Biomedicine. Sep. 1999, vol. 3, Issue 3, sections2-3.

Shafer et al., Algorithms to Rapidly Achieve and Maintain Stable Drug Concentrations at the Site of Drug Effect with a Computer Controlled Infusion Pump, Journal of Pharmokenetics and Biopharmaceutics, ol. 20m #2, 1992, 2 pages.

International Search Report, Apr. 18, 2002, 1 page.

International Search Report, Aug. 25, 2004, 2 pages.

http://www.google.com/search?hl=en&lr=&defl=en&q=define:Anesthesia&sa, Dec. 8, 2006, pp. 1-3.

* cited by examiner

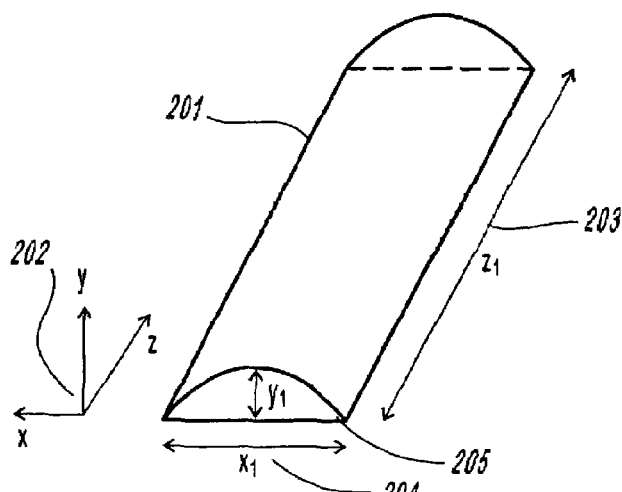

ENGINE
$x_1$ = ENGINE TEMPERATURE
$y_1$ = ENGINE RPM
$z_1$ = ENGINE EXHAUST
   GAS VOLUME

FIGURE 2a

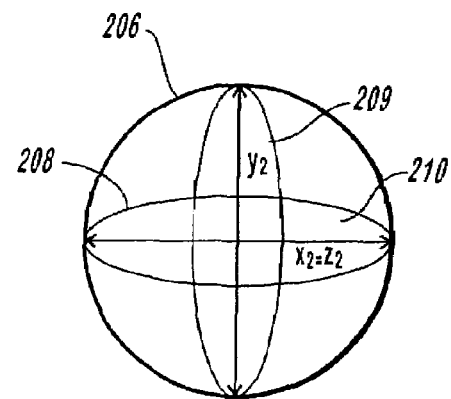

CARDIAC SYSTEM FUNCTION
$x_2 = z_2$ = HEART RATE / SECOND
$y_2$ = STROKE VOLUME

SPHERICAL VOLUME = CARDIAC OUTPUT

FIGURE 2b

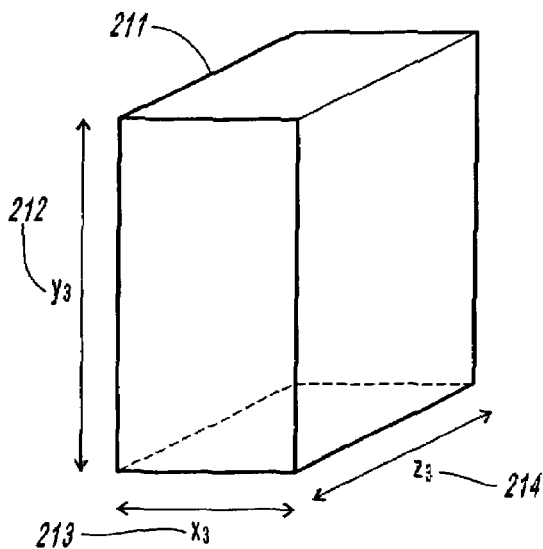

SALES DEPARTMENT OPERATION
$x_3$ = AVERAGE TIME / CONTRACT
$y_3$ = # OF CONTRACTS
$z_3$ = AVG. REVENUE/CONTRACT

FIGURE 2c

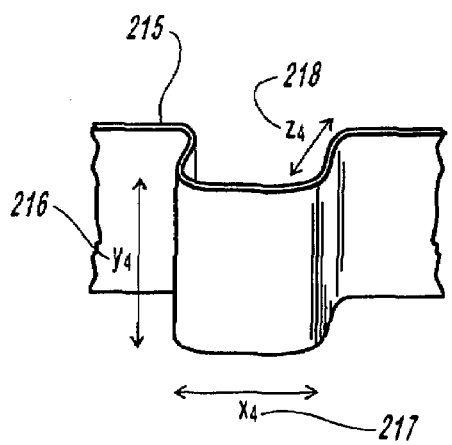

RESPIRATORY FUNCTION
$x_4$ = AVERAGE TIME / CONTRACT
$y_4$ = FCN OF xy AND RESP. VOLUME
$z_4$ = +/- INHALATION / EXHALATION

SLAB VOLUME = RESPIRATORY VOLUME

$O_x$ = 1/2 REP. SPACE
(H-PIC. SPACE)

$O_y$ = BLOOD PRESSURE
(UP-DOWN)

$O_z$ = OXYGEN CONCENTRATION
IN THE BLOOD
(BACK TO FRONT)

@△TN=>

$P_x$ = 1/2 REP. SPACE
(H-PIC. SPACE)

$P_y$ = SALES PROFIT
(UP-DOWN)

$P_z$ = PRODUCTS IN STOCK
(BACK TO FRONT)

| INTERFACE MODE I<br>(e.g. MEDICINE) | INTERFACE MODE II<br>(e.g. CORPORATE DASHBOARD) |
|---|---|
| GIVEN:<br>  - CRITICAL FUNCTIONS<br><br>(UNCHANGEABLE)<br>  - PHYSIOLOGIC DATA COLLECTED<br>  - SYMBOLIC SYSTEM STANDARD<br>  - REFERENTIAL FRAMEWORK<br>    IDEAL VALUES/ALARMS<br><br>(CHANGEABLE)<br>  - PARTICULAR VALUES<br>  - OBJECT ATTRIBUTES<br>1301 | GIVEN:<br>  - DEFAULT/GENERIC L-SPACE/H-SPACE<br><br>USER DETERMINES:<br>  - CRITICAL FUNCTIONS<br>  - VITAL SIGNS TO BE COLLECTED<br>  - SYMBOLIC SYSTEM TO BE USED<br>  - IDEAL VALUES/ALARMS<br>  - OBJECTS/ATTRIBUTES SPACE<br><br>1302 |

COMMON INTERFACE FEATURES
- L-SPACE
- H-SPACE
- ZOOM/SPEED
- VIEWPOINTS

FIGURE 13

ANESTHESIA DRUG MONITOR

CROSS REFERENCE TO RELATED APPLICATIONS

This patent application is a continuation-in-part patent application of U.S. patent application Ser. No. 09/457,068, which was filed on Dec. 7, 1999 now abandoned and of Provisional Patent Application Ser. No. 60/328,878, filed on Oct. 12, 2001. Priority is hereby claimed to all common material disclosed in these pending patent cases.

FEDERAL RESEARCH STATEMENT

Some of the technology described is this patent application was funded in part by National Instituted of Health grant number 1 R24 HL 64590.

BACKGROUND OF INVENTION

1. Field of the Invention

This invention relates to the visualization, perception, representation and computation of data relating to the attributes or conditions constituting the health state of a dynamic system. More specifically, this invention relates to the display and computation of anesthesia drug data, in which variables constituting attributes and conditions of a dynamic anesthesia system can be interrelated and visually correlated in time as three-dimensional objects.

2. Description of the Related Art

A variety of methods and systems for the visualization of data have been proposed. Traditionally, these methods and systems fail to present in a real-time multi-dimensional format that is directed to facilitating a user"s analysis of multiple variables and the relationships between such multiple variables. Moreover, such prior methods and systems tend not to be specifically directed to the monitoring of anesthesia or which is capable of estimating, predicting and displaying drug dosages, infusions, effect site concentration, and drug effects during anesthesia. Prior methods typically do not process and display data in real-time, rather they use databases or spatial organizations of historical data. Generally, they also simply plot existing information in two or three dimensions, but without using three-dimensional geometric objects to show the interrelations between data.

Often previous systems and methods are limited to pie charts, lines or bars to represent the data. Also, many previous systems are limited to particular applications or types of data. The flexibility and adaptability of the user interface and control is typically very limited, and may not provide flexible coordinate systems and historical-trend monitors. Other systems, which have a flexible user interface, generally require substantial user expertise in order to collect and evaluate the data, including the pre-identification of data ranges and resolution. Another common limitation of previous systems and methods is that they provide only a single or predetermined viewpoint from which to observe the data. Typically, prior systems and methods do not provide data normalcy frameworks to aid in the interpretation of the data. Furthermore, most prior methods use "icons," shapes, lines, bars, or graphs.

Currently, many anesthesiologists must remember the drugs and doses that they have administered unless they have transcribed the information to a paper anesthetic record. Anesthesiologists may also need to rely on their memory and experience to provide adequate anesthesia. Anesthesiologists currently assess the effect of the anesthetics on a patient by indirect methods: pupil diameter, consciousness, breath and heart sounds, reflex response, blood pressure and heart rate. Unfortunately, many of these signs appear only when a patient has not received enough of an anesthetic drug or has received an overdose of a drug.

For general background material, the reader is directed to U.S. Pat. Nos. 4,671,953, 4,752,893, 4,772,882, 4,813,013, 4,814,755, 4,823,283, 4,885,173, 4,915,757, 4,926,868, 5,021,976, 5,121,469, 5,262,944, 5,317,321, 5,484,602, 5,485,850, 5,491,779, 5,588,104, 5,592,195, 5,596,694, 5,651,775, 5,680,590, 5,751,931, 5,768,552, 5,774,878, 5,796,398, 5,812,134, 5,830,150, 5,873,731, 5,875,108, 5,901,246, 5,923,330, 5,925,014, 5,957,860, and 6,042,548 each of which is hereby incorporated by reference in its entirety for the material disclosed therein.

As this disclosure employs a number of terms, which may be new to the reader, the reader is directed to the applicants" definitions section, which is provided at the beginning of the detailed description section.

SUMMARY OF INVENTION

It is desirable to provide a method, system, and apparatus, which facilitates the rapid and accurate analysis of complex and quickly changing anesthesia drug data. Moreover, it is desirable that such a system and method be capable of estimating, predicting and displaying drug dosages, infusions, effect site concentrations and drug effects during anesthesia. It is desirable that such a system and method be capable of analyzing time based, real-time, and historical data and that it be able to graphically show the relationships between various data.

Research studies have indicated that the human mind is better able to analyze and use complex data when it is presented in a graphic, real world type representation, rather than when it is presented in textual or numeric formats. Research in thinking, imagination and learning has shown that visualization plays an intuitive and essential role in assisting a user associate, correlate, manipulate and use information. The more complex the relationship between information, the more critically important is the communication, including audio and visualization of the data. Modern human factors theory suggests that effective data representation requires the presentation of information in a manner that is consistent with the perceptual, cognitive, and response-based mental representations of the user. For example, the application of perceptual grouping (using color, similarity, connectedness, motion, sound etc.) can facilitate the presentation of information that should be grouped together. Conversely, a failure to use perceptual principles in the appropriate ways can lead to erroneous analysis of information.

The manner in which information is presented also affects the speed and accuracy of higher-level cognitive operations. For example, research on the "symbolic distance effect" suggests that there is a relationship between the nature of the cognitive decisions (for example, is the data increasing or decreasing in magnitude?) and the way the information is presented (for example, do the critical indices become larger or smaller, or does the sound volume or pitch rise or fall?). Additionally, "population stereotypes" suggest that there are ways to present information that are compatible with well-learned interactions with other systems (for example, an upwards movement indicates an increasing value, while a downwards movement indicates a decreasing value).

Where there is compatibility between the information presented to the user and the cognitive representations presented to the user, performance is often more rapid, accurate, and consistent. Therefore, it is desirable that information be presented to the user in a manner that improves the user's ability to process the information and minimizes any mental transformations that must be applied to the data.

Therefore, it is the general object of this invention to provide a method and systems for presenting a three-dimensional visual and/or possibly an audio display technique that assists in the monitoring and evaluation of drug data.

It is a further object of this invention to provide a method and system that assists in the evaluation of drug data with respect to the classification of an anesthetic.

It is another object of this invention to provide a method and system that assists in the evaluation of drug data with respect to anesthetics, including sedatives, analgesics, and neuromuscular blocking agents.

It is a still further object of this invention to provide a method and system that assists in the display of drug effects during anesthesia that takes into account the patient''s age, gender, height and weight as related to historical or normative values.

Another object of this invention is to provide a method and system that assists in the evaluation of drug effects during anesthesia that provides for system execution faster than real time.

A still further object of this invention is to provide a method and system, which provides the gathering and use of sensor measured data, as well as the formatting and normalization of the data in a format suitable to the processing methodology.

A further object of this invention is to provide a method and system, which can normalize drug concentration and can display the concentration relative to the time that it was administered.

Another object of this invention is to provide a method and system, which provides a three-dimensional graphic display for the use of doctors in an operating room.

It is another object of this invention to provide a method and system, which provides three-dimensional graphic display that is used in conjunction with automatic drug delivery systems.

It is an object of this invention to provide a method and system that provides a visual display record of the drugs administered and a current, past and predicted estimate of how the drug should be expected to affect the patient.

It is a further object of this invention to provide a method and system that permits an integrated and overall holistic understanding of the effects of drugs during anesthesia.

A further object of this invention is to provide a method and system where three-dimensional objects are built from three-dimensional object primitives, including: cubes, spheres, pyramids, n-polygon prisms, cylinders, slabs.

A still further object of this invention is to provide a method and system, wherein three-dimensional objects are placed within health-space based on the coordinates of their geometric centers, edges, vertices, or other definite geometric variables.

It is a further object of this invention to provide a method and system, which has three-dimensional objects that have three spatial dimensions, as well as geometric, aesthetic and aural attributes, to permit the mapping of multiple data functions.

It is another object of this invention to provide a method and system, which shows increases and decreases in data values using changes in location, size, form, texture, opacity, color, sound and the relationships thereof in their context.

It is a still further object of this invention to provide a method and system, wherein the particular three-dimensional configuration of three-dimensional objects can be associated with a particular time and health state.

A still further object of this invention is to provide a method and system that permits the simultaneous display of the history of data objects.

Another object of this invention is to provide a method and system that provides for the selection of various user selectable viewports.

It is a further object of this invention to provide a method and system that provides both a global and a local three-dimensional coordinate space.

It is another object of this invention to provide a method and system that permits the use of time as one of the coordinates.

It is a still further object of this invention to provide a method and system that provides a reference framework of normative values for direct comparison with the measured data.

It is a further object of this invention to provide a method and system where normative values are based on the average historical behavior of a wide population of healthy systems similar to the system whose health is being monitored.

A further object of this invention is to provide a method and system that provides viewpoints that can be selected to be perspective views, immersive Virtual Reality views, or any orthographic views.

Another object of this invention is to provide a method and system that permits the display of a layout of multiple time-space viewpoints.

A still further object of this invention is to provide a method and system that provides for zooming in and out of a time and/or space coordinate.

It is another object of this invention to provide a method and system that permits temporal and three-dimensional modeling of data "health" states based on either pre-recorded data or real-time data, that is as the data is obtained.

Another object of this invention is to provide a method and system that presents the data in familiar shapes, colors, and locations to enhance the usability of the data.

A still further object of the invention is to provide a method and system that uses animation, and sound to enhance the usefulness of the data to the user.

It is an object of this invention to provide a method and system for the measurement, computation, display and user interaction, of complex data sets that can be communicated and processed at various locations physically remote from each other, over a communication network, as necessary for the efficient utilization of the data and which can be dynamically changed or relocated as necessary.

It is still a further object of this invention to provide a method and system for the display of data that provides both a standard and a customized interface mode, thereby providing user and application flexibility.

It is an object of this invention to provide and method and system for the estimation, prediction, and display of drug dosages, infusions, effect site concentrations, and drug effects of intravenous drugs during anesthesia using pharmacokinetic and pharmacodynamic models.

It is still a further object of this invention to provide a method and system for data representation in real time.

Another object of this invention is to provide a method and system for displaying the interaction effects of multiple medications in an intuitive easy to understand format.

These and other objects of this invention are achieved by the method and system herein described and are readily apparent to those of ordinary skill in the art upon careful review of the following drawings, detailed description and claims.

BRIEF DESCRIPTION OF DRAWINGS

In order to show the manner that the above recited and other advantages and objects of the invention are obtained, a more particular description of the preferred embodiment of the invention, which is illustrated in the appended drawings, is described as follows. The reader should understand that the drawings depict only a preferred embodiment of the invention, and are not to be considered as limiting in scope. A brief description of the drawings is as follows:

FIGS. 2a, 2b, 2c, and 2d are representative 3-D objects representing critical functions.

FIG. 13 shows the interface modes of the preferred embodiment of this invention.

Figure 1A:
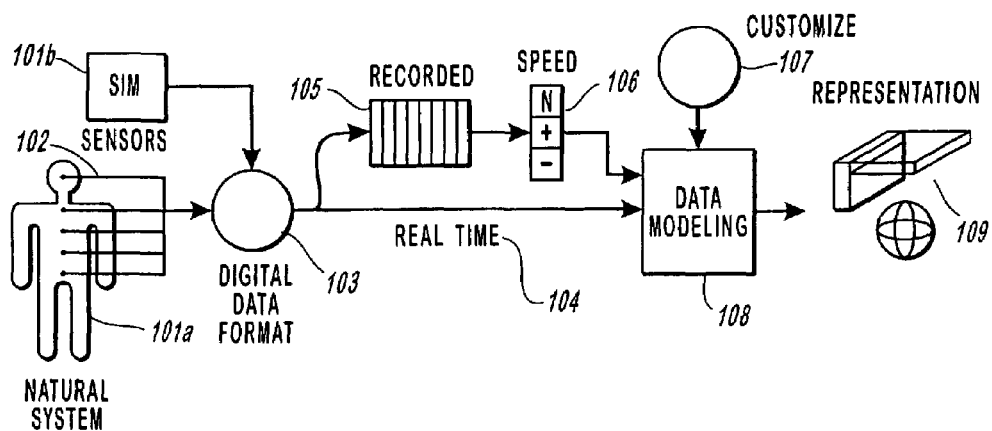
FIG. 1a is a top-level representative diagram showing the data processing paths of the preferred embodiment of this invention.

Reference is now made in detail to the present preferred embodiments of the invention, examples of which are illustrated in the accompanying drawings.

DETAILED DESCRIPTION

This invention is a method, system and apparatus for the visual display of complex sets of dynamic data. In particular, this invention provides the means for efficiently analyzing, comparing and contrasting data, originating from either natural or artificial systems. This invention provides n-dimensional visual representations of data through innovative use of orthogonal views, form, space, frameworks, color, shading, texture, transparency, sound and visual positioning of the data. The preferred system of this invention includes one or a plurality of networked computer processing and display systems, which provide real-time as well as historical data, and which processes and formats the data into an audio-visual format with a visual combination of objects and models with which the user can interact to enhance the usefulness of the processed data. While this invention is applicable to a wide variety of data analysis applications, one important application is the analysis of health data. For this reason, the example of a medical application for this invention is used throughout this description. The use of this example is not intended to limit the scope of this invention to medical data analysis applications only, rather it is provided to give a context to the wide range of potential application for this invention.

This invention requires its own lexicon. For the purposes of this patent description and claims, the inventors intend that the following terms be understood to have the following definitions.

An "artificial system" is an entity, process, combination of human designed parts, and/or environment that is created, designed or constructed by human intention. Examples of artificial systems include manmade real or virtual processes, computer systems, electrical power systems, utility and construction systems, chemical processes and designed combinations, economic processes (including, financial transactions), agricultural processes, machines, and human designed organic entities.

A "natural system" is a functioning entity whose origin, processes and structures were not manmade or artificially created. Examples of natural systems are living organisms, ecological systems and various Earth environments.

The "health" of a system is the state of being of the system as defined by its freedom from disease, ailment, failure or inefficiency. A diseased or ill state is a detrimental departure from normal functional conditions, as defined by the nature or specifications of the particular system (using historical and normative statistical values). The health of a functioning system refers to the soundness, wholeness, efficiency or well being of the entity. Moreover, the health of a system is determined by its functioning.

"Functions" are behaviors or operations that an entity performs. Functional fitness is measures by the interaction among a set of "vital-signs" normally taken or measured using methods well known in the art, from a system to establish the system's health state, typically at regular or defined time intervals.

"Health-space" or "H-space" is the data representation environment that is used to map the data in three or more dimensions.

"H-state" is a particular 3-D configuration or composition that the various 3-D objects take in H-space at a particular time. In other words, H-state is a 3-D snapshot of the system's health at one point of time.

"Life-space" or "L-space" provides the present and past health states of a system in a historical and comparative view of the evolution of the system in time. This 3-D representation environment constitutes the historical or Life-space of a dynamic system. L-space allows for both continuous and categorical displays of temporal dependent complex data. In other words, L-space represents the health history or trajectory of the system in time.

"Real-Time Representation" is the display of a representation of the data within a fraction of a second from the time when the event of the measured data occurred in the dynamic system.

"Real-Time User Interface" is the seemingly instantaneous response in the representation due to user interactivity (such as rotation and zooming).

A "variable" is a time dependent information unit (one unit per time increment) related to sensing a given and constant feature of the dynamic system.

"Vital signs" are key indicators that measure the system's critical functions or physiology.

In the preferred embodiments of this invention, data is gathered using methods or processes well known in the art or as appropriate and necessary. For example, in general, physiologic data, such as heart rate, respiration rate and volume, blood pressure, and the like, is collected using the various sensors that measure the functions of the natural system. Sensor-measured data is electronically transferred and translated into a digital data format to permit use by the invention. This invention uses the received measured data to deliver real-time and/or historical representations of the data and/or recorded data for later replay. Moreover, this invention permits the monitoring of the health of a dynamic system in a distributed environment. By distributed environment, it is meant that a user or users interacting with the monitoring system may be in separate locations from the location of the dynamic system being monitored. In its most basic elements, the monitoring system of this invention has three major logical components: (1) the sensors that measure the data of the system; (2) the networked computational information systems that computes the representation and that exchanges data with the sensors and the user interface; and (3) the interactive user interface that displays the desired representation and that interactively accepts the users" inputs. The components and devices that perform the three major functions of this invention may be multiple, may be in the same or different physical locations, and/or may be assigned to a specific process or shared by multiple processes.

FIG. 1a is a top-level representative diagram showing the data processing paths of the preferred embodiment of this invention operating on a natural system. The natural system 101a is shown as a dynamic entity whose origin, processes and structures (although not necessarily its maintenance) were not manmade or artificially created. Examples of natural systems are living organisms, ecological systems, and various Earth environments. In one preferred embodiment of the invention, a human being is the natural system whose physiology is being monitored. Attached to the natural system 101a are a number of sensors 102. These sensors 102 collect the physiologic data, thereby measuring the selected critical functions of the natural system. Typically, the data gathering of the sensors 102 is accomplished with methods or techniques well known in the art. The sensors 102 are typically and preferably electrically connected to a digital data formatter 103. However, in other embodiments of this invention, the sensors may be connected using alternative means including but not limited to optical, RF and the like. In many instances, this digital data formatter 103 is a high-speed analog to digital converter. Also, connected to the digital data formatter 103 is the simulator 101b. The simulator 101b is an apparatus or process designed to simulate the physiologic process underlying the life of the natural system 101a. A simulator 101b is provided to generate vital sign data in place of a natural system 101a, for such purposes as education, research, system test, and calibration. The output of the digital data formatter 103 is Real-Time data 104. Real-Time data 104 may vary based on the natural system 101a being monitored or the simulator 101b being used and can be selected to follow any desired time frame, for example time frames ranging from one-second periodic intervals, for the refreshment rates of patients in surgery, to monthly statistics reporting in an ecological system. The Real-Time data 104 is provided to a data recorder 105, which provides the means for recording data for later review and analysis, and to a data modeling processor and process 108. In the preferred embodiments of this invention the data recorder 105 uses processor controlled digital memory, and the data modeling processor and process 108 is one or more digital computer devices, each having a processor, memory, display, input and output devices and a network connection. The data recorder 105 provides the recorded data to a speed controller 106, which permits the user to speed-up or slow-down, the replay of recorded information. Scalar manipulations of the time (speed) in the context of the 3-D modeling of the dynamic recorded digital data allows for new and improved methods or reviewing the health of the systems 101a,b. A customize/standardize function 107 is provided to permit the data modeling to be constructed and viewed in a wide variety of ways according to the user's needs or intentions. Customization 107 includes the ability to modify spatial scale, such modifying includes but is not limited to zooming, translating, and rotating, attributes and viewports in addition to speed. In one preferred embodiment of the invention, the range of customization 107 permitted for monitoring natural systems 101a physiologic states is reduced and is heavily standardized in order to ensure that data is presented in a common format that leads to common interpretations among a diverse set of users. The data modeling processor and process 108 uses the prescribed design parameters, the standardized/customize function and the received data to build a three-dimensional (3-D) model in real-time and to deliver it to an attached display. The attached display of the data modeling processor and process 108 presents a representation 109 of 3-D objects in 3-D space in time to provide the visual representation of the health of the natural system 101a in time, or as in the described instances of the simulated 101b system.

Figure 1B:
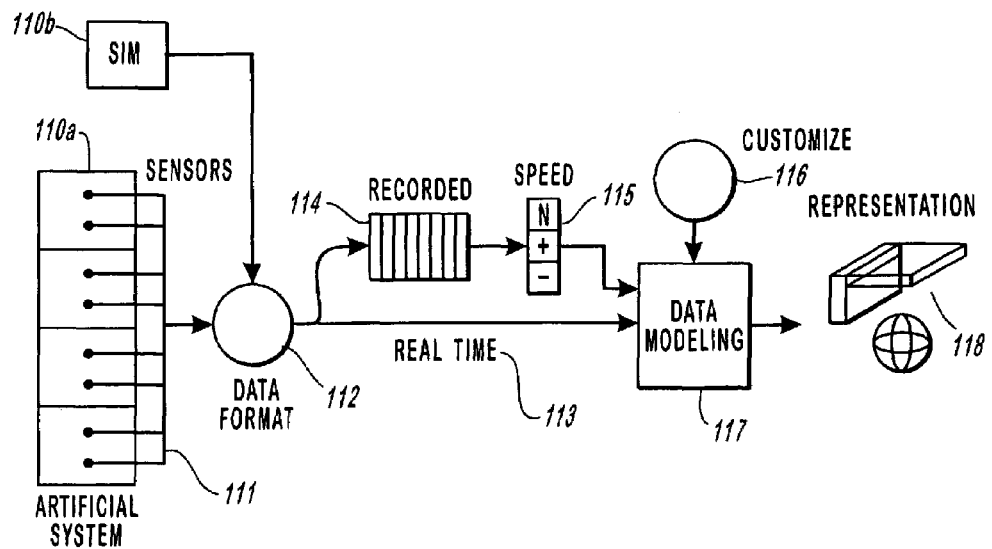
FIG. 1b is a top-level block diagram of the data processing flow of the preferred embodiment of this invention.

FIG. 1b is a top-level block diagram of the data processing flow of the preferred embodiment of this invention operating on an artificial system. An artificial system is a dynamic entity whose origin, processes and structure have been designed and constructed by human intention. Examples of artificial systems are manmade real or virtual, mechanical, electrical, chemical and/or organic entities. The artificial system 110a is shown attached to a number of sensors 111. These sensors 111 collect the various desired data, thereby measuring the selected critical functions of the artificial system. Typically, the data gathering of the sensors 111 is accomplished with methods or techniques well known in the art. The sensors 111 are connected to a data formatter 112, although alternative connection means including optical, RF and the like may be substituted without departing from the concept of this invention. In many instances, this digital data formatter 112 is a high-speed analog to digital converter. Although, in certain applications of the invention, namely stock market transactions, the data is communicated initially by people making trades. Also connected to the digital data formatter 112 is the simulator 110b. The simulator 110b is an apparatus or process designed to simulate the process underlying the state of the artificial system 110a. The simulator 110b is provided to generate vital data in place of the artificial system 110a, for such purposes as education, research, system test, and calibration. The output of the digital data formatter 112 is Real-Time data 113. Real-Time data 113 may vary based on the artificial system 110a being monitored or the simulator 110b being used and can be selected to follow any desired time frame, for example time frames ranging from microsecond periodic intervals, for the analysis of electronic systems, to daily statistics reported in an financial trading system. The Real-Time data 113 is provided to a data recorder 114, which provides the means for recording data for later review and analysis, and to a data modeling processor and process 117. In the preferred embodiments of this invention the data recorder 114 uses processor controlled digital memory, and the data modeling processor and process 117 is one or more digital computer devices, each having a processor, memory, display, input and output devices and a network connection. The data recorder 114 provides the recorded data to a speed controller 115, which permits the user to speed-up or slow-down, the replay of recorded information. Scalar manipulations of the time (speed) in the context of the 3-D modeling of the dynamic recorded digital data allows for new and improved methods or reviewing the health of the system 110a,b. A customize/standardize function 116 is provided to permit the data modeling to be constructed and viewed in a wide variety of ways according to the user's needs or intentions. Customization 116 includes the ability to modify spatial scale (such modification including, but not limited to translating, rotating, and zooming), attributes, other structural and symbolic parameters, and viewports in addition to speed. The range of customization form monitoring artificial systems" 110a,b states is wide and not as standardized as that used in the preferred embodiment of the natural system 101a,b monitoring. In this Free Customization, the symbolic system and display method is fully adaptable to the user's needs and interests. Although this invention has a default visualization space, its rules, parameters, structure, time intervals, and overall design are completely customizable. This interface mode customize/standardize function 116 also allows the user to select what information to view and how to display the data. This interface mode customization 116 may, in some preferred embodiments, produce personalized displays that although they may be incomprehensible to other users, facilitate highly individual or competitive pursuits not limited to standardized interpretations, and therefore permit a user to look at data in a new manner. Such applications as analysis of stock market data or corporation health monitoring may be well suited to the flexibility of this interface mode. The data modeling processor and process 112 uses the prescribed design parameters, the customize/standardized function 116 and the received real-time data 113 to build a three-dimensional (3-D) model in time and to deliver it to a display. The display of the data modeling processor and process 117 presents a representation 118 of 3-D objects in 3-D space in time to provide the visual representation of the health of the artificial system 110a in time, or as in the described instances of the simulated 110b system.

Figure 1C:
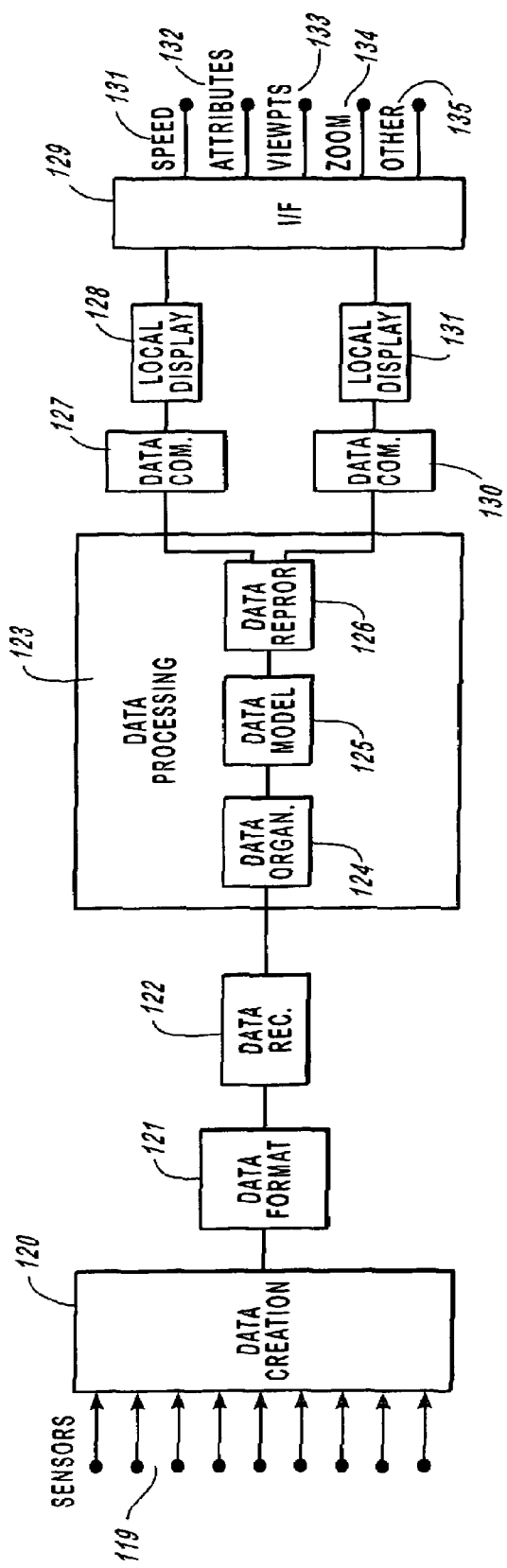
FIG. 1c is a top-level block diagram of one preferred processing path of this invention.

FIG. 1c is a top-level block diagram of one preferred processing path of this invention. Sensors 119 collect the desired signals and transfer them as electrical impulses to the appropriate data creation apparatus 120. The data creation apparatus 120 converts the received electrical impulses into digital data. A data formatter 121 receives the digital data from the data creation apparatus 120 to provide appropriate formatted data for the data recorder 122. The data recorder 122 provides digital storage of data for processing and display. A data processor 123 receives the output from the data recorder 122. The data processor 123 includes a data organizer 124 for formatting the received data for further processing. The data modeler 125 receives the data from the data organizer and prepares the models for representing to the user. The computed models are received by the data representer 126, which formats the models for presentation on a computer display device. Receiving the formatted data from the data processor 123 is a number of data communication devices 127, 130. These devices 127, 130 include a central processing unit, which controls the image provided to one or more local displays 128, 131. The local displays may be interfaced with a custom interface module 129 which provides user control of such attributes as speed 131, object attributes 132, viewports 133, zoom 134 and other like user controls 135.

Figure 1D:
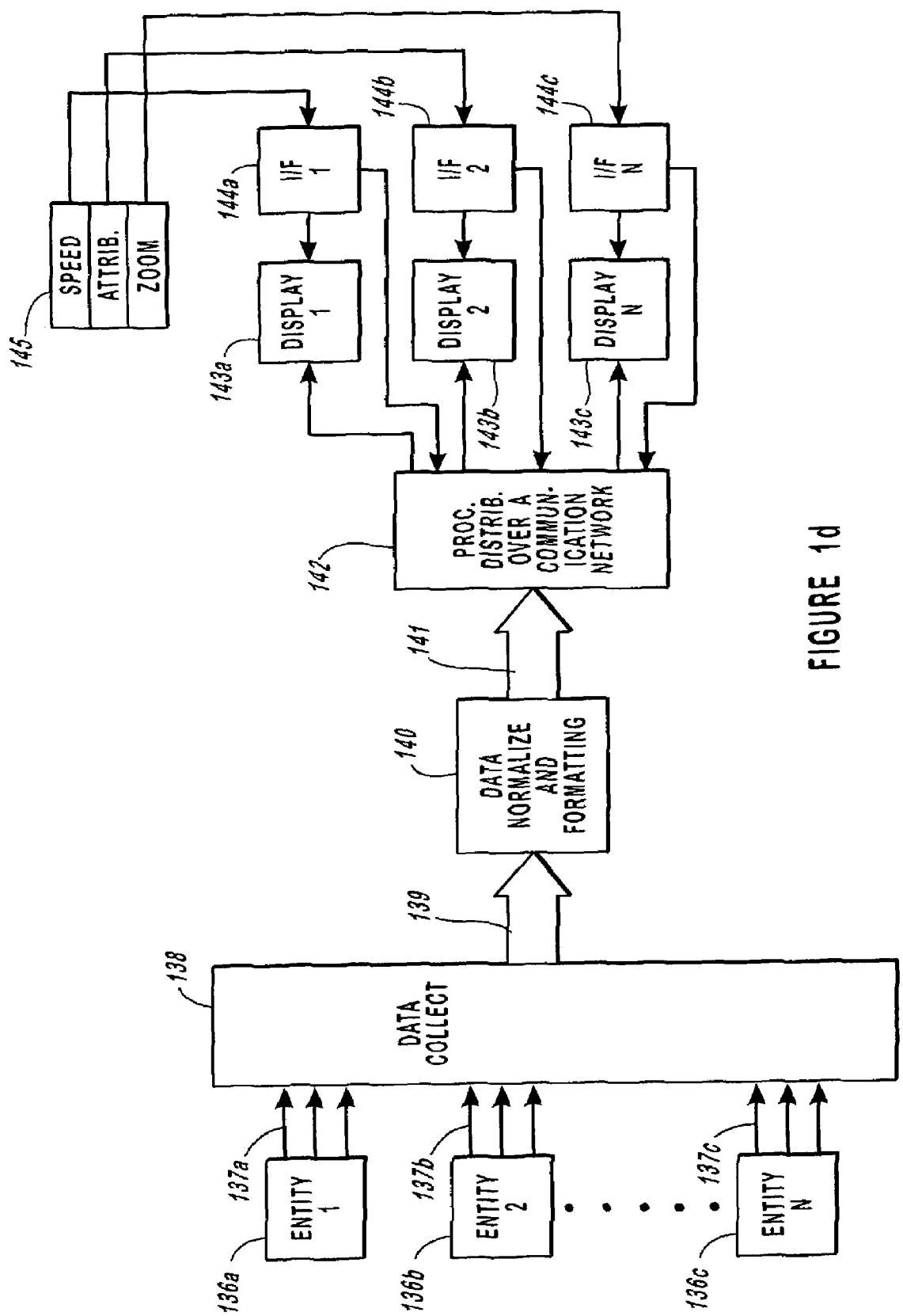
FIG. 1d is a top-level block diagram of a second preferred processing path of this invention.

FIG. 1d is a top-level block diagram of a second preferred processing path of this invention. In this embodiment of the invention a plurality of entities 136a,b,c are attached to sensors 137a,b,c which communicate sensor data to a data collection mechanism 138, which receives and organizes the sensed data. The data collection mechanism 138 is connected 139 to the data normalize and formatting process 140. The data normalize and formatting process 140 passes the normalized and formatted data 141 to the distributed processors 142. Typically and preferably the processing 142 is distributed over the Internet, although alternative communication networks may be substituted without departing from the concept of this invention. Each processing unit 142 is connected to any of the display devices 143a,b,c and receives command control from a user from a number of interface units 144a,b,c, each of which may also be connected directly to a display devices 143a,b,c. The interface units 144a,b,c receive commands 145 from the user that provide speed, zoom and other visual attributes controls to the displays 143a,b,c.

FIGS. 2a, 2b, 2c, and 2d are representative 3-D objects representing critical functions. Each 3-D object is provided as a symbol for a critical function of the entity whose health is being monitored. The symbol is created by selecting the interdependent variables that measure a particular physiologic function and expressing the variable in spatial (x,y,z) and other dimensions. Each 3-D object is built from 3-D object primitives (i.e., a cube, a sphere, a pyramid, a n-polygon prism, a cylinder, a slab, etc.). More specifically, the spatial dimensions (extensions X, Y and Z) are modeled after the most important physiologic variables based on (1) data inter-dependency relationships, (2) rate, type and magnitude of change in data flow, (3) geometric nature and perceptual potential of the 3-D object, for example a pyramid versus a cylinder, (4) potential of the object's volume to be a data-variable itself by modeling appropriate data into x, y and z dimensions (e.g., in one preferred application of the invention, cardiac output is the result of heart rate (x and y dimensions) and stroke volume (z)), (5) orthographic viewing potential (see viewport) and (6) the relationship with the normal values framework.

The first representative object 201, shown in FIG. 2a, is an engine process. The object 201 representing this process is provided on a standard x-y-z coordinate axis 202. The correlation between temperature, shown in the x1-dimension 204, engine RPM, shown in the y1-dimension 205 and exhaust gas volume, shown in the z1-dimension 203 is shown by changes in the overall sizes and proportion of the object 201. In the shown example object 201 the engine gas volume 203 is large, when RPM 205 is low and the engine temperature 204 is in the middle range. This combination of values, even without specific identified values suggests an engine's starting point.

The second representative object 206, shown in FIG. 2b, is an object representing cardiac function using stroke volume, in the y2-dimension 209, and the heart rate per second, shown as the x2, z2 dimensions. The total cardiac volume is shown as the total spherical volume 208.

The third representative object 211, shown in FIG. 2c, represents the interaction between the number of contracts, shown in the y3-dimension 212, the average revenue per contract, shown in the z3-dimension 214, and the average time per contract, shown in the x3-dimension 213. Assessing the interaction among these variables is important in monitoring of a sales department's operations.

The fourth representative object 215 is shown in FIG. 2d, shows the respiratory function generated by the respiratory rate, shown in x4-dimension 216, the respiratory volume, shown in the y4-dimension 216, and inhalation/exhalations, shown in the z4-dimension 218.

Figure 3:
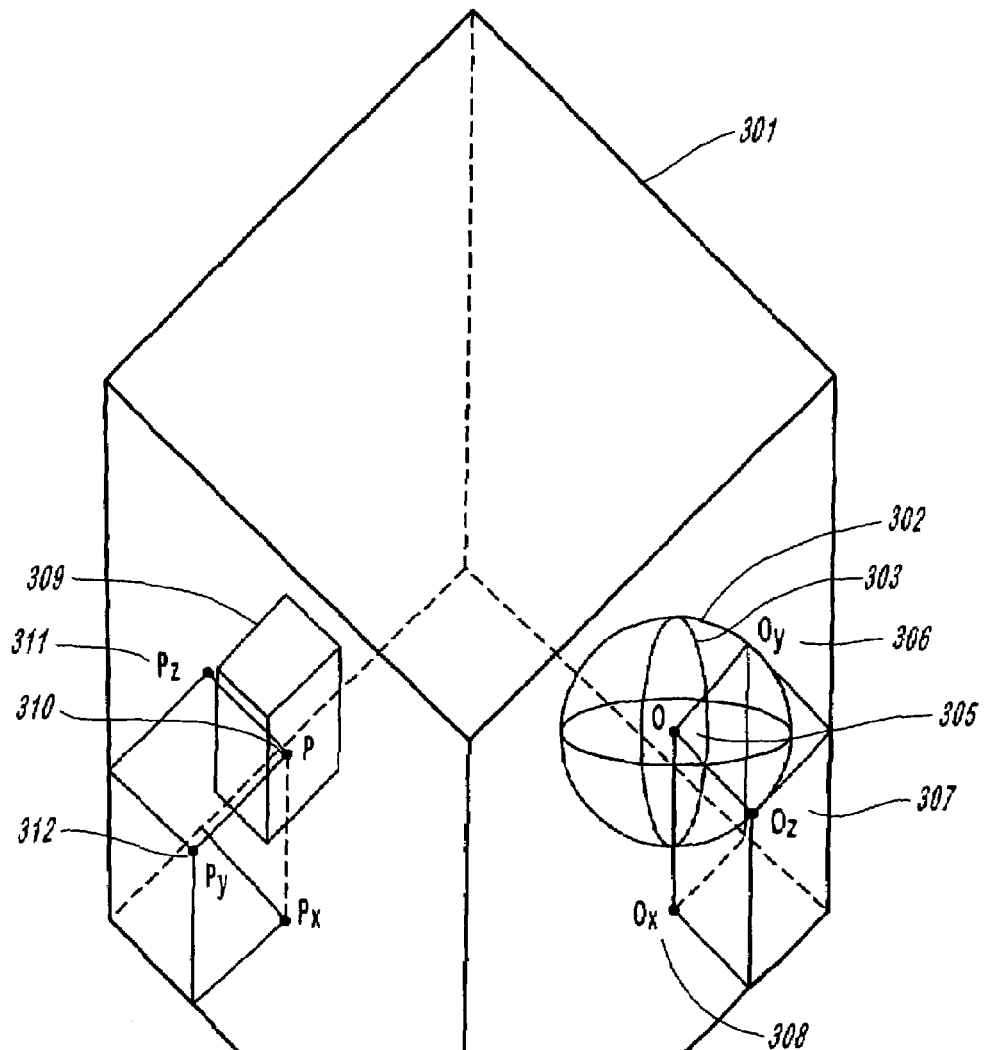
FIG. 3 is a representation of data objects in H-space.

FIG. 3 is a representation of data objects in H-space 301. Data sets are represented as 3-D objects of various characteristics and relationships within a 3-D representation space. The data representation environment in this figure is used to map the physiologic data in 3-D and is what is referred to as "Health-space" or "H-space"301. The 3-D objects are placed within H-space on the 3 coordinates of their geometric centers. The coordinates for an object's geometric center depends on the relevant data associated to the particular critical function the object represents. For example, in the preferred embodiment, the cardiac function object, shown as a spherical object 302, is placed in H-space 301 based on Mean Blood Pressure, designated as Oy 306 and Oxygen Saturation in the Blood, shown as Oz 307. In the other example object, the prism 309 is placed in H-space 301 depending on sales profit, shown as Py 312, and products in stock, shown as Pz, 311. The location of 3-D objects in H-space 301 allows for the overall extension envelope of H-space, the relationship between 3-D objects and spaces within H-space 301, the viewport display areas and the departure from normative values. Typically and preferably the centers of the objects 302, 309 are located in the middle of the x-dimension of H-space 301.

Figure 4A:
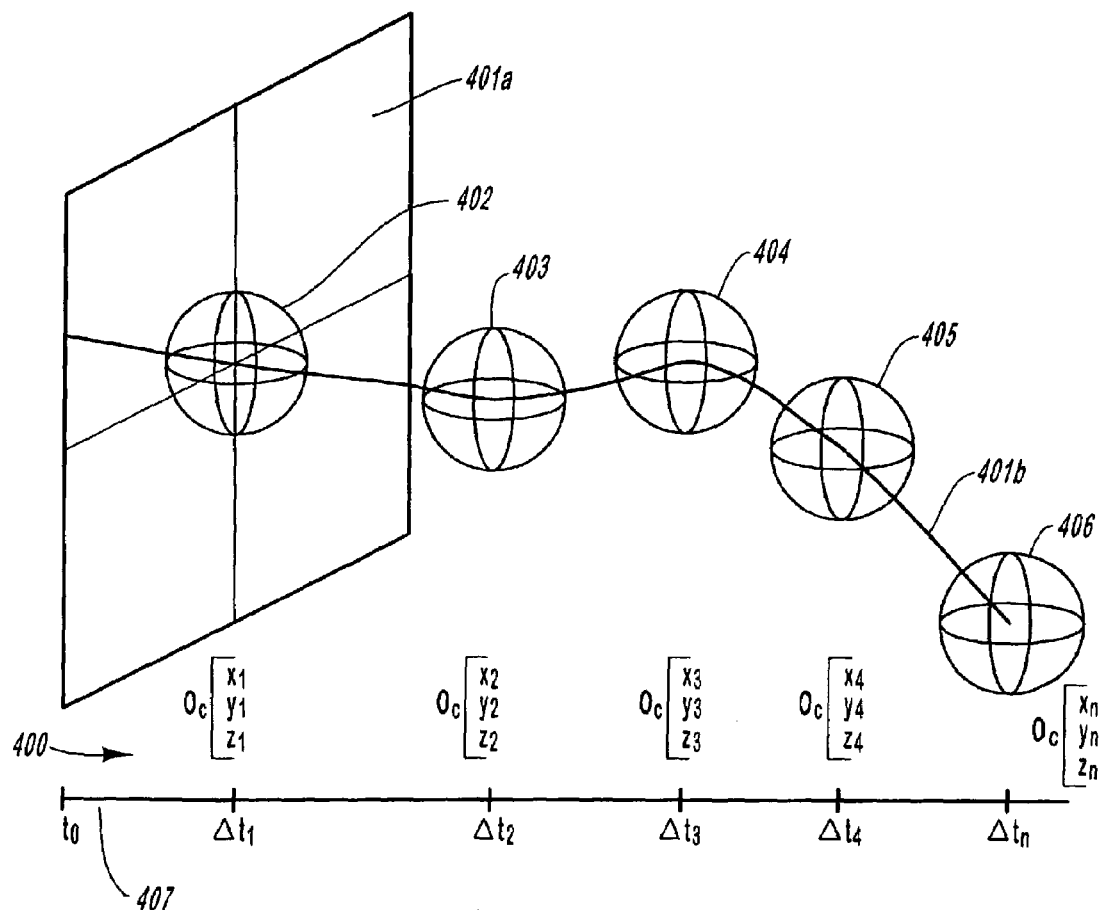
FIGS. 4a and 4b are representative views of changes in data objects in time.
Figure 4B:
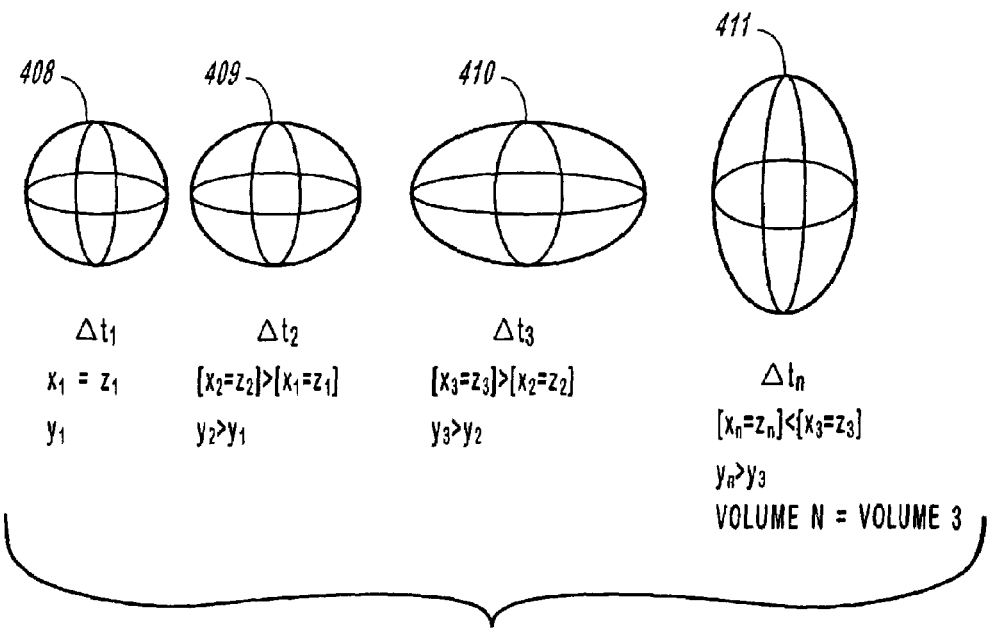

FIGS. 4a and 4b are representative views of changes in data objects in time. In FIG. 4a, the x-coordinate 400 is used to measure the temporal dimension of an objects 402 trajectory. The y-z plane 401a determines the location of an object's geometric center within H-space. Increases or decreases in data values associated with the coordinates of the object's geometric center that make that object's location change in time as shown in path line 401b. In this view, the object 402 is presented in four different time intervals 403, 404, 405, 406, thereby creating a historical trajectory. The time intervals at which the object 402 is shown are provided 407. In FIG. 4b, increases in size and proportion are presented, 408, 409, 410, 411 providing an example of changes in values. The monitoring of these changes in time assists the user in establishing and evaluating comparative relationships within and across H-states.

Figure 5A:
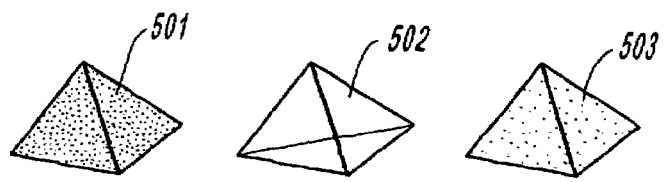
FIGS. 5a, 5b, 5c, 5d, 5e, 5f, 5g and 5h are representative views of properties of data objects provided in the preferred embodiment of this invention.
Figure 5B:
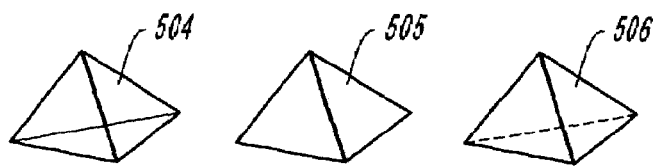
Figure 5C:
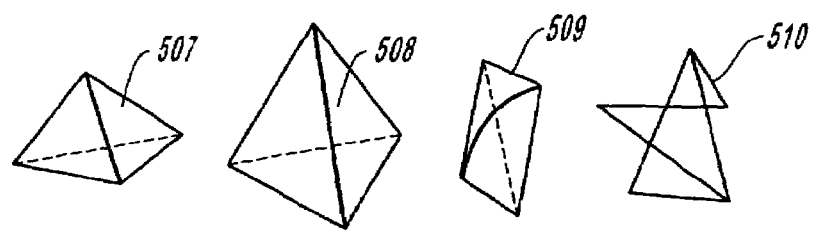
Figure 5D:
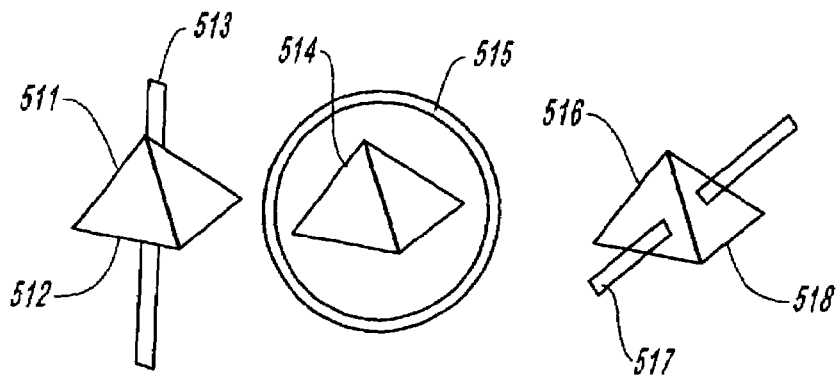
Figure 5E:
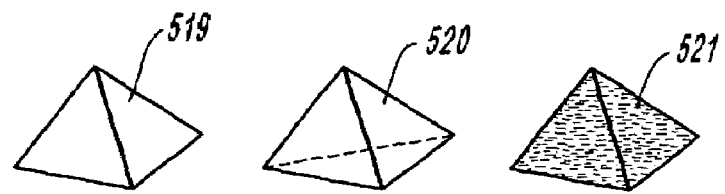
Figure 5F:
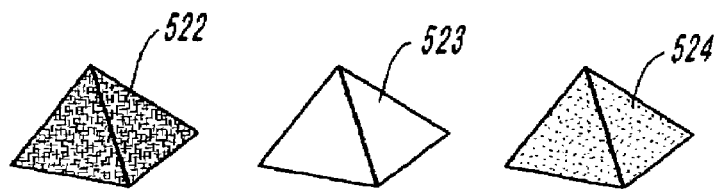
Figure 5G:
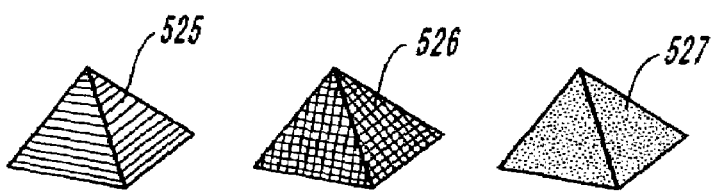
Figure 5H:
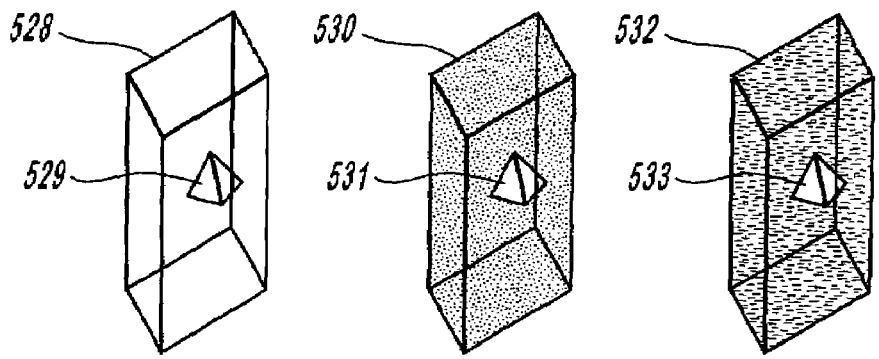

FIGS. 5a, 5b, 5c, 5d, 5e, 5f, 5g and 5h are representative views of properties of data objects provided in the preferred embodiment of this invention. In addition to the three x-y-z spatial dimensions used for value correlation and analysis, 3-D objects may present data value states by using other geometric, aesthetic, and aural attributes that provide for the mapping of more physiologic data. These figures show some of the representative other geometric, aesthetic, and aural attributes supported for data presentation in this invention. FIG. 5a shows changes in apparent volumetric density. A solid object 501 is shown in relation to a void object 502 and an intermediate state 503 object. FIG. 5b shows changes in apparent 3-D enclosure. An open object 504, a closed object 505, and an intermediate state 506 is shown. FIG. 5c shows the apparent degree of formal deformation. A normal object 507, a distorted object 508, a transformed object 509, and a destroyed object 510 are shown in comparison. FIG. 5d shows secondary forms of the objects. "Needles" 513 protruding through a standard object 512 in combination 511 is shown in comparison with a boundary 515 surrounding a standard object 514 and a bar 517 protruding into the original form object 518 forming a new combination object 516 are shown providing additional combination supported in this invention. FIG. 5e shows the various degrees of opacity of the object's surface, showing an opaque object 519, a transparent object 520 and an intermediate state object 521. FIG. 5f shows the various degrees of texture supported by the object display of this invention, including a textured object 522, a smooth object 523 and an intermediate textured object 524. FIG. 5g is intended to represent various color hue possibilities supported for objects in this invention. An object with color hue is represented 525 next to a value hue object 526 and a saturation hue object 527 for relative comparison. Naturally, in the actual display of this invention colors are used rather than simply the representation of color shown in FIG. 5g. FIG. 5h shows the atmospheric density of the representation space possible in the display of objects in this invention. An empty-clear space 528, a full-dark space 530 and an intermediate foggy space 523 are shown with 3-D objects shown within the representative space 529, 531, 533.

Aural properties supported in this invention include, but are not limited to pitch, timbre, tone and the like.

Figure 6:
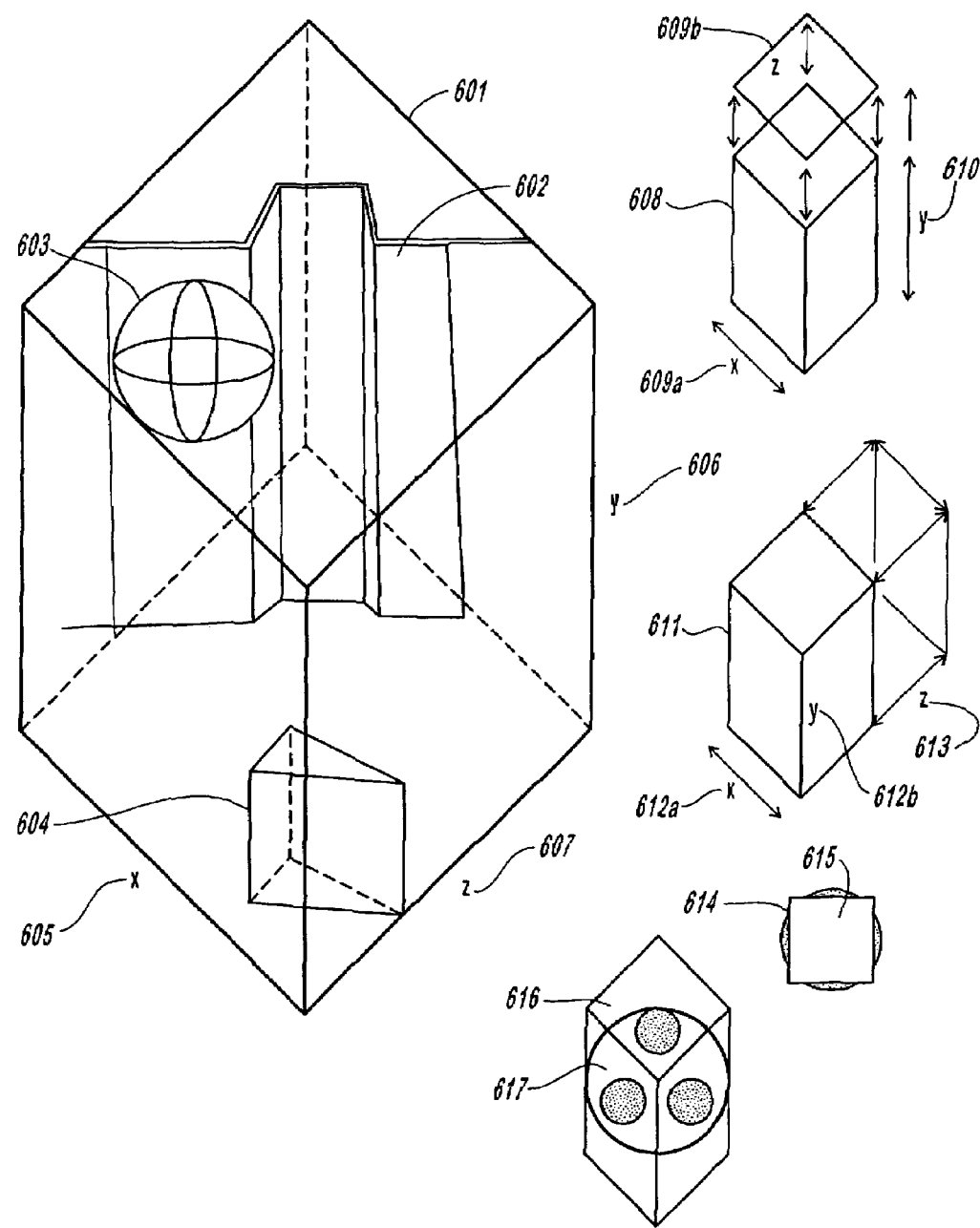
FIG. 6 shows a 3-D configuration of the objects in H-space in the preferred embodiment of the invention.

FIG. 6 shows the 3-D configuration of the objects in H-space in the preferred embodiment of the invention. In this view the local level, H-space 601 is shown within which the 3-D objects 602, 603, and 604 are located. Object 602 represents the respiratory function of an individual. Its 602 x-y-z dimensions change based on the parameter-based dimensional correlation. The object 603 represents the efficiency of the cardiac system by varying the x,y,z coordinates of the object. The object 604 represents a human brain function, also with the x,y,z dimensions changing based on the parameter-based dimensional correlation. In this way the user can easily view the relative relationships between the three physiological objects 602, 603, 604. Within H-space 601, the temporal coordinate (i.e., periodic time interval for data capturing that defines how H-space is plotted in Live-space see FIG. 7) is a spatial dimension on which data is mapped. The x-dimension of 605 of the H-space 601 can be mapped to another independent variable such as heart rate period, blood pressure or the like. The location of an object in the y-dimension 606 of H-space 601 can be mapped to additional variables that are desired to be monitored such as SaO2 content, CaO2 content, or temperature in the blood. The location of an object in the z-dimension 607 of the H-space 601 can also be mapped to additional variables that the user desires to monitor. A hypothetical object 608 shows that the three coordinates are contextual to a particular object 608 and need not be the same for all objects, except in the object's 608 extension measuring properties. Fixed x- and z-dimension values 609a and 609b are shown as constant. The y-value 610 of this object 608 changes to fluctuating values or data type that results in the height of the object 608 increasing or decreasing. This view shows another object 611 showing the relationship between the three dimensions. Constant x- and y-values 612a and 612b are shown. The z-value 613 of this object 611 changes to fluctuating values or data types that result in the width of the object 611 increasing or decreasing. An overlapping view 614 of an object 615 that has extended past the H-space limitation. A limit of H-space 616 with a spherical object 617 located inside H-space 616 shown with the degree of extension shown in shaded circles.

Figure 7:
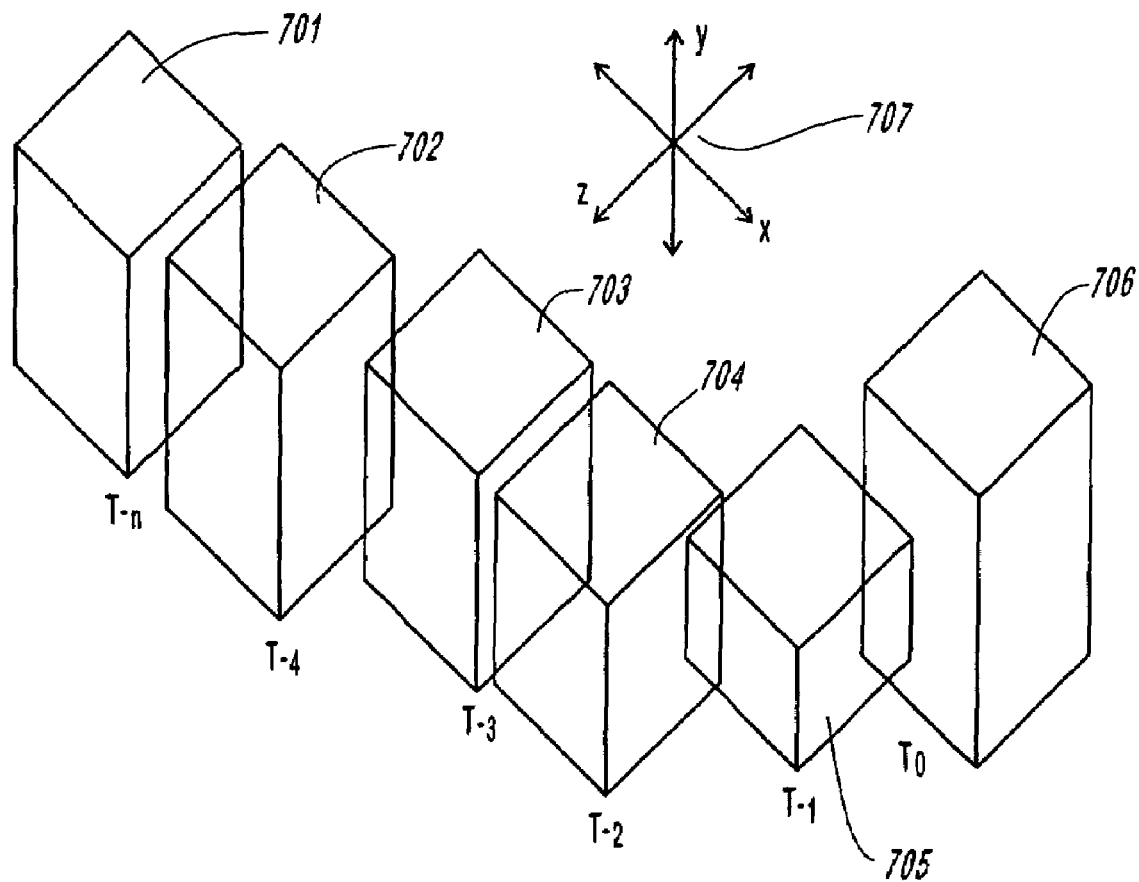
FIG. 7 shows H-space with a time coordinate along with local-space coordinates.

FIG. 7 shows a series of H-spaces 701, 702, 703, 704, 705, 706 along a global time coordinate 708, and the local-space coordinates 707 that governs each H-space. Each of these H-spaces represents progressive states of the dynamic system at pre-established temporal intervals ($T_0, T_{-1}, T_{-2}, \ldots T_{-n}$) and the six 701, 702, 703, 704, 705, 706 together show the evolution of that system over time, demonstrating the historical representation of individual H-states within an overall "Life-space" or "L-space." At the global level (or L-space), one of the coordinates, typically x, is always time. The temporal coordinate is scaled based on the intervals at which a particular functions system's physiologic data are collected by the art or as appropriate. This interval or module is fixed and constant across L-space and provides the necessary temporal frame of reference for comparing different H-spaces. The fixed temporal interval also determines the maximum x-extension of the representation envelope of H-space. The other two coordinates, y and z, provide L-space with extension and are not fixed. The three coordinates thus described provide a regulating 3-D environment within which the H-states can be visualized and related to each other.

Figure 8A:
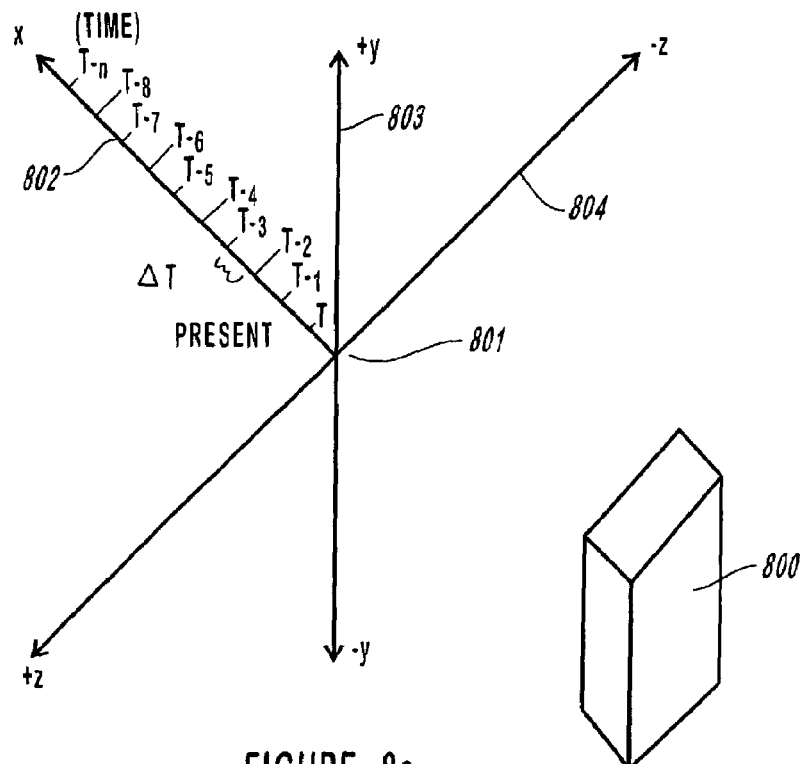
FIGS. 8a and 8b show the global level coordinate system of the preferred embodiment of this invention.
Figure 8B:
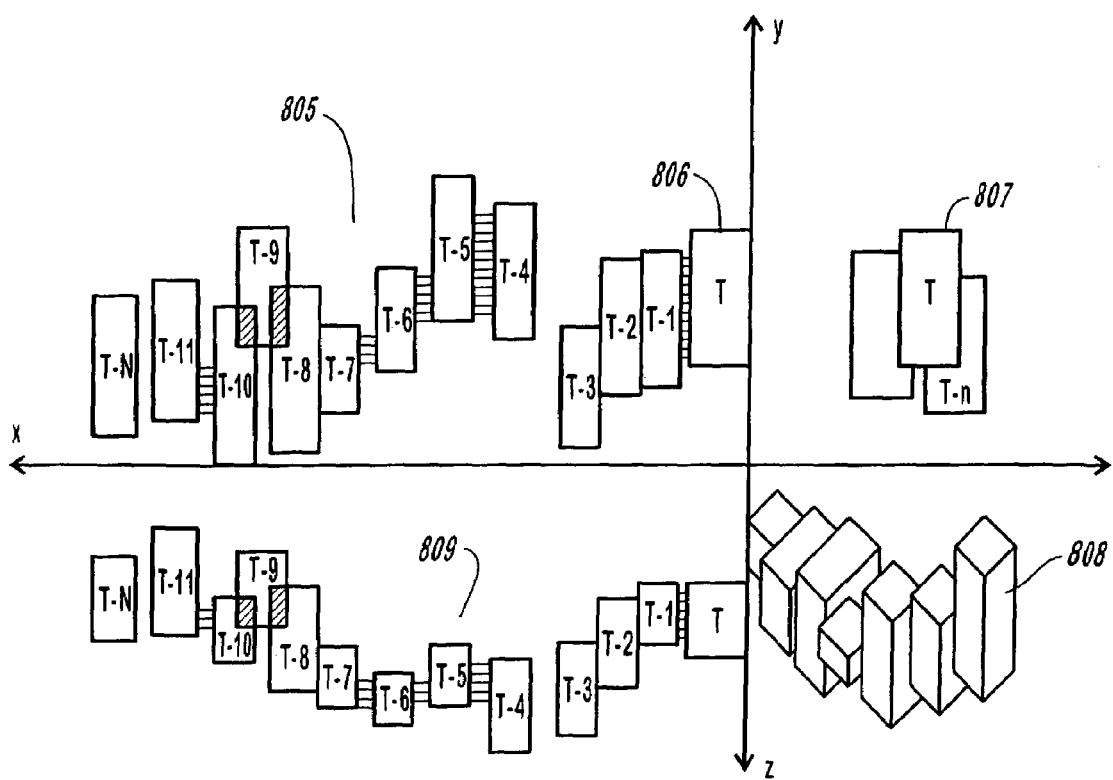

FIGS. 8a and 8b show the global level coordinate system of the preferred embodiment of this invention. FIG. 8a shows the L-space coordinate system 801 in its preferred embodiment. The x-dimension 802 of L-space is mapped to a constant time interval, set by means standard in the art or otherwise as appropriate. The present position of H-state is also indicated on the x-dimension 802. The y-dimension 803 in both positive and negative extensions is measured, up and down from the x-axis. This dimension 803 can be mapped to a data variable within particular 3D object in space. The z-dimension 804 is shown in both positive and negative extensions measured forwards and backwards from the intersecting x-axis. This dimension 804 can be mapped to a data variable within a particular 3D object in space. Now for FIG. 8b a prismatic object 800 represents a critical function, whose evolution is being monitored in L-space, of a given dynamic system. The front view 805 shows the different H-states of the prism/function 800 using a time T to T-n historical trend. The level of intersection and separation between the front views of the prism indicate abnormal health states of the critical function the object 800 represents. No separation or intersection shows normal function conditions. The trajectory in the y-dimension of the prism (i.e., H-states of the critical function) are mapped to a variable that cause their relative position to change in the + and y dimension. The current state 806 of the prism is shown in this front view 805. A top view of 809 of the three-dimensional L-space is shown, showing the evolution of the prism 800 backward in time and showing a T to T-N historical trend. The level of intersection and separation indicate abnormal health states of the particular critical function the prism represents. No separation or intersection shows normal conditions. The trajectory in the z-dimension of the object is mapped to a variable that causes their position to change in the + and z dimension. This top view shows both the z and y trajectories in one comprehensive view. The perspective view 808 of L-space gives a comprehensive view of the interaction of the prisms (the H-states of the function) and their movement in all dimensions. The side view 807 of L-space shows the prisms and their positions in L-space giving a simultaneous view of z and y trajectories.

Figure 9A:
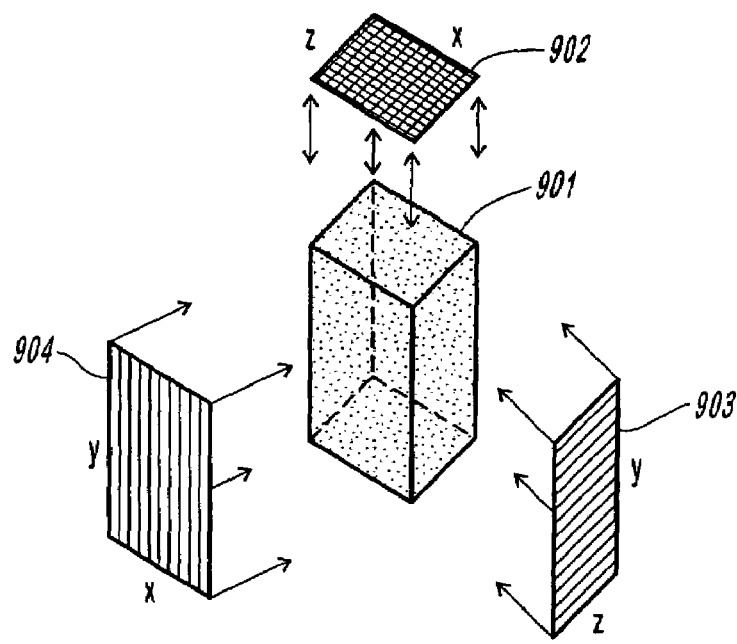
FIGS. 9a and 9b show various viewpoints of the data within H-space in the preferred embodiment of this invention.
Figure 9B:
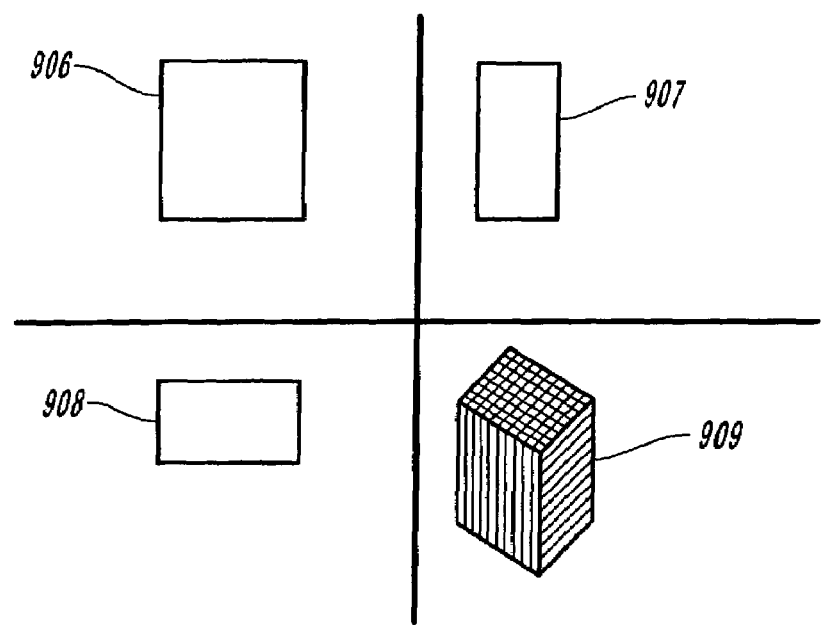

FIGS. 9a and 9b shows various viewpoints in which the data may be visualized in the preferred embodiment of this invention. This figure shows representations of a data object (a prism) and is provided to show that there are two basic types of viewports: orthographic and perspectival. The orthographic viewports 906, 907, 908, of FIG. 9b use a parallel system of projection to generate representations of H-space that maintains dimensional constancy without deformation. Some examples of orthographic views include traditional architectural or engineering views of objects, such as a top view, a front view, and a side view. The orthographic viewport allows for accurate and focused 2-D expressions of the actual 3-D object. The perspectival viewport 909, shown in FIG. 9*b* uses a focal system of projection to generate depictions analogous to our perception of reality but at the cost of deformation and lack of dimensional constancy. For example, the top view 902 along with the side view 903 and the front view of 904 of the 3-D data object 901 are shown in FIG. 9*a*. FIG. 9*b* shows three orthogonal views 906, 907, 908 along with a perspective view 909 of the current data object. The number and types of viewports used in a particular embodiment of the invention may range from one type, for example a perspective viewport allowing immerse virtual reality, to combinations of both types. In the preferred current embodiment, there are the four viewports shown in FIG. 9*b*. Given the 3-D nature of data objects and H-space, viewports provide the user with different depictions of the same data.

Figure 10:
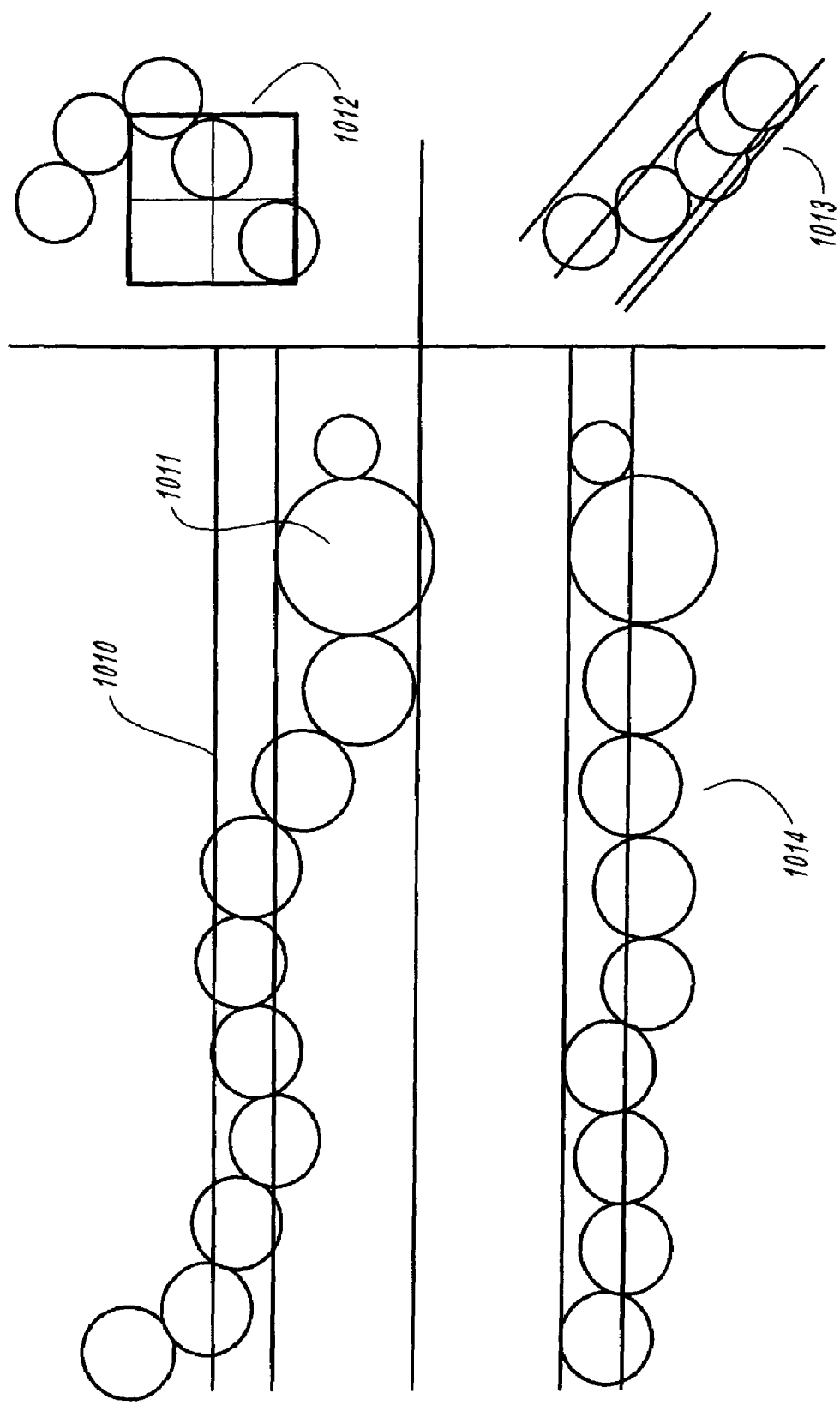
FIG. 10 shows the transformation of an object in space in context, with a reference framework, in the preferred embodiment of this invention.

FIG. 10 shows the transform of an object in space in context, with a reference framework, in the preferred embodiment of this invention. The referential framework 1010 is typically set based on population normals or patient normals. This framework assists the user to see deviations from normal very quickly. An individual spherical object 1011 that represents cardiac function is shown located in L-space and in relation to the referential framework. A side view 1012 is shown along with several cardiac objects. In this view the referential framework provides a center target point so that a user can make the necessary corrections to bring the object back to the ideal center of the framework. A perspectival view 1013 of the framework is also shown along with several cardiac objects. The top view 1014 of the framework is shown with several spherical objects (representing cardiac states). This figure demonstrates the variety of viewports provided to the user by this invention, which provides enhanced flexibility of analysis of the displayed data.

Figure 11A:
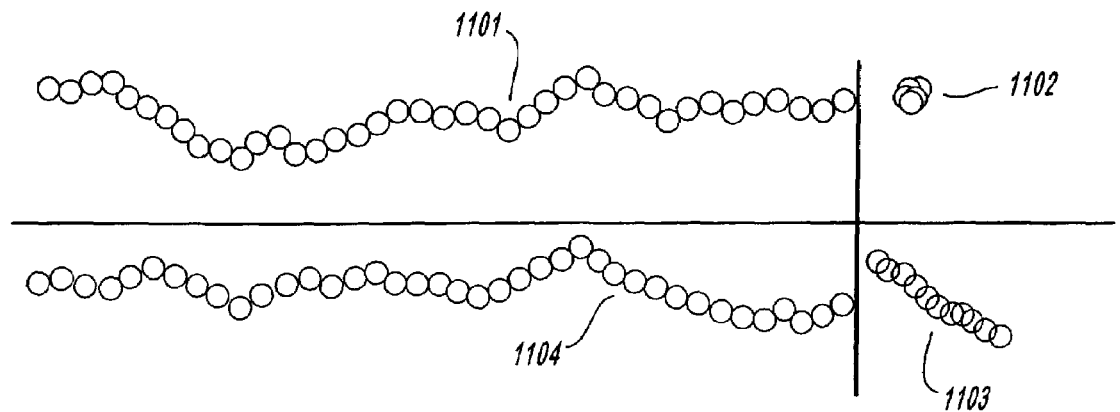
FIG. 11a shows the zooming out function in the invention.

FIG. 11*a* shows the zooming out function in the invention. This invention provides a variety of data display functions. This figure shows the way views may be zoomed in and out providing the relative expansion or compression of the time coordinate. Zooming out 1101 permits the user to look at the evolution of the system's health as it implies the relative diminution of H-states and the expansion of L-space. This view 1101 shows a zoomed out view of the front view showing a historical view of many health states. A side view 1102 zoomed out view is provided to show the historical trend stacking up behind the current view. A 3-D perspectival, zoomed out view 1103 showing the interaction of H-states over a significant amount of time is provided. A zoomed out top view 1104 shows the interaction of H-states over a large amount of time.

Figure 11B:
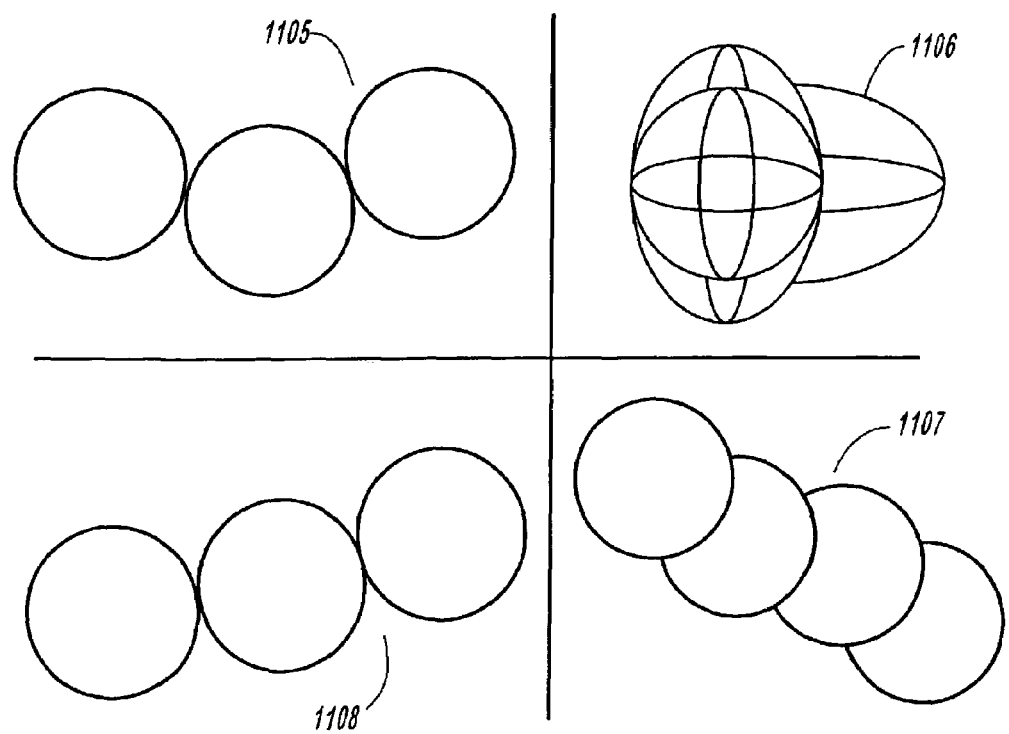
FIG. 11b shows the zooming in function in the invention.

FIG. 11*b* shows the zooming in function of the invention. The zooming in front view 1105 is shown providing an example of how zooming in permits a user to focus in on one or a few H-states to closely study specific data to determine with precision to the forces acting on a particular H-state. A zoomed in side view 1106 is provided showing the details of specific variables and their interactions. A zoomed in 3-D perspective view 1107 of a few objects is also shown. Also shown is a zoomed in top view 1108 showing the details of specific variables and their interaction.

Figure 12A:
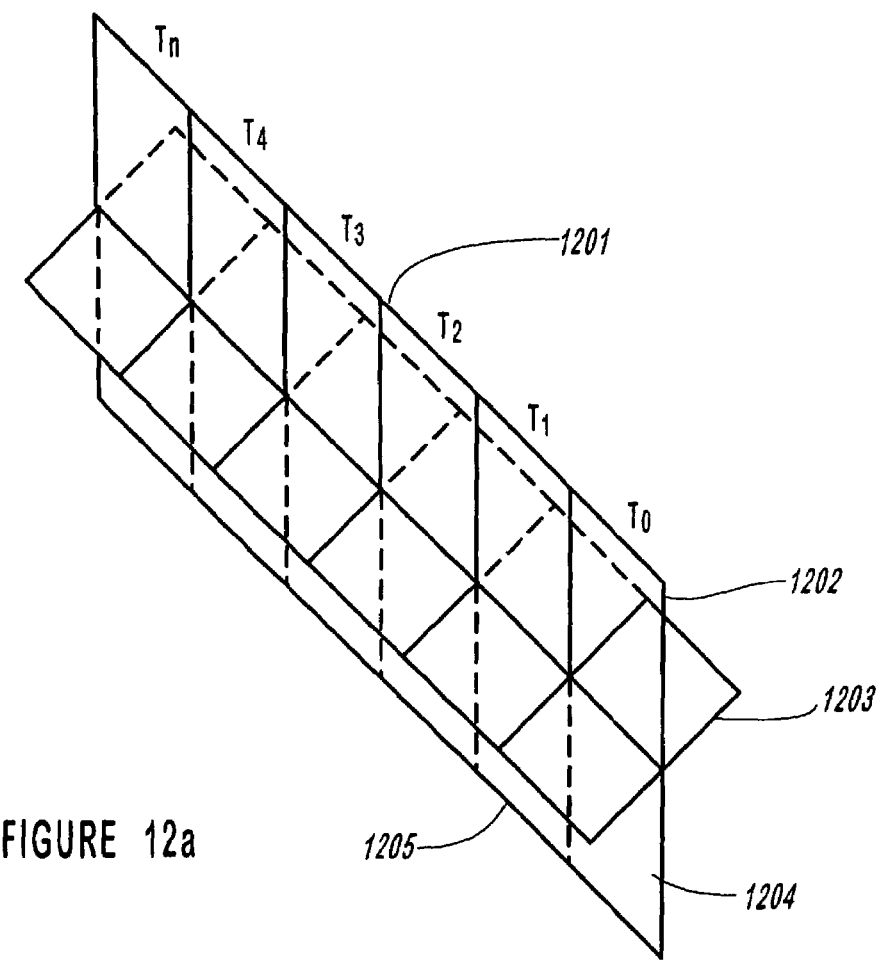
FIGS. 12a and 12b show a 3-D referential framework of normative values.
Figure 12B:
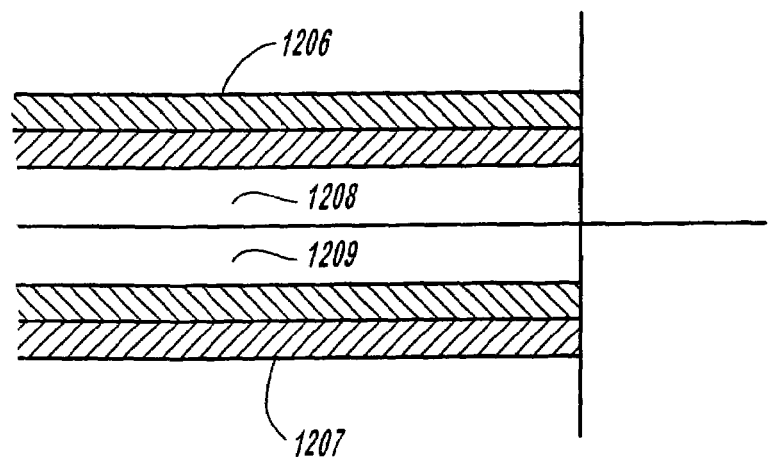

FIGS. 12*a* shows a 3-D referential framework of normative values that is provided to permit the user a direct comparison between existing and normative health states, thereby allowing rapid detection of abnormal states. The reference framework 1201 works at both the global L-space level and the local H-space level. "Normal" values are established based on average historical behavior of a wide population of systems similar to the one whose health is being monitored. This normal value constitutes the initial or by-default ideal value, which, if necessary may be adjusted to acknowledge the particular characteristics of a specific system or to follow user-determined specifications. The highest normal value of vital sign "A"202 (+y) is shown, along with the lowest normal value of "B"1203 (−z), the lowest normal value of vital sign "A" 1204 (−y) and the highest normal value of vital sign "B"1205 (+z). In FIG. 12*b*, abnormal values of "A" and "B" are shown in an orthogonal view. An abnormally high value of "A"1206, an abnormally low value of "B" 1207, an abnormally low value of "A"1208 and an abnormally high value of "B"1209 are shown.

FIG. 13 shows a comparison of the interface modes of the preferred embodiment of this invention. This invention provides two basic types of interface modes: (a) standardized or constrained customization; and (b) free or total customization. Each is directed toward different types of applications. The standardized or constrained customization 1301 uses a method and apparatus for user interface that is set a-priori by the designer and allows little customization. This interface mode establishes a stable, common, and standard symbolic system and displaying method that is "user-resistant". The fundamental rules, parameters, structure, time intervals, and overall design of L-space and H-space are not customizable. Such a normalized symbolic organization creates a common interpretative ground upon which different users may arrive at similar conclusions when provided common or similar health conditions. This is provided because similar data flows will generate similar visualization patterns within a standardized symbolic system. This interface method is intended for social disciplines, such as medicine in which common and agreeable interpretations of the data are highly sought after to ensure appropriate and verifiable monitoring, diagnosis and treatment of health states. The customization permitted in this mode is minimal and is never threatening to render the monitoring device incomprehensible to other users.

The free or total customization interface mode 1302 provides a symbolic system and displaying method that is changeable according to the user's individual needs and interests. Although the invention comes with a default symbolic L-space and H-space, its rules, parameters, structure, time intervals, and overall design are customizable. This interface mode also permits the user to select what information the user wishes to view as well as how the user wishes to display it. This interface mode may produce personalized displays that are incomprehensible to other users, but provides flexibility that is highly desired in individual or competitive pursuits that do not require agreeable or verifiable interpretations. Examples of appropriate applications may include the stock market and corporate health data monitoring.

Figure 14:
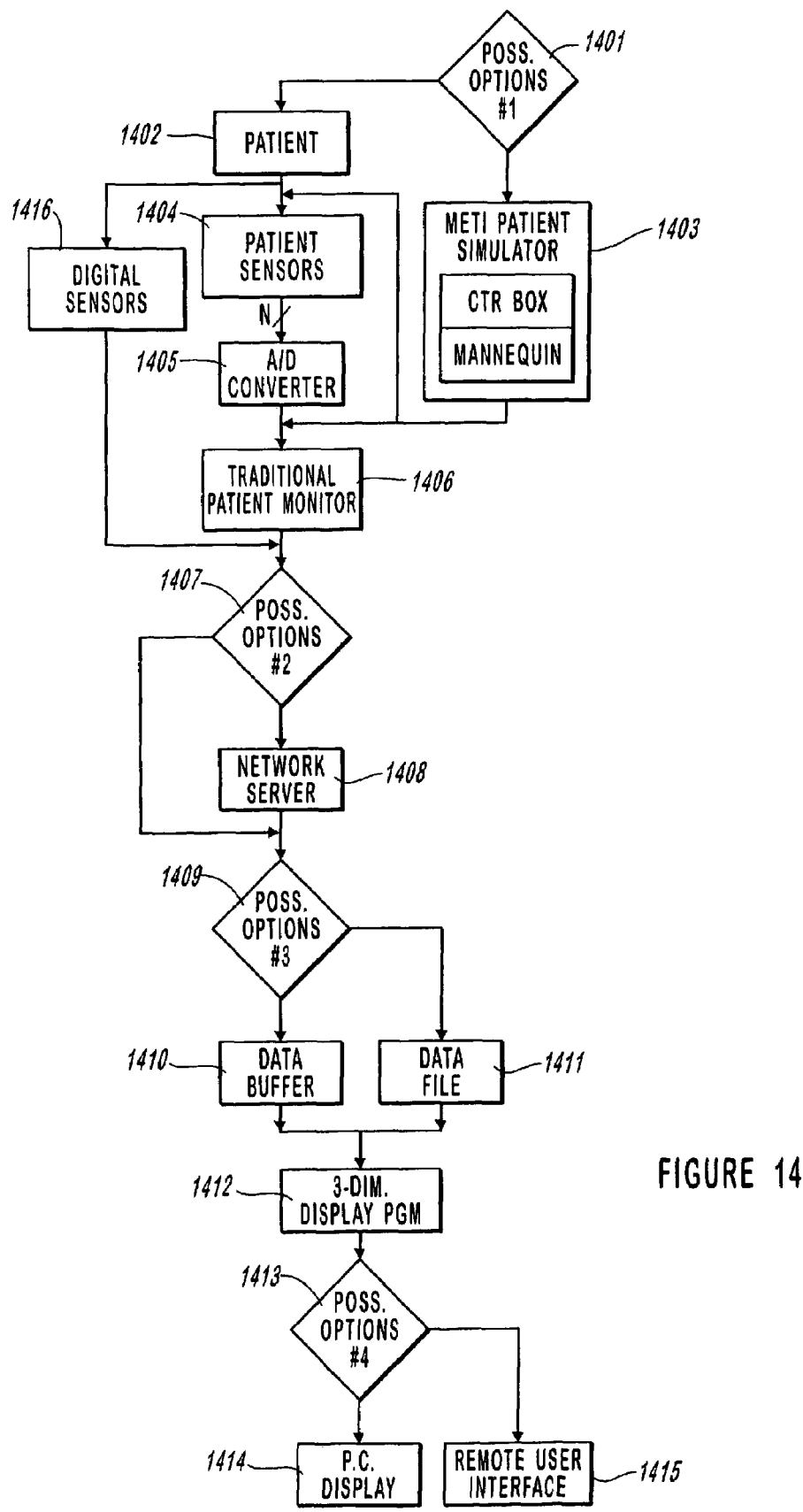
FIG. 14 is a hardware system flow diagram showing various hardware components of the preferred embodiments of the invention.

FIG. 14 is a hardware system flow diagram showing various hardware components of the preferred embodiments of the invention in a "natural system" medical application. Initially a decision 1401 is made as to the option of using data monitored on a "real" system, that is a real patient, or data from the simulator, for anesthesiology training purposes. If the data is from a real patient, then the patient 1402 is provided with patient sensors 1404, which are used to collect physiological data. Various types of sensors, including but not limited to non-invasive BP sensors, ECG leads, SaO2 sensors and the like may be used. Digital sensors 1416 may also provide physiological data. An A/D converter 1405, is provided in the interface box, which receives the analog sensor signals and outputs digital data to a traditional patient monitor 1406. If the data is produced 1401 by the simulator 1403, a control box and mannequins are used. The control box controls the scenarios simulated and the setup values of each physiological variable. The mannequins generate the physiological data that simulates real patient data and doctors collect the data through different, but comparable sensors. The traditional patient monitor 1406 displays the physiological data from the interface box on the screen. Typically and preferably, this monitor 1406 is the monitor used generally in an ICU. A test 1407 is made to determine the option of where the computations and user interface are made, that is whether they are made on the network server 1408 or otherwise. If a network server 1408 is used, all or part of the data collection and computation may be performed on this computer server 1408. An option 1409 is proved for running a real time representation versus a representation delayed or replayed from events that previously occurred. For real time operation, a data buffer 1410 is provided to cache the data so that the representation is played in real time. For the replay of previous events, a data file 1411 provides the means for permanently storing the data so that visualization is replayed. The visualization software 1412 runs on a personal computer and can display on its monitor or on remote displays via the internet or other networking mechanism. Typically the physiological data measured on either a real patient or the simulator are fed to the personal computer from the traditional data monitor. A standard interface such as RS232, the internet, or via a server, which receives data from the monitor, may serve as the communication channel to the personal computer running the visualization software 1412. This program 1412 is the heart of the invention. The program 1412 computes the representation and processes the user interface. An option 1413 is provided for computing and user interface on the local desktop personal computer or for distribution across the Internet or other network mechanism. If a local desktop personal computer is selected, the personal computer 1414 with an adequate display for computation of the visualization and user interface is provided. If a remote user interface 1415 is selected the display and user interface is communicated across the Internet.

Figure 15:
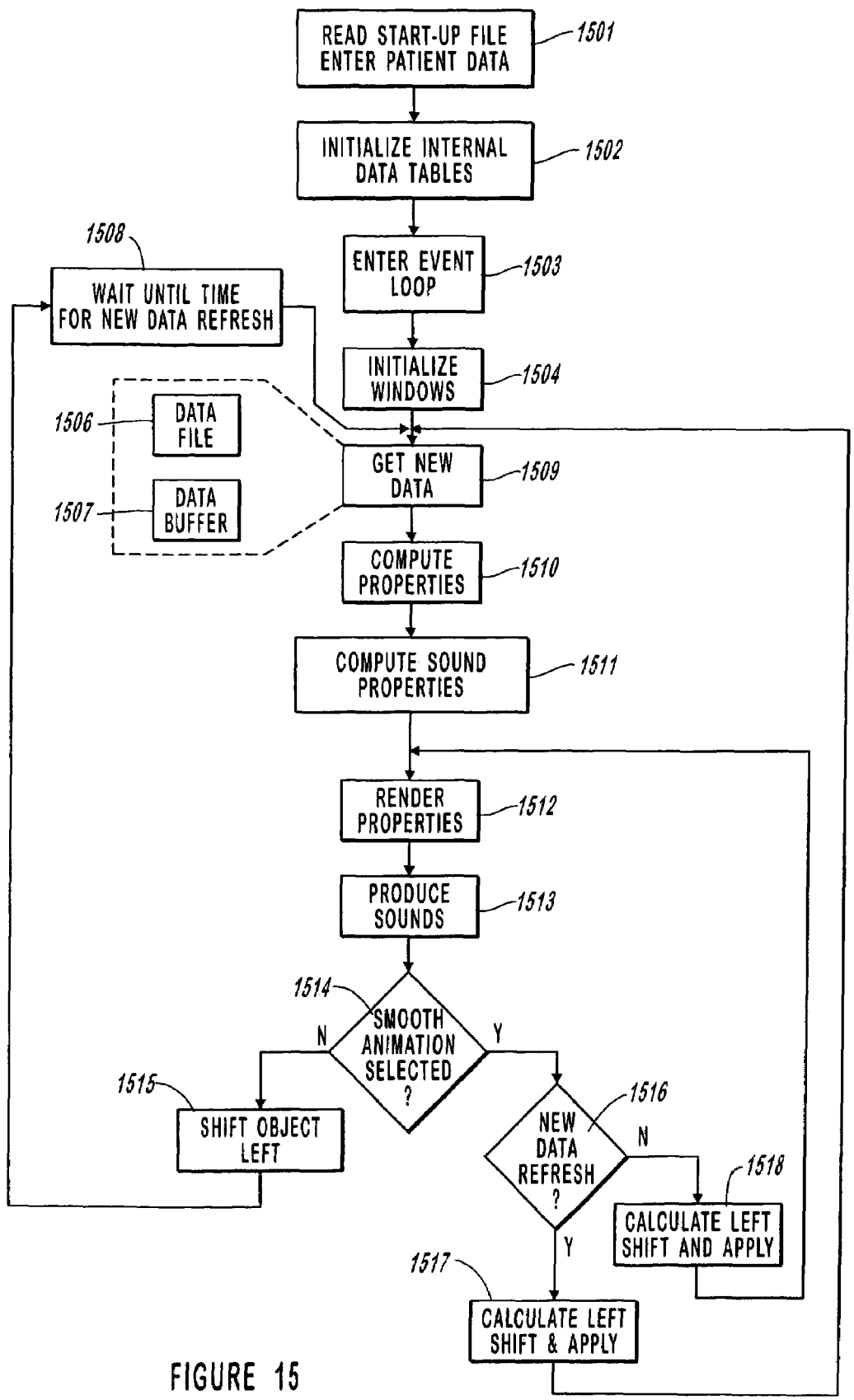
FIG. 15 is a software flow chart showing the logic steps of a preferred embodiment of the invention.

FIG. 15 is a software flow chart showing the logic steps of a preferred embodiment of the invention. The preferred embodiment of this invention begins by reading the startup file 1501, which contains the name of the window and the properties associated with the invention. The properties associated with the a window include formulas to set object properties, text that is to be rendered in the scene, the initial size of the window, the initial rotation in each window, zoom, lighting and patient data that describes the normal state of each variable. Internal data tables are next initialized 1502. For each new window encountered in the startup file a new window object is made and this window object is appended to the list of windows. The window object contains an uninitialized list of properties describing the state of the window, which is filled with data from the startup file. The event loop is entered 1503. This is a window system dependent infinite loop from which the program does not exit. After some initialization, the program waits for user input and then acts on this input. The program then takes control of the event loop for continuous rendering that is if there is no interactivity in the program. Initialization 1504 of windows is next performed. This involves calls to the window system dependent functions (these are functions that are usually different on different computational platforms) that creates the windows and displays them on the computer screen. In the current preferred embodiment of the invention, OpenGL is required, although alternative embodiments using other 3D application programming interfaces, such as PEX or DirectX, could be substituted without departing from the concept of this invention. Also, in the preferred embodiment of this invention, a personal computer graphics card is preferred in the personal computer so as to permit smooth animation with multiple windows. The lack of such a card is not absolutely required for operation of this invention. New data is received 1509, typically from the data file 1506 or the data buffer 1507. This new data 1509 can come from any source that generates floating-point numbers. The preferred line of data is composed of columns of floating point numbers separated by space. At this point the current time is also stored so that the next line of data can be obtained at the next user defined time interval, which is typically set at about 1 second. Object properties are next computed 1510. This is performed by using formulas that are specified in the startup file to compute properties of objects. Data fields in the formulas are specified by writing the column number preceded by a dollar sign. For example, $1/20.0 would divide the first field by 20.0. The specific properties in this application are: cardiac object dimensions, material properties, and position. Material properties can include the red, green, and blue components as they appear under ambient, diffuse, and specular light, as well as transparency. The cardiac object position includes the y and z positions as well as an x shift. If four or more lines of data have been acquired, the respiratory object properties are computed. A delay is necessary because a cubic spline is fitted, using four data points to do the fit, to the data points to generate a smooth respiratory object. Therefore, until four time steps have passed, the curtain is not rendered. Thereafter, it is rendered every time new data is acquired. Cardiac object properties include material properties and the height of the color bands. Blood pressure object length and materials are the thin cylinders that go through the top and bottom of each ellipsoid. Next, reference grid properties are computed. All objects, except the cardiac object reference are stationary, in the current implementation. The cardiac object reference can move according to the movement of the cardiac object if the user specifies this movement in the startup file. Next, sounds are computed 1511 and made audible 1513. Objects and reference grids are rendered 1512. Before rotation the newest object appears at the right side of the screen and oldest object is at the left side of the screen. Sound is produced 1513 next. A test 1514 is next made to determine if smooth animation is selected. If smooth animation is selected the scene will scroll during the time the program is waiting to get new data. The program, using available computing resources, selects the minimum time increment so that the shift of the objects can be rendered within the increment, but limiting the increment to the smallest increment that human eyes can detect. If smooth animation is not selected, objects are shifted to the left 1515 such that the distance from the center of the newest cardiac object to that of the former cardiac object is equal to the inter-cardiac spacing. The process waits 1508 until the current time minus the time since data was last obtained equals the data acquisition period specified by the user. If the current time minus the time when the data was last acquired equals the user specified data acquisition period then a new line of data is acquired. If smooth animation is selected, then the cardiac objects are shifted to the left by computing 1516 to that when it is time to get the next line of data, the cardiac objects have moved 1517, 1518 such that the distance from the rightmost cardiac object to the position where the new cardiac object will appear is equal to the inter-cardiac-object distance. For example, if it takes 0.20 seconds to render the previous scene, the period of data acquisition is 1.0 seconds, and the x shift of the rightmost cardiac object is 0.1 units then the program will shift the scene left (0.20/(1.0+0.20)*(1.0 0.1)=0.15. The formula in the denominator is (1.0+0.20 instead of 0.8 because, if the scene has been shifted left such that, when new data is acquired, the shifting has stopped (because the position of the cardiac objects satisfies the criteria that the distance from the center of the rightmost cardiac object to the center point where the new cardiac object will be rendered=1 unit) then the animation will no longer be smooth, that is, when new data is acquired the animation will appear to stop. Note, that the respiratory object is never entirely smoothly shifted because no data is available to render the object at the intermediate time steps.

Figure 16:
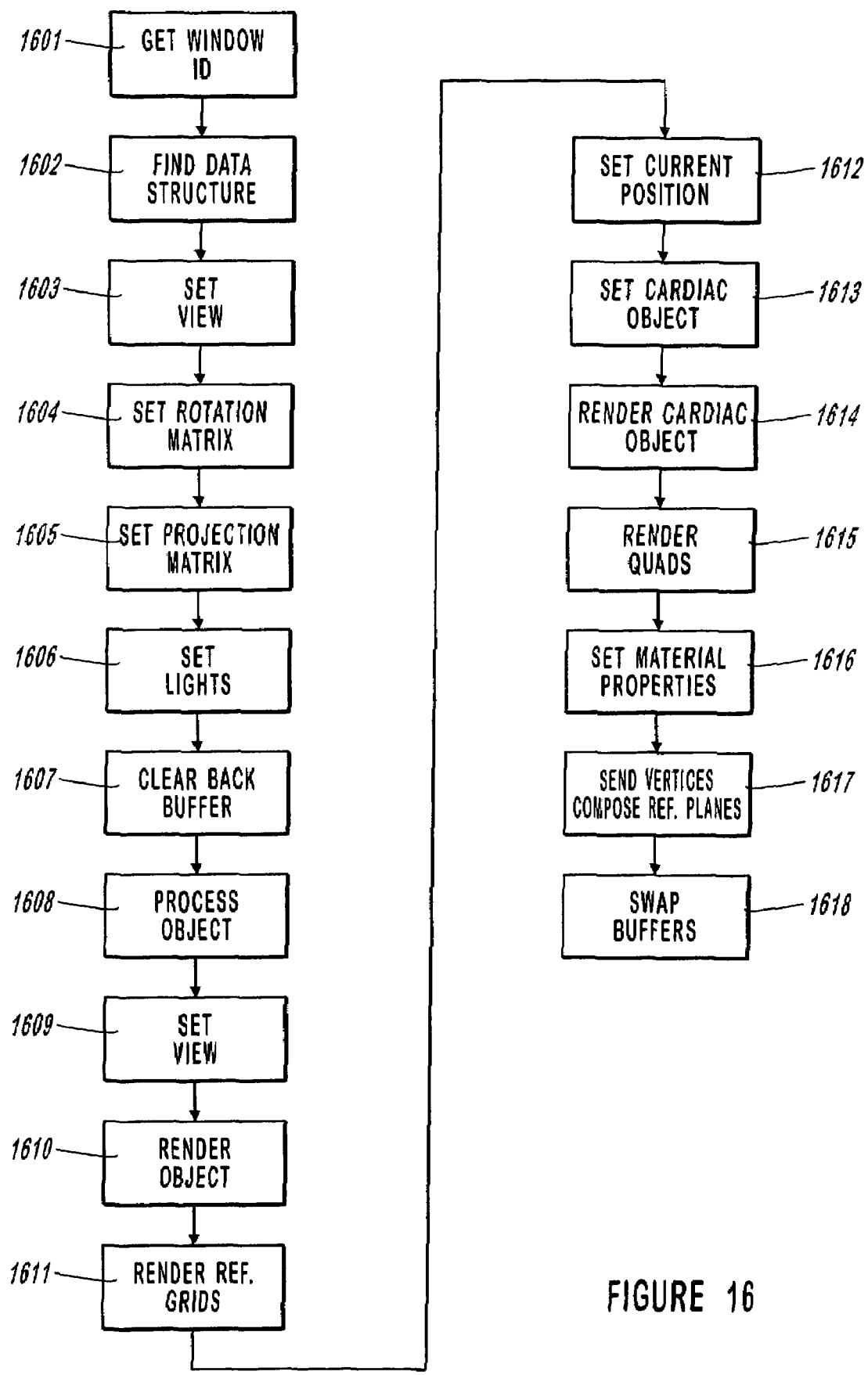
FIG. 16 is a software block diagram showing the logic steps of the image computation and rendering process of a preferred embodiment of the invention.

FIG. 16 is a software block diagram showing the logic steps of the image computation and rendering process of a preferred embodiment of the invention. This process begins with acquiring the window identification 1601 of the current rendering context. Next, the data structure is found 1602 corresponding to the current window identification. After which, the view is set 1603. A rotation matrix is set 1604. A projection matrix is set 1605. Lights are set 1606. The back buffer is cleared 1607. Object processing 1608 begins, and includes for each cardiac object, calling OpenGL to see material properties; shift left one inter-cardiac-object distance; push the modelview matrix, shift x,y, and z directions; call OpenGL utility toolkit to render the cardiac object; set the top cardiac object material properties, call OpenGL quadries function to render top cardiac object; set top cardiac object material properties, call OpenGL quadrics function to render bottom cardiac object and pop modelview matrix. Next, the view is set 1609, as above. The respiratory object is rendered 1610, by setting OpenGL to render quad strips, for each polygon strip set material properties, and send vertex to OpenGL. Reference grids are rendered 1611 by setting material property of the cardiac reference grid. The current position is set 1612 to be the ideal position of the newest cardiac object, that is the position corresponding to a patient in ideal health. The cardiac object material properties are set 1613. The OpenGL utility toolkit is called to render 1614 the cardiac object. Next, OpenGL is set to render quads 1615. After which the material properties of the reference planes are set 1616. Vertices that compose the reference planes through the OpenGL pipeline are sent 1617 and buffers are swapped 1618. Buffer swap is a window system defendant function.

Figure 17:
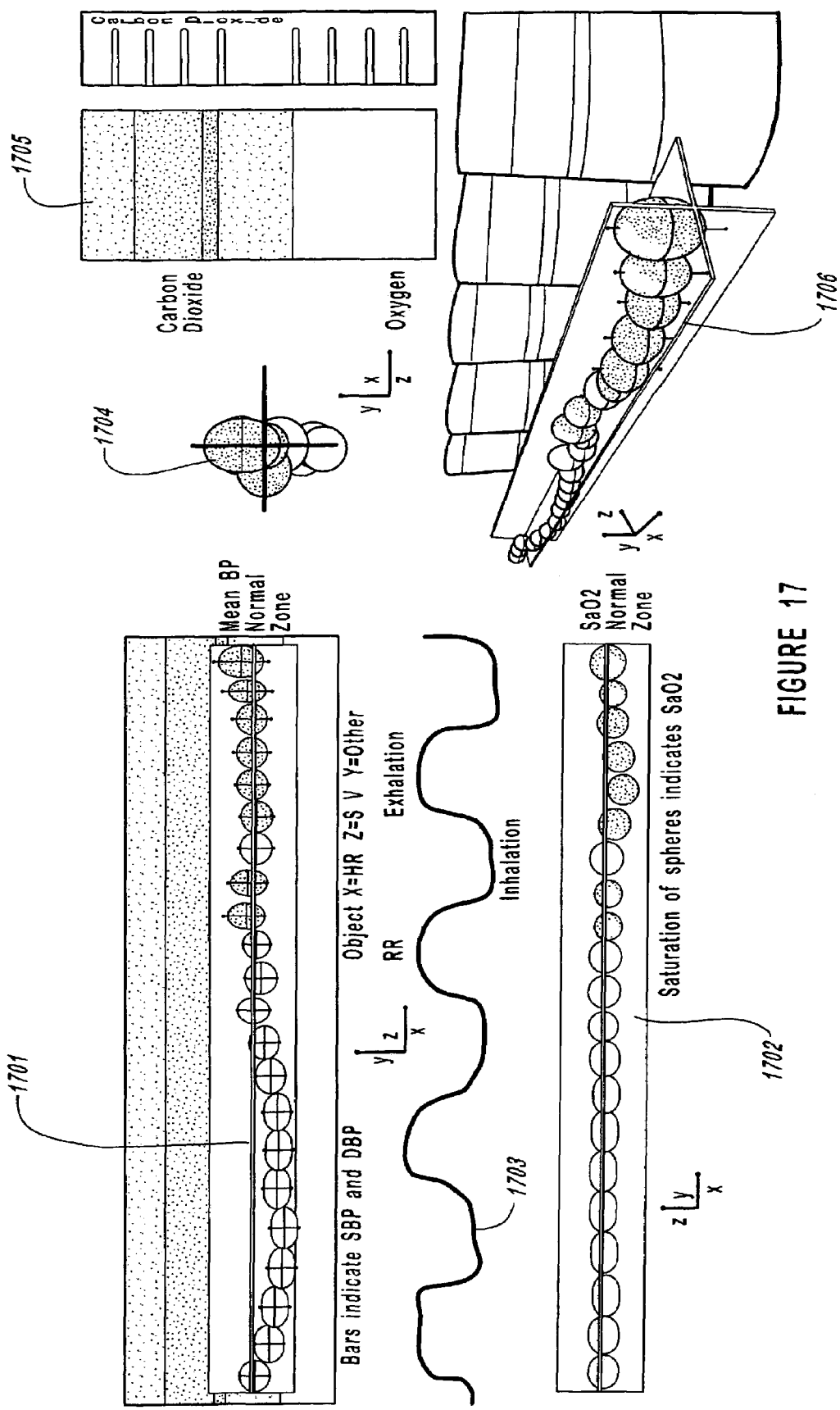
FIG. 17 is a photograph of the 3-dimensional display of a preferred embodiment of the invention.

FIG. 17 is a photograph of the 3-dimensional display of a preferred embodiment of the invention. The 3-D view shown at lower right 1706 provides a comprehensive, integrated and interactive view of all physiological data, and shows the interaction between the different objects in relation to the reference frame. This view can be manipulated by the user to fit specific application needs. The front 1701, side 1704, 1705 and top views 1702 show how the same data appears from different vantage points. In this figure these views 1701, 1702, 1704, 1705 show the interaction between the cardiac object, the reference frame and the respiratory object, with the side view 1704 providing a target for optimum efficiency of the cardiac system 1705 shows the level of gas concentration in the lungs and overall tidal volume in the respiratory system. This FIG. 17 is a representation of a true 3-D model of the physiologic data. The circle 1703 shown is the top view of the respiratory waveform showing CO2 content in the lungs and inspiration and expiration values. In 1703, a real time display, the object grows and shrinks with each heartbeat. Its height is proportional to the heart's volume output and its width is proportional to heart rate. The gridframe (or reference framework) shows the expected normal values for stroke volume and heart rate. The position of this object in the vertical direction of the display is proportional to the patient's mean blood pressure. This graphic objects shape and animation provides a useful graphical similarity to a working heart. In the preferred embodiment, the background is colored to show inspired and expired gases. The height of the "curtain" is proportional to tidal volume, while the width is proportional to respiratory rate. The colors, which are, displayed in the preferred display show the concentrations of respiratory gases. Time is set to move from right to left, with the present or current conditions shown at the "front" or right edge of each view. Past states remain to provide a historical view of the data.

Figure 18:
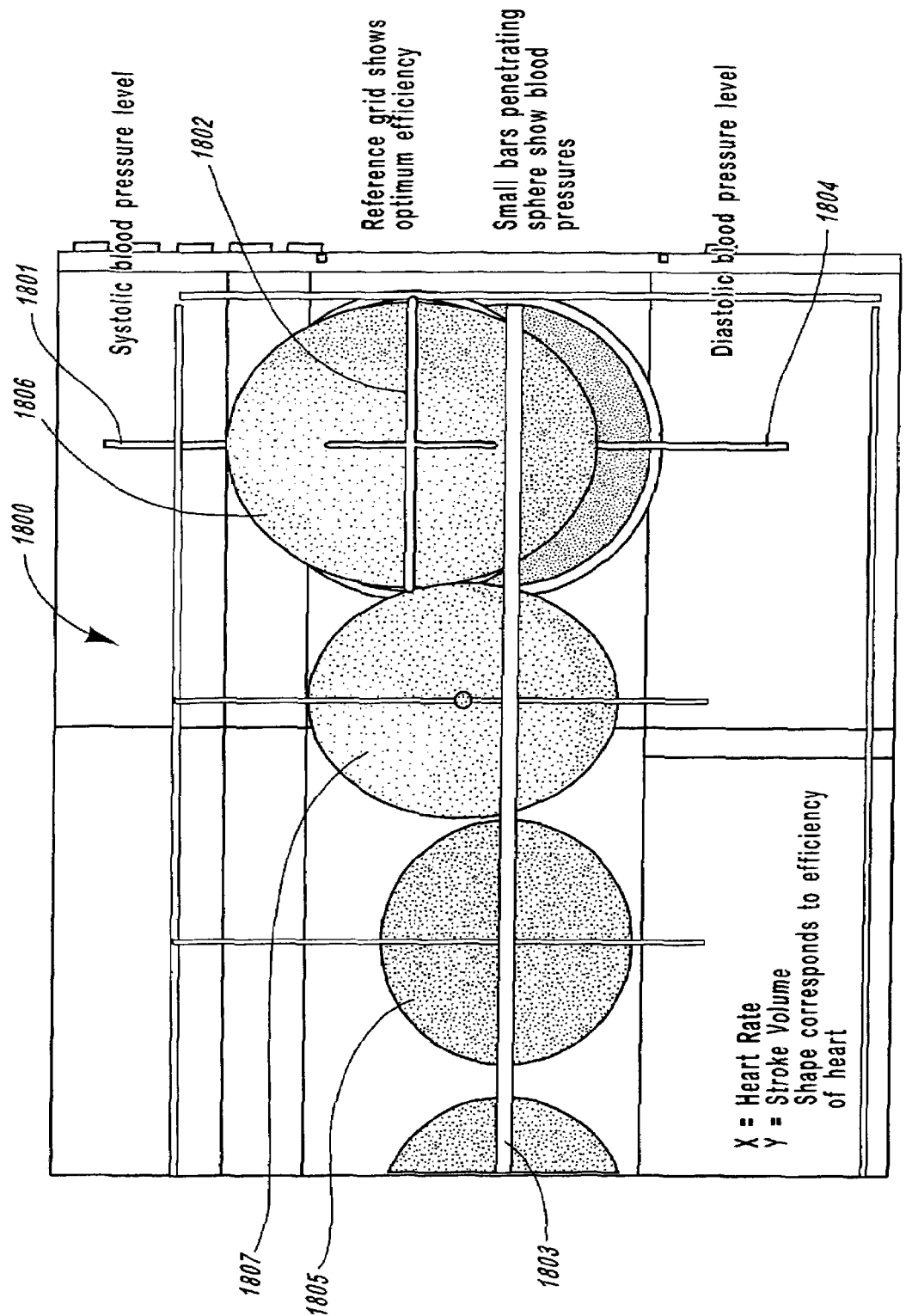
FIG. 18 is a close-up front view of the cardiac object and the associated reference grid of a preferred embodiment of the invention.

FIG. 18 is a close-up front view of the cardiac object and the associated reference framework of a preferred embodiment of the invention. The upper limit of normal blood pressure value is shown 1800 on the reference frame. The systolic blood pressure level is indicated by the bar 1801 penetrating the cardiac sphere 1806. The height 1802 of the sphere 1806 is proportional to cardiac output, which shows the optimum efficiency of the heart. The width of the sphere 1806 is proportional to 1/heart rate. The elevation of the sphere 1806 is an indication of mean blood pressure, where the center reference gridline is a normal mean blood pressure 1803. The lower limit, or diastolic blood pressure 1804 is shown by the length of the bar extending downward from the sphere 1806. Previous historical values for the sphere 1806 are also provided in 1805, 1807.

Figure 19:
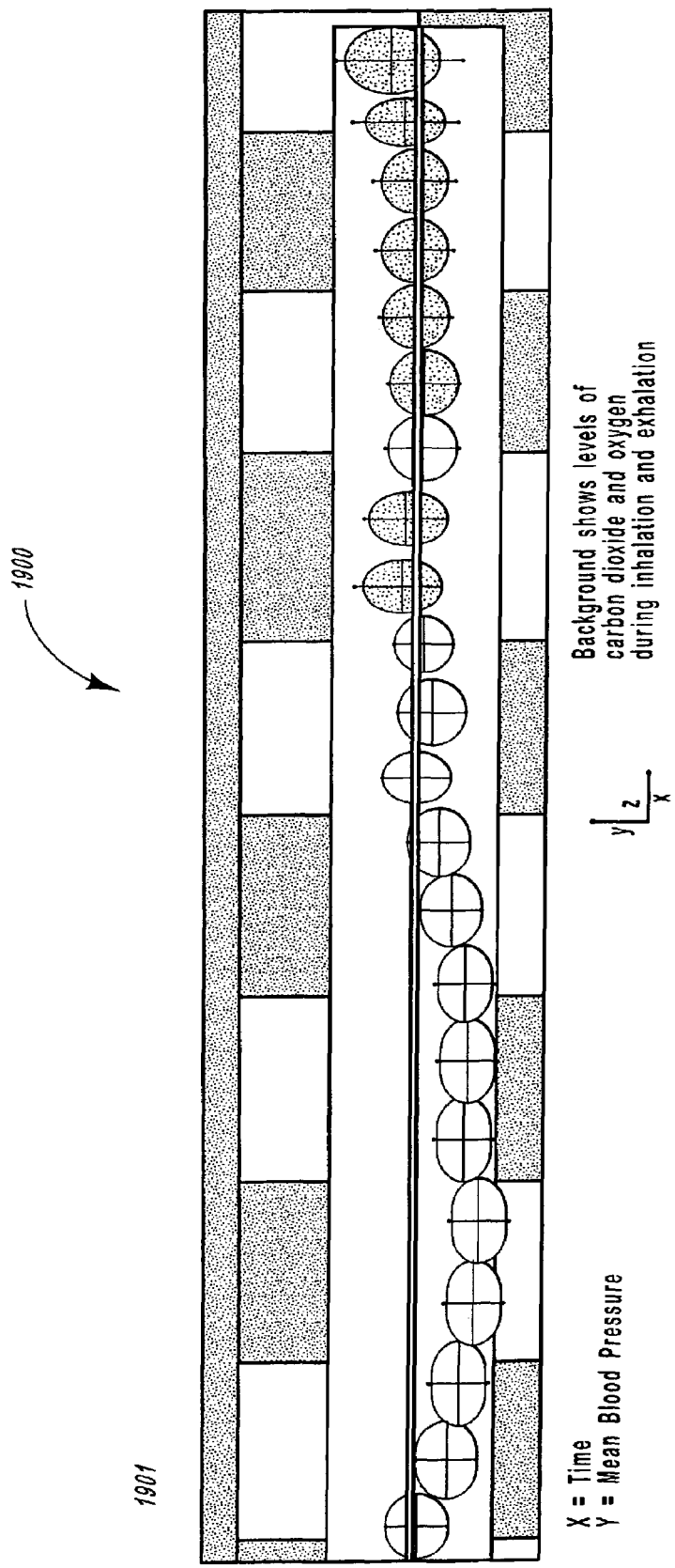
FIG. 19 is a view of the front view portion of the display of a preferred embodiment of the present invention showing the cardiac object in the foreground and the respiratory object in the background.

FIG. 19 is a view of the front view portion of the display of a preferred embodiment of the present invention showing the cardiac object in the foreground and the respiratory object in the background. This view 1900 provides a more quantitative image of the hemodynamic variables, stroke volume, blood pressure 1901 and heart rate. The "normal" reference lines are more apparent. In the preferred embodiment, respiration is shown by changes in the background color.

Figure 20:
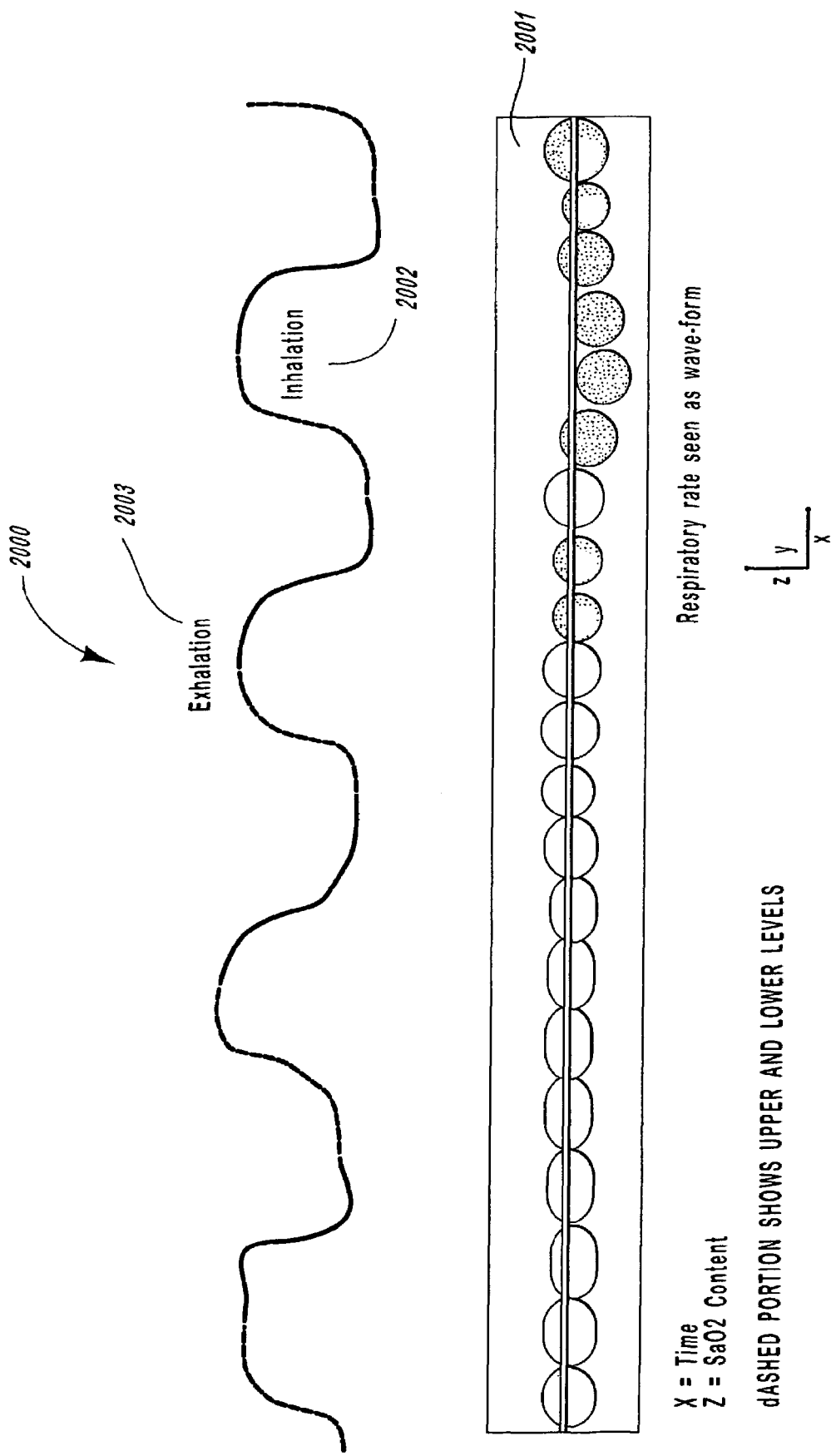
FIG. 20 is a view of the top view portion of the display of a preferred embodiment of the present invention showing the cardiac object toward the bottom of the view and the respiratory object toward the top of the view.

FIG. 20 is a view of the top view portion of the display 2000 of a preferred embodiment of the present invention showing the cardiac object toward the bottom of the view and the respiratory object toward the top of the view. Inhaled gas 2002 and exhaled gas 2003. CO2 concentrations and oxygen saturation of the arterial blood 2001 versus time are also shown.

Figure 21:
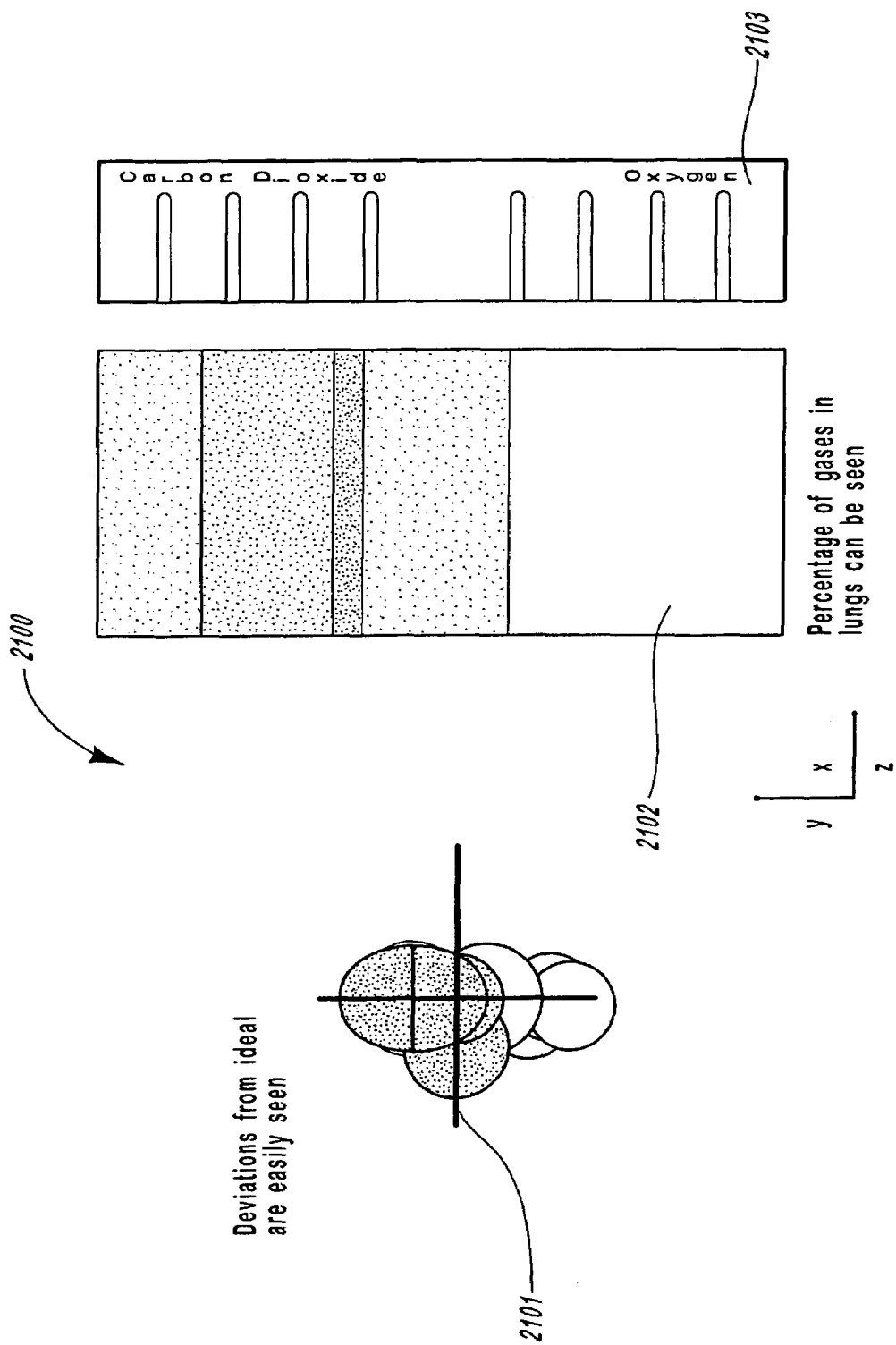
FIG. 21 is a view of the side view portion of the display of a preferred embodiment of the present invention showing the cardiac object to the left and the respiratory object to the right.

FIG. 21 is a view of the side view portion of the display of a preferred embodiment of the present invention showing the cardiac object to the left and the respiratory object to the right. Gas concentration in the lungs 2101, a calibrated scale for gas concentration 2103, blood pressure 2100, and oxygen saturation 2101 are shown. The end view, shown here in FIG. 21, is especially useful during treatment, where the goal is to bring the variables back to the center or normal state. Functional relationships can be added to this view to predict how treatment can be expected to bring the variables back to normal.

Figure 22:
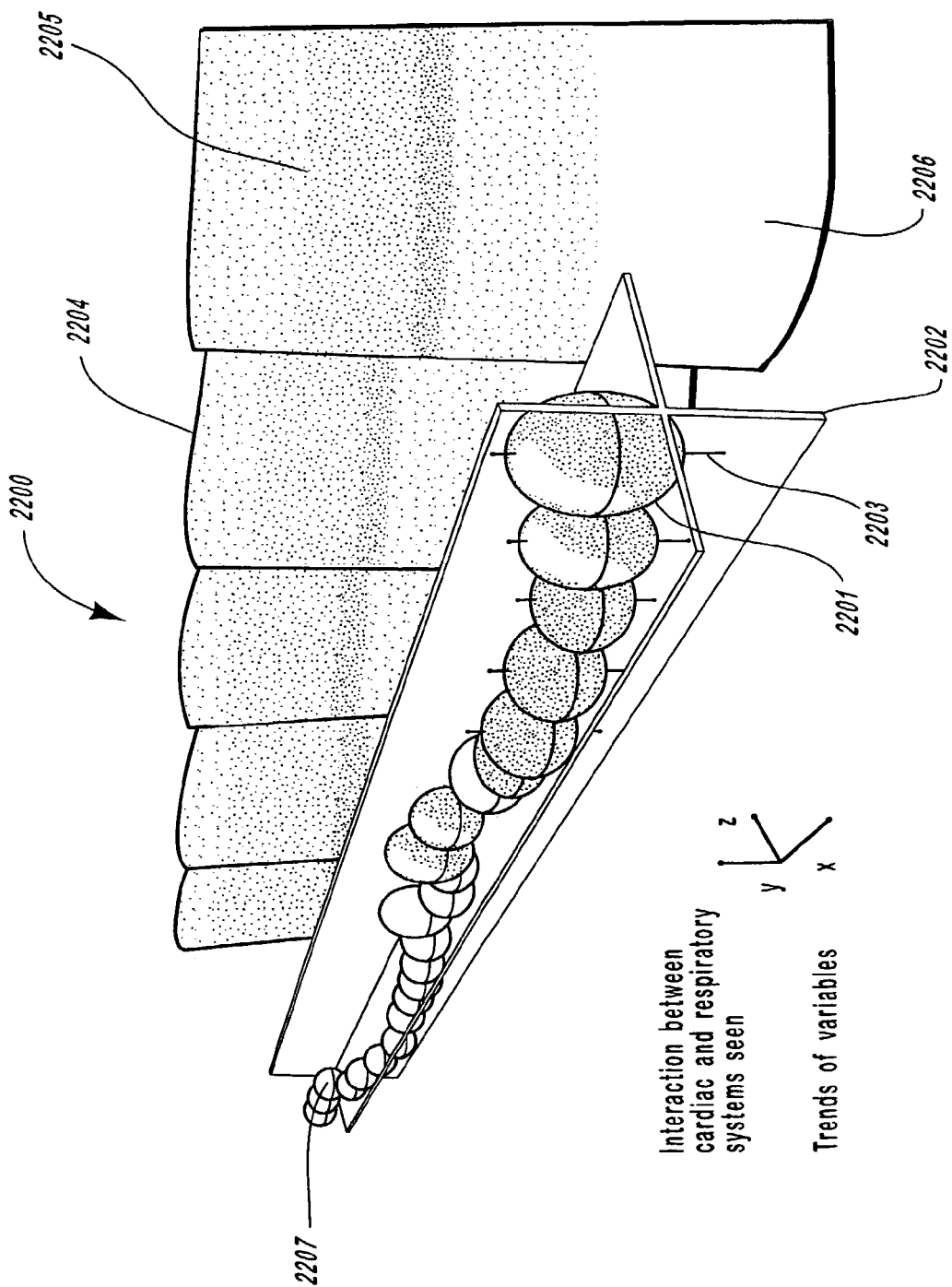
FIG. 22 is a view of the 3-D perspective view portion of the display of a preferred embodiment of the invention showing the cardiac object in the left foreground and the respiratory object in the right background.

FIG. 22 is a view of the 3-D perspective view portion of the display of a preferred embodiment of the present invention showing the cardiac object in the left foreground and the respiratory object in the right background. This view 2200 provides a comprehensive, integrated and interactive view of nine physiological variables. The sphere 2201 grows and shrinks with each heartbeat. Its height is proportional to the heart's stroke volume and its width is proportional to heart rate. This graphic object 2201 offers useful similarity to a beating heart. The gridframe 2202 shows the expected normal values for stroke volume and heart rate. The position of this object 2201 on the screen is proportional to the patient's mean blood pressure. The ends of the bar 2203 drawn vertically through the center of the heart object show systolic and diastolic blood pressure. In the preferred embodiment of the invention, the background 2204 is colored to show inspired and expired gases. The height of the "curtain" 2205 is proportional to tidal volume. The width of each fold 2206 is proportional to respiratory rate. In the preferred embodiment colors are used to show the concentrations of respiratory gases. Time moves from right to left with the present condition shown at the "front" or right edge of the view 2200. Past states 2207 remain to permit a historical view of the data.

Figure 23:
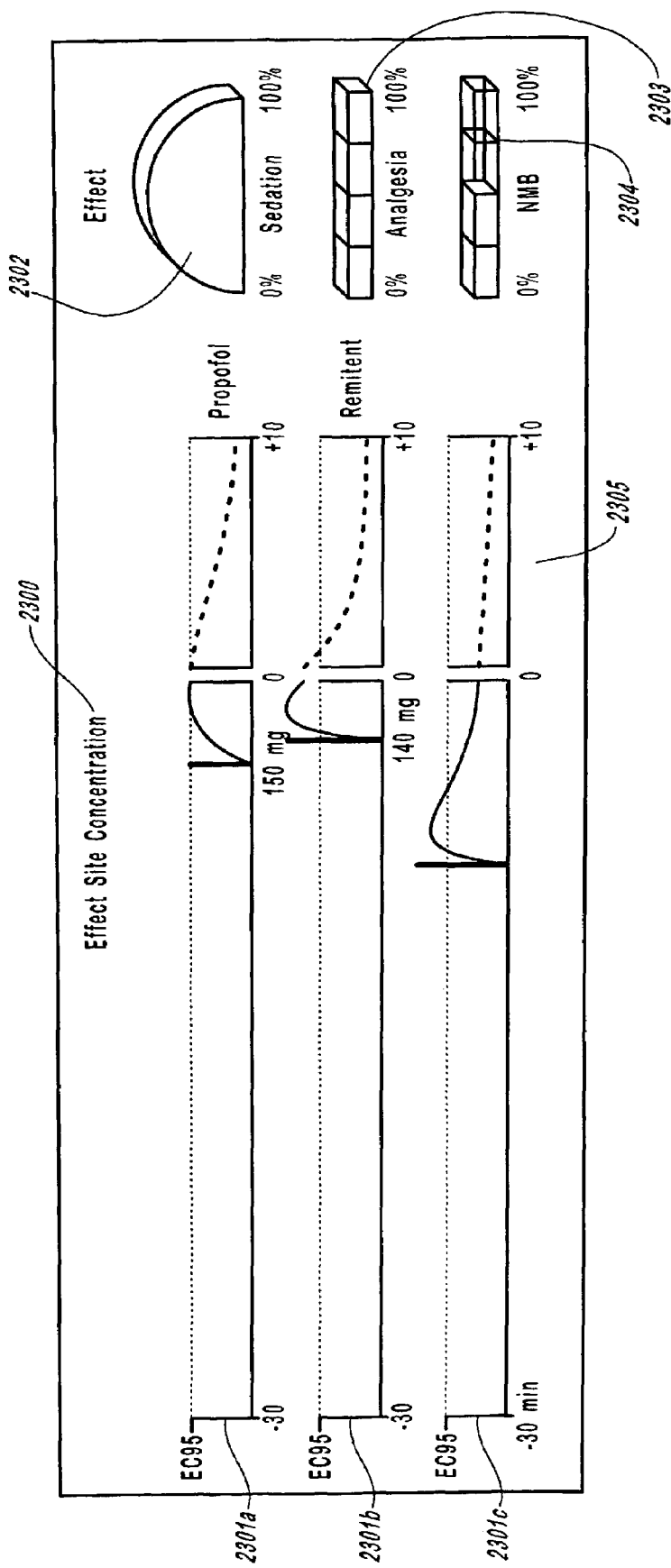
FIG. 23 is a view of an example of the preferred display of the drug effects shown in this invention.

FIG. 23 is a view of an example of the preferred display 2300 of the drug effects shown in this invention. Concentration is shown by the plots 2301$a,b,c$. The concentration is also presented with respect to the classification of the anesthetic, sedatives 2302, analgesic 2303, and neuromuscular blocking agents 2304. In the preferred embodiment each drug is color-coded. Past, current and predicted concentrations are normalized with respect to the drug's EC95 value (the drug concentration at which 95% of the population is completely affected by the anesthetic drug) and plotted relative to the time 2305 that it was administered. The current drug effects are represented as a 3-dimensional bar or pie charts 2302, 2303, 2304. The effects are presented proportionally to the extent that the objects 2302, 2303, 2304 are filled.

Figure 24:
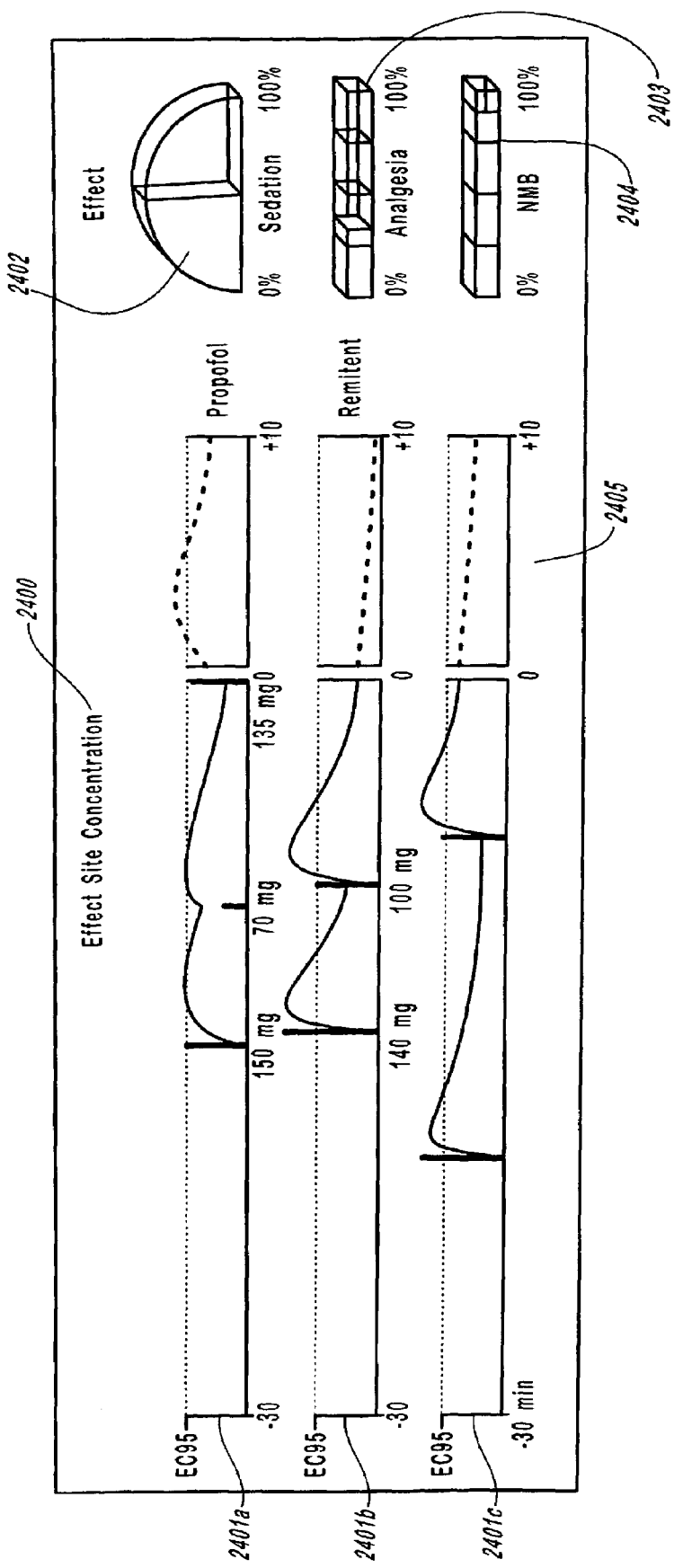
FIG. 24 is a view of a second example of the preferred display of the drug effects shown in this invention.

FIG. 24 is a view of a second example of the preferred display 2400 of the drug effects shown in this invention. The plots 2401$a,b,c$ are shown displaying effect site drug concentration. The pie chart 2402 shows the sedation effect. The bar chart 2403 shows the analgesia effect. The bar chart 2404 shows the muscle relaxant effect. This data is plotted against time 2405.

Figure 25:
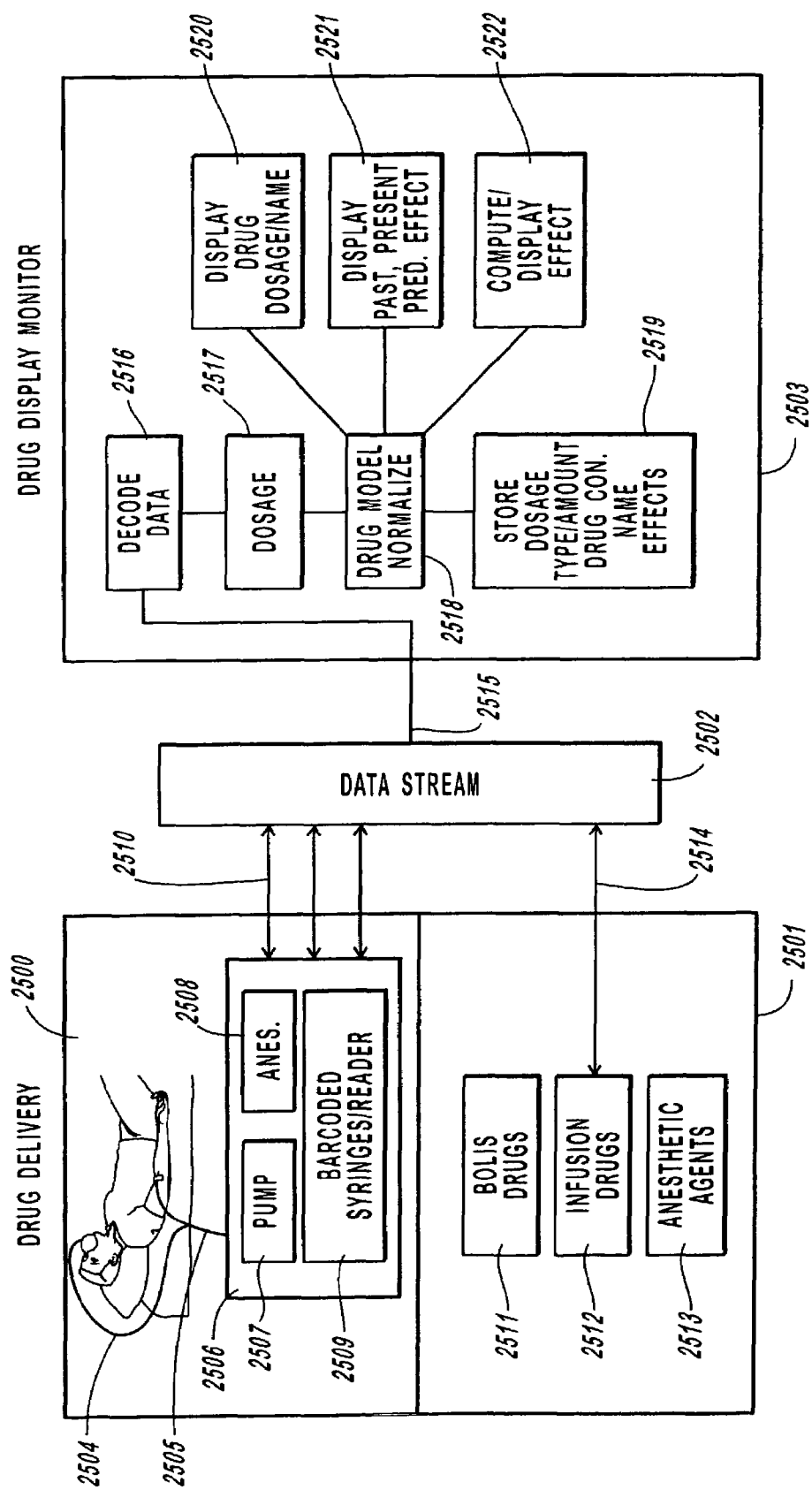
FIG. 25 is a system flow process flow diagram of the preferred embodiment of this invention.

FIG. 25 is a system flow process flow diagram of the preferred embodiment of this invention. A drug delivery system 2500 communicates through a data stream 2502 to a drug display monitor device 2503. The patient 2504 is shown receiving anesthetic drugs 2505 from a drug delivery system 2506. The preferred drug delivery system 2506 includes an infusion pump 2507, an anesthesia machine 2508 and/or a set of bar coded syringes and a bar code reader. A simulator program or process 2501 is provided for testing purposes and is designed to simulate boles (injection) drugs 2511, infusion drugs 2512, and anesthetic agents 2513. The drug delivery system 2506 communicates with the data stream 2502 via multiple data channels 2510. In the present preferred embodiment of the invention, the multiple data channels may include a TCP/IP socket, a serial RS-232 interface, and/or a serial RS-495 USB interface. Other alternative communication channels can be substituted without departing from the concept of this invention. The preferred interface 2514 between the simulator 2501 and the data stream 2502 is a UDP socket, although alternative communication interfaces can be substituted without departing from the concept of this invention. The data stream 2502 provides a data path 2515 to the drug display monitor system 2503. Included in the drug display monitor system is a decode data function 2516 that receives the data stream 2502. A dosage or infusion rate calculator 2517 receives the decoded data. A drug modeler/normalizer 2518 receives the dosage and/or infusion rate data and proceeds to store 2519 the dosage type, dosage rate, drug concentration, drug type, the concentration effect, and the site concentration effect. The drug modeler/normalizer 2518 provides the appropriate data to a first display function 2520 for showing drug dosage or rate and drug name, to a second display function 2521 for showing past, present, and predicted site concentration effects, and to a third display effect computer function 2522.

Figure 26:
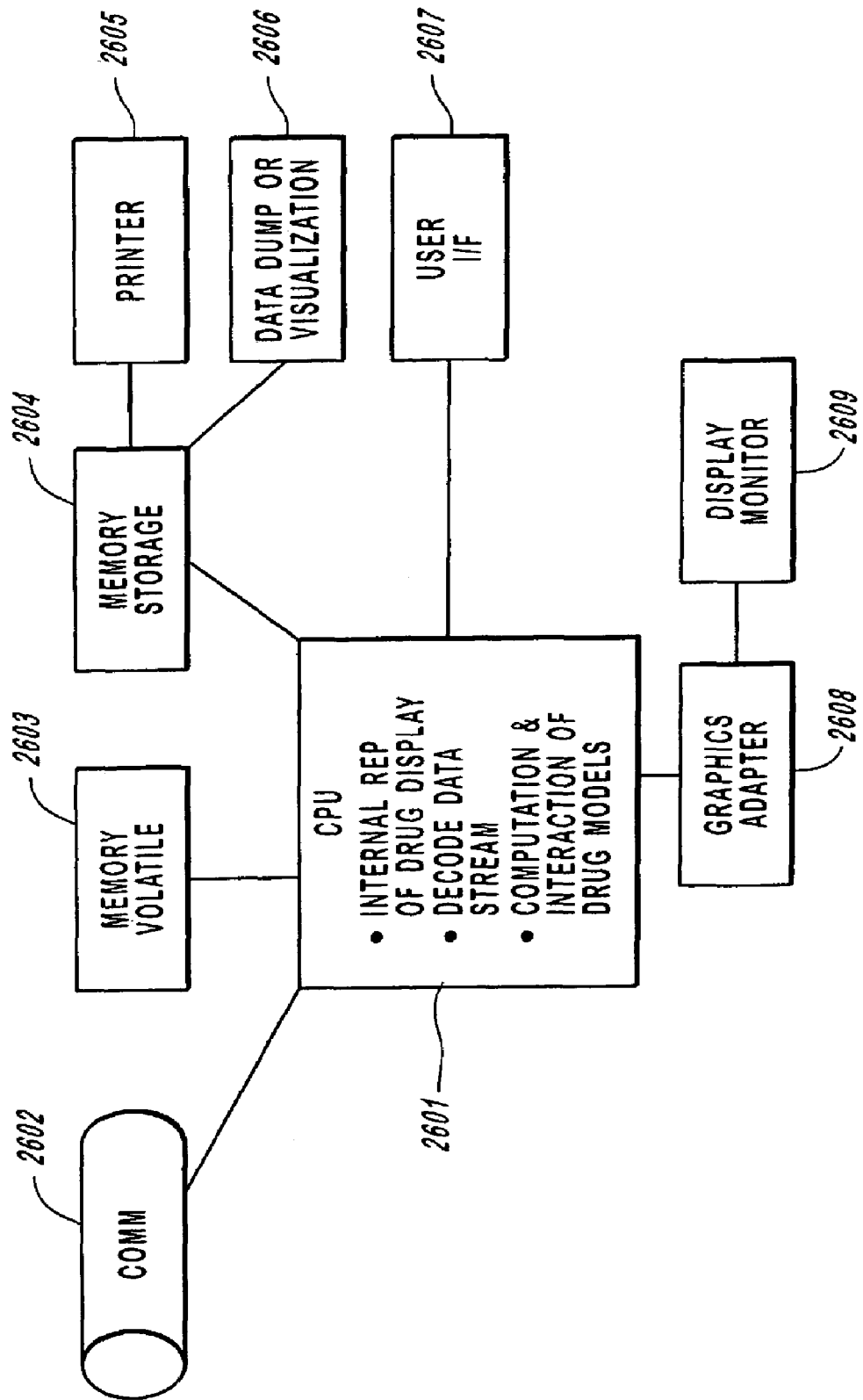
FIG. 26 is a preferred hardware/communication diagram of the preferred embodiment of this invention.

FIG. 26 is a preferred hardware/communication diagram of the preferred embodiment of this invention. A central processing unit (CPU or processor) 2601 is provided to execute the process of this invention, specifically to produce the internal representation of the drug display, to decode the data stream, and to compute the interaction between drug models. The processor 2601 communicates with the data stream 2502 via a communication channel 2602. The communication channel 2602 can be a serial, parallel or socket type channel. The processor 2601 is electrically connected to volatile memory 2603 for the dynamic storage of variables. The processor 2601 is also electrically connected to a static memory device (such as static RAM, disk drives or the like) 2604 for the storage of drug delivery data and trends. A user interface 2607 is connected to the processor 2601 to enable user interaction. The typical user interface 2607 is a keyboard, mouse, touchscreen or the like. A graphics adapter 2608 is in communication with the processor 2601 for preparing data for rendering on a standard display 2609. The typical standard display 2609 is a monitor, an LCD device or the like. A hardcopy printer 2605 and a data dump visualization device 2606 is also provided, typically in communication with the processor 2601 through the memory 2604.

Figure 27:
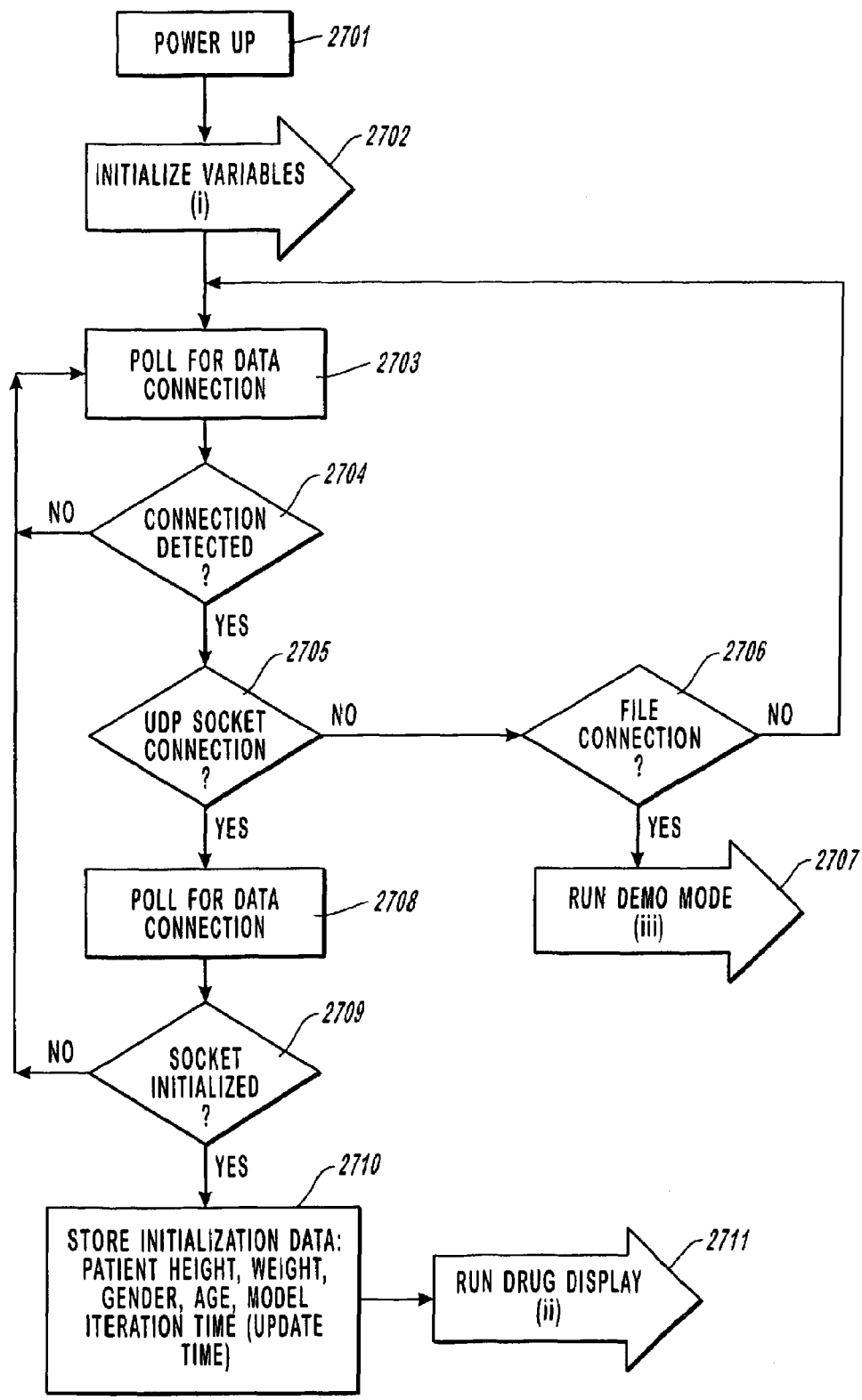
FIG. 27 is a top-level flow chart of the preferred drug monitoring process of this invention.

FIG. 27 is a top-level flow chart of the preferred drug monitoring process of this invention. Initially, the system is powered up 2701. Variables are initialized 2702. Additional detail on the variable initialization 2702 is provided in FIG. 28. Polling 2703 for data collection is performed 2703. A test 2704 is made to determine if a connection has been detected. If no connection is detected the process returns to the polling 2703 for data connection. If a connection is detected, a test 2705 is made to determine if a UDP socket connection exists. If no UDP socket connection exists, then a test 2706 is made to determine if a file connection has been made. If no file connection has been made, polling 2703 for data connection continues. If a file connection has been made, then a demo mode is run 2707. Additional detail on the demo mode is described with respect to FIG. 30. If a UDP socket connection exists, then the socket header is decoded 2708. A test 2709 is then made to determine if the socket has been initialized. If the socket has not been initialized, the process continues polling 2703 for data connection. If the socket has been initialized 2709, then initialization data is stored 2710. This initialization data includes, but may not be limited to, patient height, weight, gender, age, model iteration time or update rate and the like. After storing 2710 the data, the drug display function is run 2711 or executed. Additional detail on the run drug display step 2711 is provided below with respect to FIG. 29.

Figure 28:
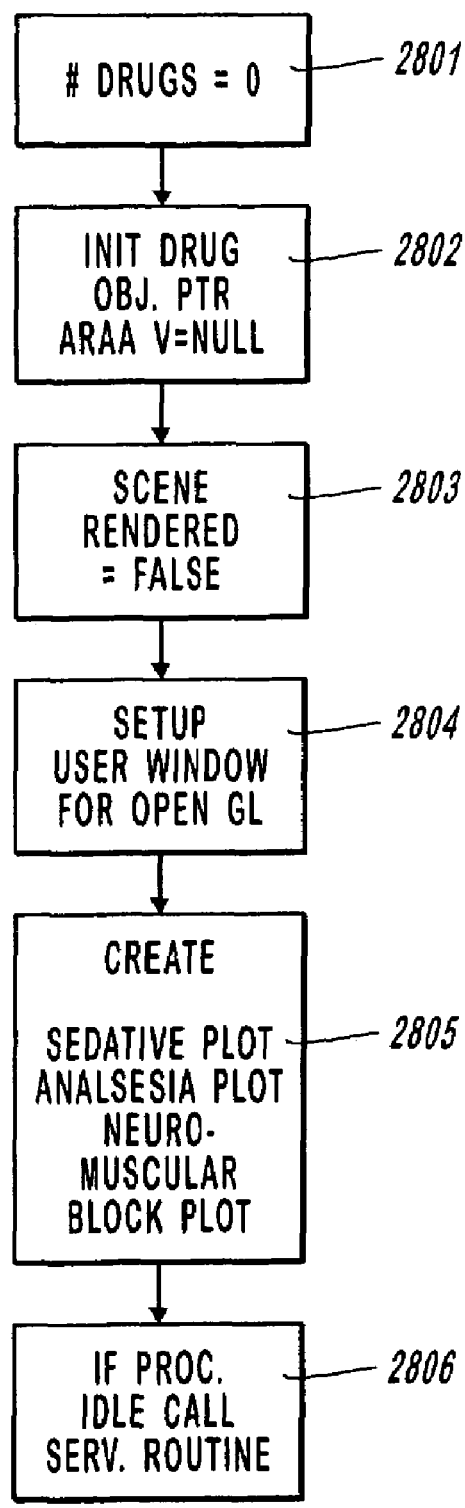
FIG. 28 is a detailed flow chart of the initialize variables section of the preferred drug monitoring process of this invention.

FIG. 28 is a detailed flow chart of the initialize variables section 2702 of the preferred drug monitoring process of this invention. Initially, the number of drugs is set 2901 to zero. The drug object pointer array is initialized 2802 to NULL. The scene rendered flag is set 2803 to false. The user window is setup 2804 for OpenGL. Next, a sedative plot, analgesia plot and a neuromuscular block plot are created 2805. A test 2806 is then made to determine if the processes is idle, if so the IdleLoop service routine is called. Additional detail on the IdleLoop service routine is discussed below and shown in FIG. 31.

Figure 29:
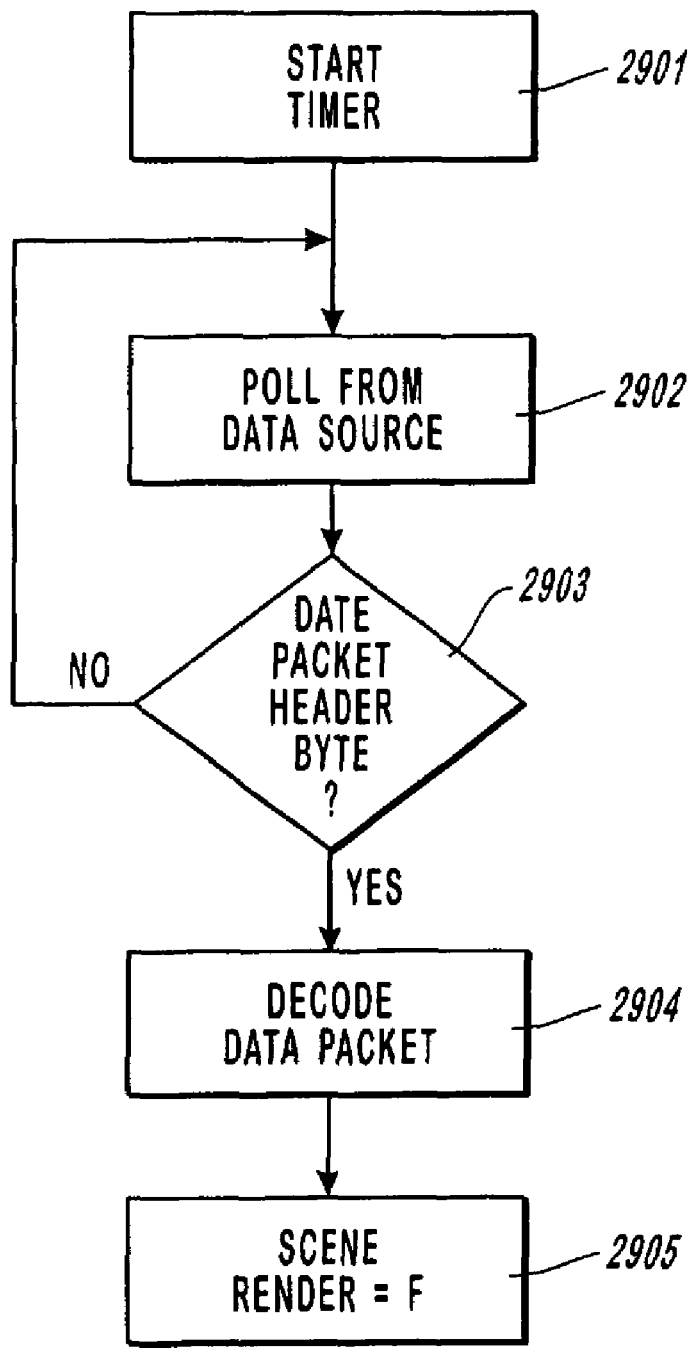
FIG. 29 is a detailed flow chart of the run drug display section of the preferred drug monitoring process of this invention.

FIG. 29 is a detailed flow chart of the run drug display section 2711 of the preferred drug monitoring process of this invention. First, a timer is started 2901. This enables the timer interrupt routine to be called at intervals of "update time." Additional detail on the timer interrupt is provided below in association with FIG. 37. Next, the data source is polled 2902. A test 2903 is made to determine if a data packet header byte has been found. If not, the polling 2902 continues. If a data packet header byte is found, the data packet is decoded 2904 and the scene render flag is set 2905 to false. Additional detail on the data decoder step 2904 is provided below with respect to FIG. 35.

Figure 30:
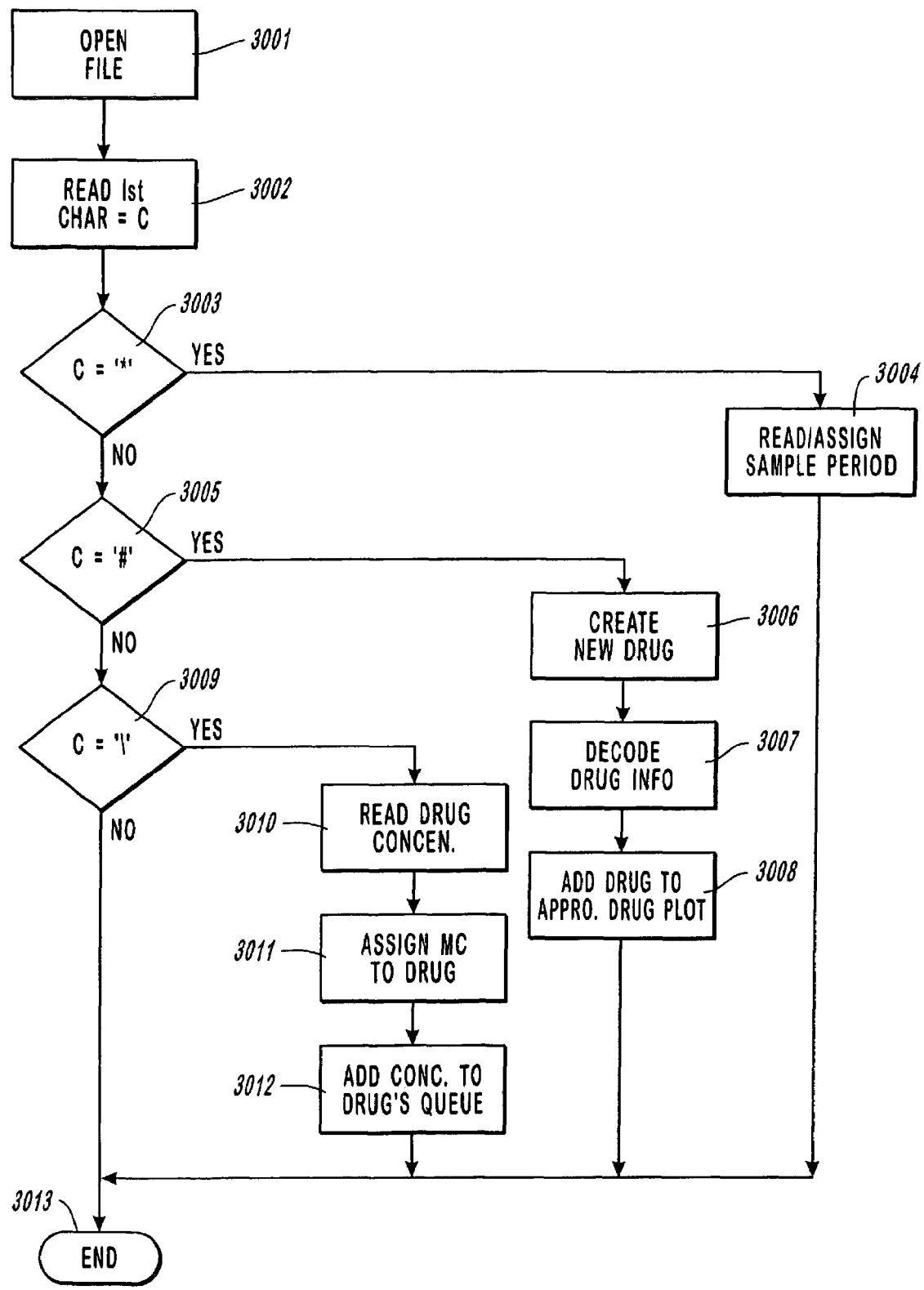
FIG. 30 is a detailed flow chart of the run demo mode section of the preferred drug monitoring process of this invention.

FIG. 30 is a detailed flow chart of the run demo mode section 2707 of the preferred drug monitoring process of this invention. The file is opened 3001. The first character ("C") is read 3002. A test 3003 is made to determine if C="*". If C="*" then the file is read and assigned 3004*a* sample period. Following the reading and assignment 3004 this section ends 3013. If C is not equal to "*", then a test 3005 is made to determine if C="#". If C="#", then a new drug record is created 3006, the new drug information is decoded 3007, and the new drug is added 3008 to the appropriate drug plot, after which this section of the process ends 3013. If C is not equal to "#", then a test 3009 is made to determine if C="\". If C="\", then the drug concentration is read 3010, the drug concentration is assigned 3011, and the concentration is added 3012 to the drug queue, after which this section ends 3013. If C is not equal to "\", this section of the process ends 3013.

Figure 31:
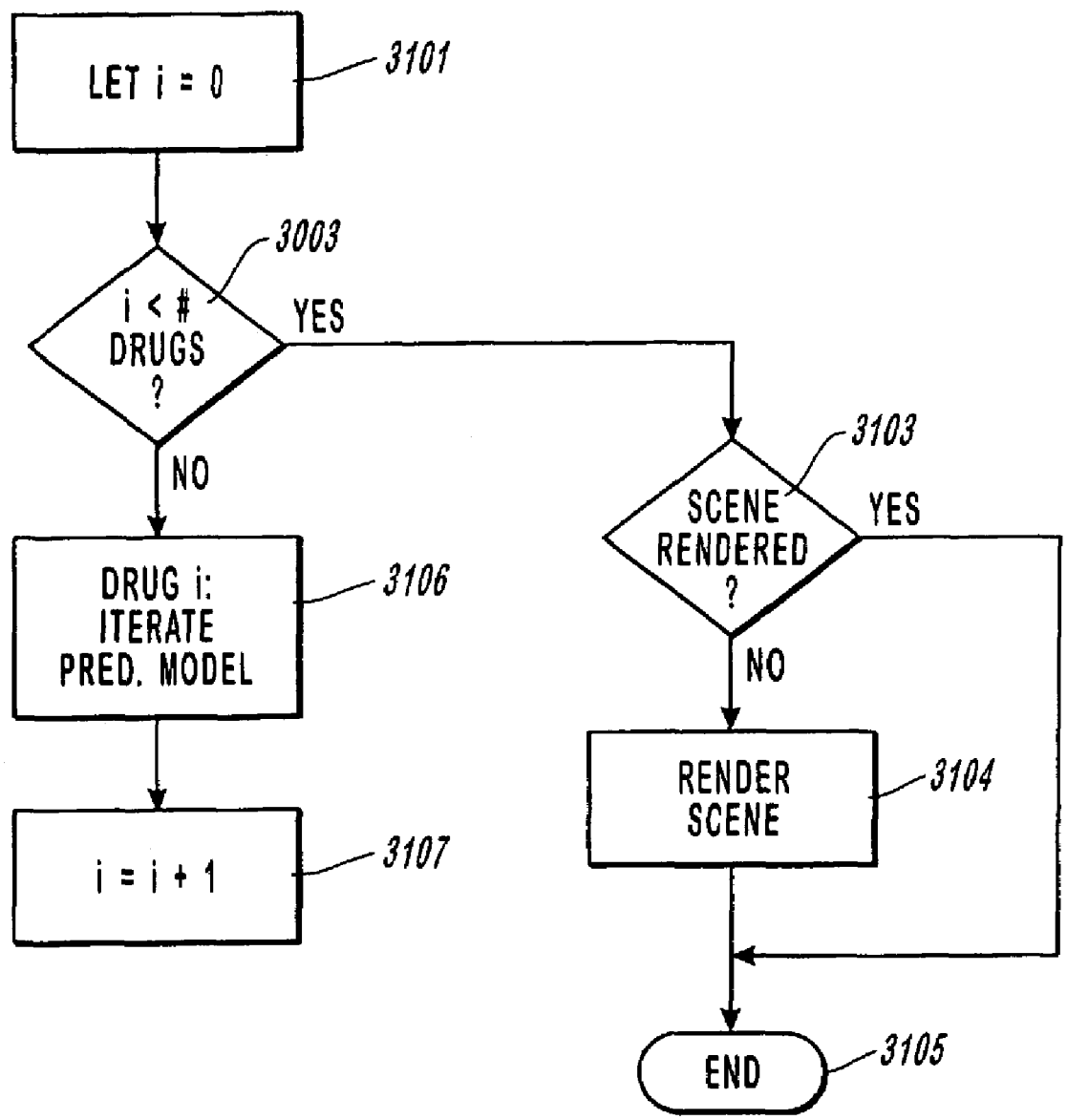
FIG. 31 is a detailed flow chart of the idle loop section of the preferred drug monitoring process of this invention.

FIG. 31 is a detailed flow chart of the idle loop section, of FIG. 28 step 2806, of the preferred drug monitoring process of this invention. First, I is set 3101 to zero. A test 3102 is made to determine if I is less than the number of drugs. If I is not less than the number of drugs, then a test 3103 is made to determine if the scene has been rendered. If the scene has been rendered, this section of the process ends 3105. If the scene has not been rendered, then the scene is rendered 3104. Additional detail on the scene-rendering step 3104, is discussed below, with respect to FIG. 32. If I is less than the number of drugs, then the drug value I is iterated 3106 for the predictive model. Additional detail on the predictive model 3106 process is discussed below with respect to FIG. 33. After the predictive model is iterated 3106, I is incremented 3107 by one, and the process returns to the test 3102.

Figure 32:
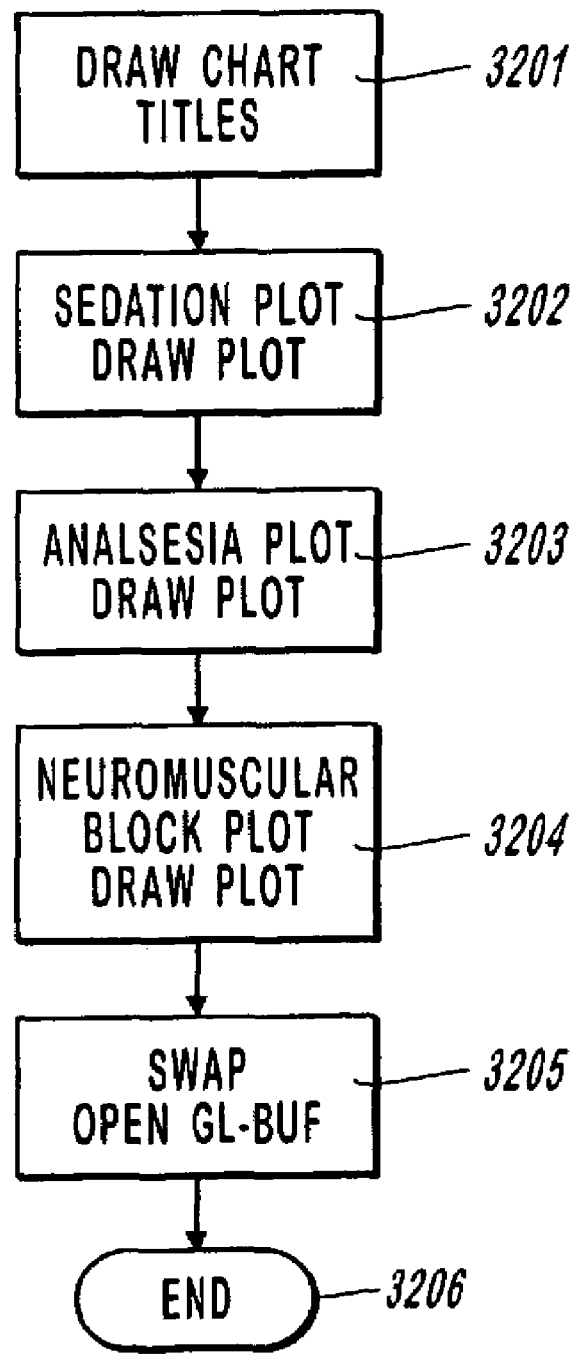
FIG. 32 is a detailed flow chart of the render the scene section of the preferred drug monitoring process of this invention.

FIG. 32 is a detailed flow chart of the render the scene section 3104 of the preferred drug monitoring process of this invention. First, chart titles are drawn 3201. Next, the sedation plot is drawn 3202. The analgesia plot is then drawn 3203. After which the neuro muscular block plot is drawn 3204. Additional detail on the plotting 32012, 3203, 3204 is discussed below with respect to FIG. 36. The OpenGL buffers are finally swapped 3206, after which this section of the process ends 3206.

Figure 33:
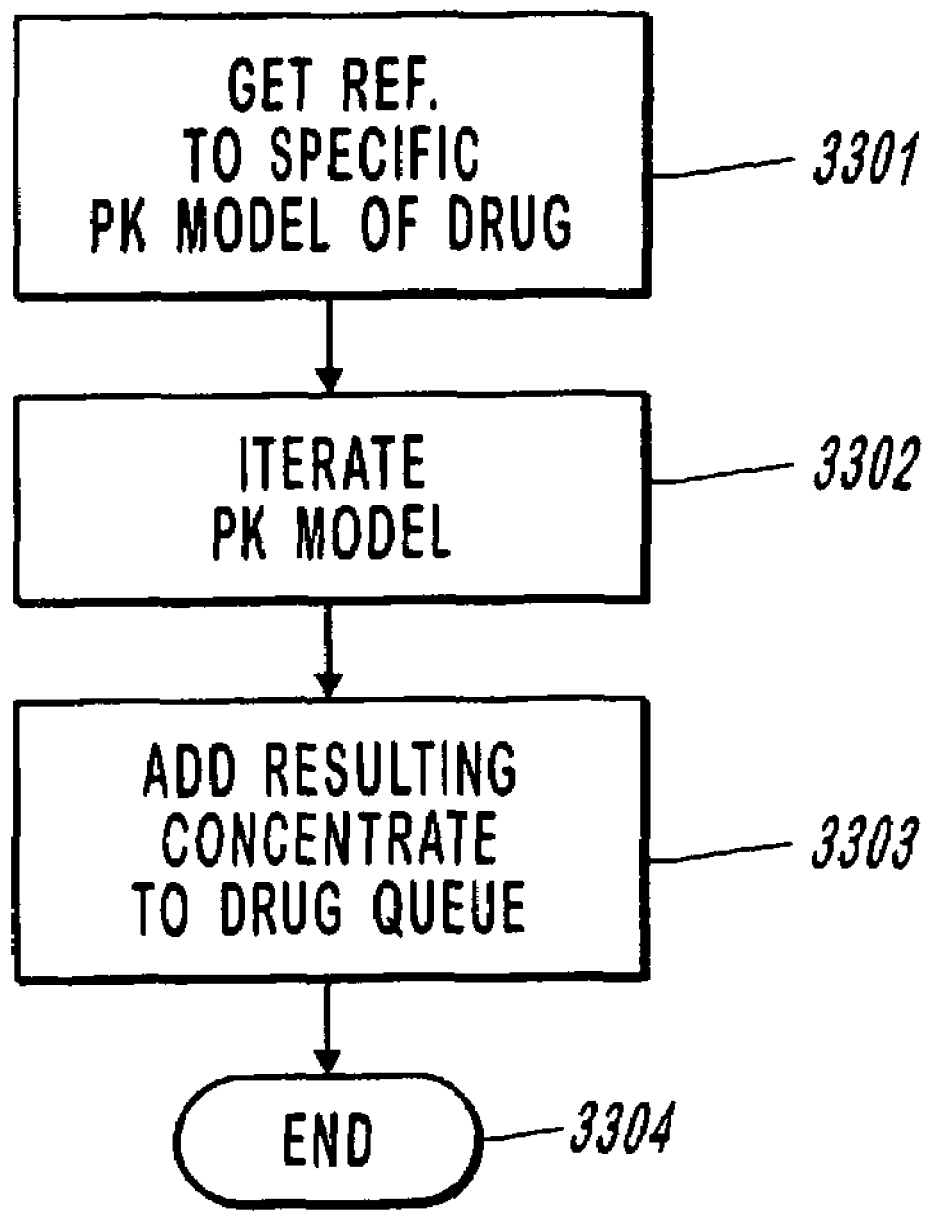
FIG. 33 is a detailed flow chart of the iterate drug model section of the preferred drug monitoring process of this invention.

FIG. 33 is a detailed flow chart of the iterate drug model section 3106 of the preferred drug monitoring process of this invention. First the reference to the specific PKModel of the drug is captured 3301. Next, the PkModel is iterated 3302. The preferred PkModel interaction uses an algorithm described in Shafer and Greg, Algorithms to Rapidly Achieve and Maintain Stable Drug Concentrations at the Site of Drug Effect with a Computer Controlled Infusion Pump, Journal of Pharmokenetics and Biopharmaceutics, vol. 20, #2, 1992. After iteration of the PkModel, the resulting concentration is added 3303 to the drug's circular queue of data, thereby including either past, present or predicted circular queues. Then this section of process ends 3304.

Figure 34:
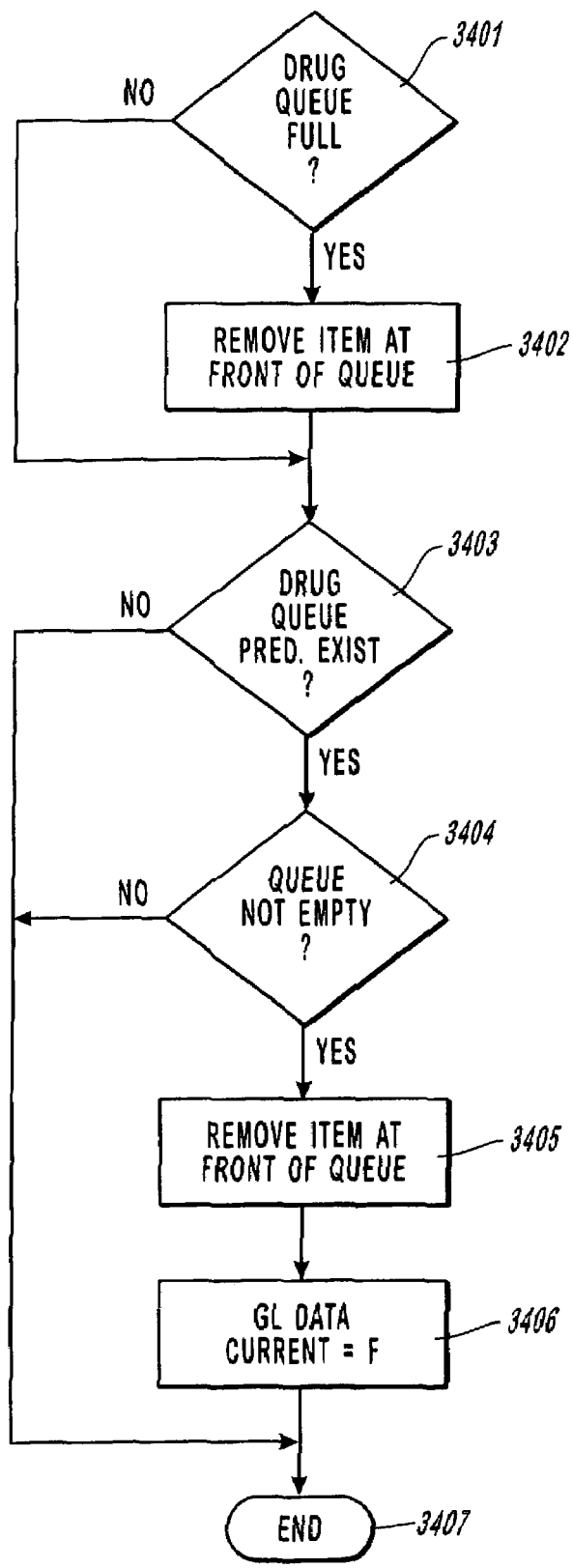
FIG. 34 is a detailed flow chart of the shift data left section of the preferred drug monitoring process of this invention.

FIG. 34 is a detailed flow chart of shift data left section of the preferred drug monitoring process of this invention. Initially, a test 3401 is made to determine if the drug queue is full. If the drug queue is full, then an item is removed 3402 from the front of the queue. Then a test 3403 is made to determine if the drug queue of predicted concentrations exists. If the predicted queue doesn't exist, then this section of the process ends 3407. If the predicted queue exists, then a test 3404 is made to determine if the queue is not empty. If the queue is empty, then this section of the process ends 3407. If the queue is not empty, then an item is removed 3405 from the front of the queue. The GL data current is set 3406 to false and this section of the process ends 3407.

Figure 35:
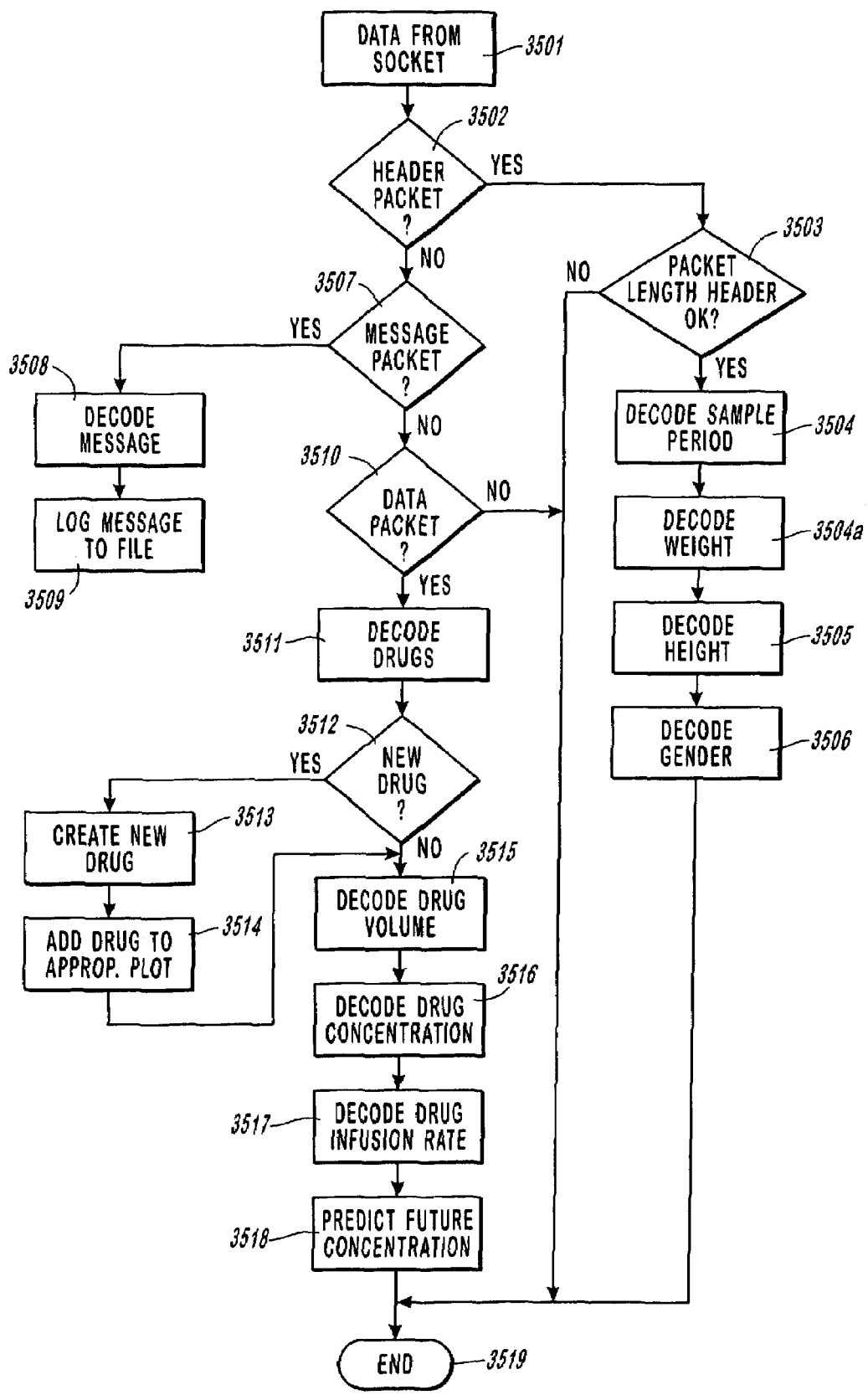
FIG. 35 is a detailed flow chart of the decode data packet section of the preferred drug monitoring process of this invention.

FIG. 35 is a detailed flow chart of the decode data packet section 2904 of the preferred drug monitoring process of this invention. The data is received 3501 from a socket. A test 3502 is made to determine if it is a header packet. If it is a header packet, then a test 3503 is made to determine if the packet length header is okay. If the packet length header is not okay, then the process of this section ends 3519. If the packet length header is okay, then the sample period is decoded 3504, the weight is decoded 3504, the height is decoded, and the gender is decoded 3506, after which this section of the process ends 3519. If it is not a header packet, then a test 3507 is made to determine if it is a message packet. If it is a message packet, then the message is decoded 3508 and the message is logged 3509 to a file. If it is not a message packet, then a test 3510 is made to determine if it is a data packet. If it is not a data packet, then this section of the process ends 3519. If it is a data packet, then drug data is decoded 3511. A test 3512 is made to determine if this is a new drug. If it is a new drug, a new drug record is created 3513, and the drug is added 3514 to the appropriate plot and the process continues to the decoding 3515 of the drug volume. If it is not a new drug, the drug volume is decoded 3515. Next, the drug concentration is decoded 3516, the infusion rate is decoded 3517 and the future concentration is predicted 3518, after which this section of the process ends 3519.

Figure 36:
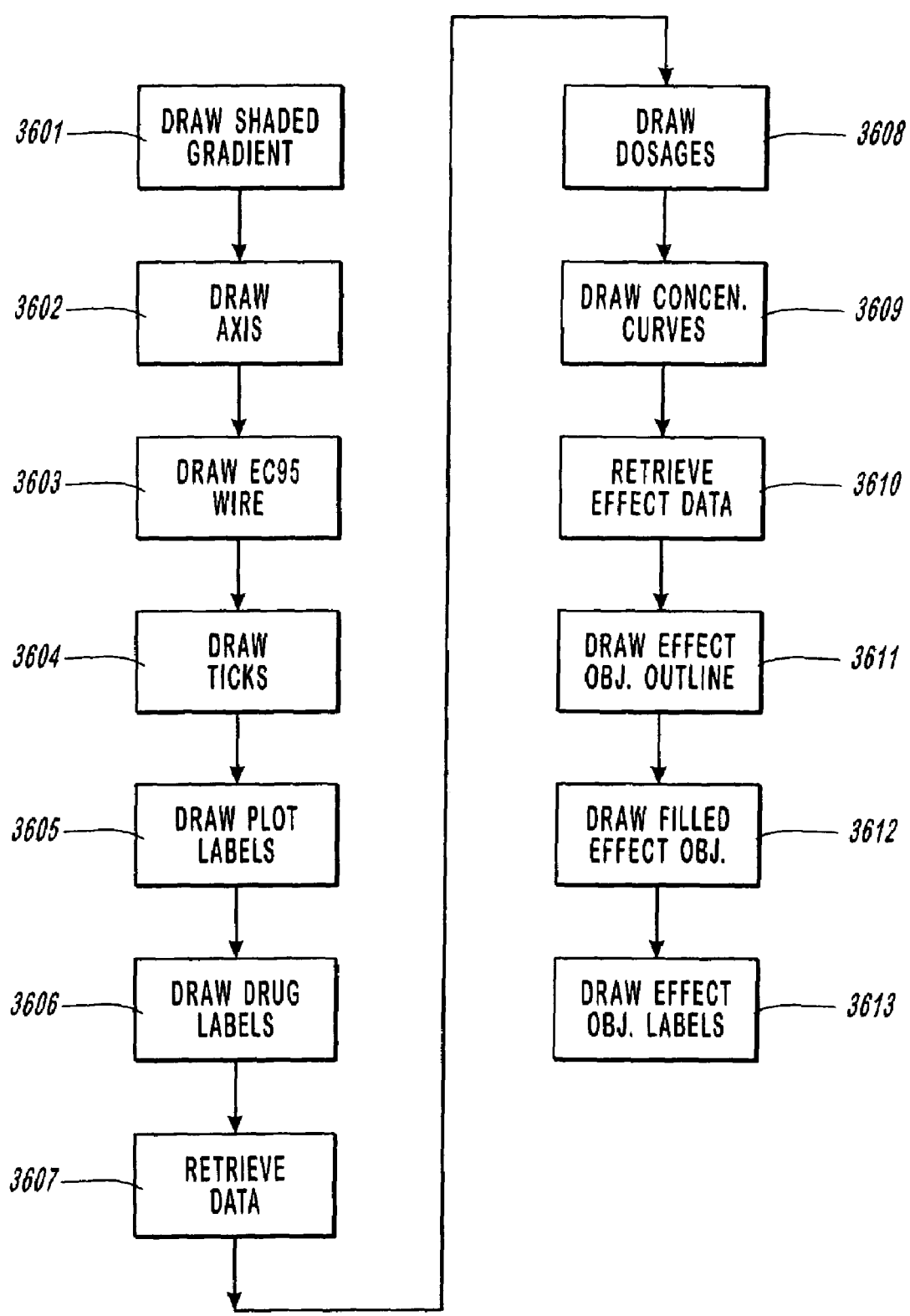
FIG. 36 is a detailed flow chart of the draw plot section of the preferred drug monitoring process of this invention.

FIG. 36 is a detailed flow chart of the draw plot sections 3202, 3203, 3204 of the preferred drug monitoring process of this invention. Initially, a shaded gradient is drawn 3601. The axes are drawn 3602. The EC95 wire is drawn 3603. Ticks are drawn 3604. Plot labels are drawn 3605. Drug labels are drawn 3606. Effect data is retrieved 3607, including concentration and dosage data for each drug in the plot. Dosages are drawn 3608. Concentric curves are drawn 3609. Effect data is retrieved 3610, as a percentage of effect. Effect object outlines are drawn 3611. Filled effect objects are drawn 3612, proportionally to the drug effect. The Object label effects are drawn 3613.

Figure 37:
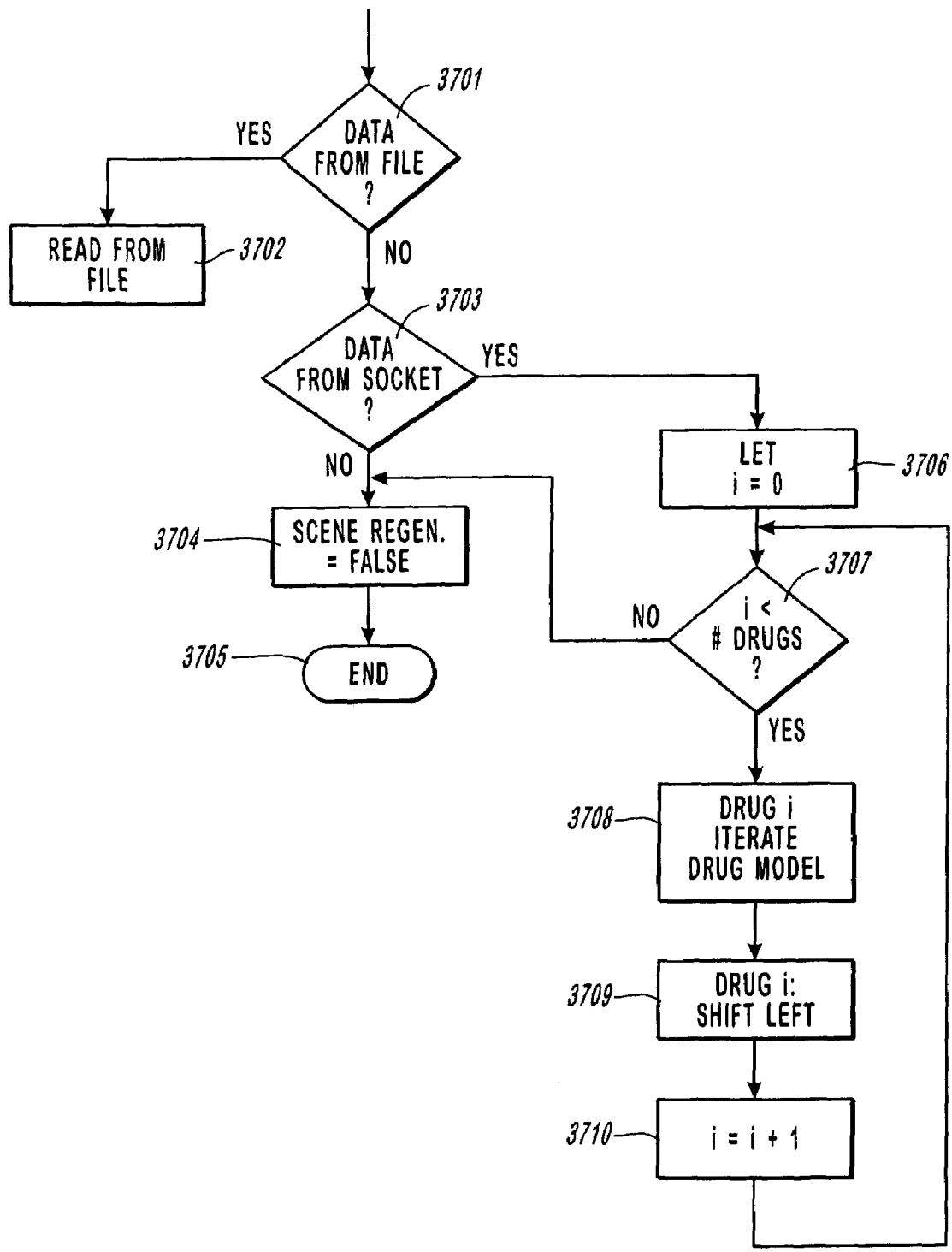
FIG. 37 is a detailed flow chart of the timer interrupt routine section of the preferred drug monitoring process of this invention.

FIG. 37 is a detailed flow chart of the timer interrupt routine section, see FIG. 29 step 2901, of the preferred drug monitoring process of this invention. A test 3701 is made to determine if the data is from a file. If it is from a file, the data is read from the file, as shown in FIG. 30 from step 3002 on. If the data is not from a file, a test 3703 is made to determine if the data is from a socket. If the data is not from a socket, then the scene rendered flag is set 3704 to false, and this section of the process ends 3705. If the data is from a socket, then I is set to zero. Next, a test 3707 is made to determine if I is less than the number of drugs. If I is not less than the number of drugs, then the process goes to step 3704. If I is less than the number of drugs, then the drug I is iterated 3708, as shown in FIG. 33, to generate the past and present concentrations. Next, the drug I is shifted left 3709, as shown in FIG. 34. I is incremented 3710 by one and the iteration process continues with test 3707.

Figure 38:
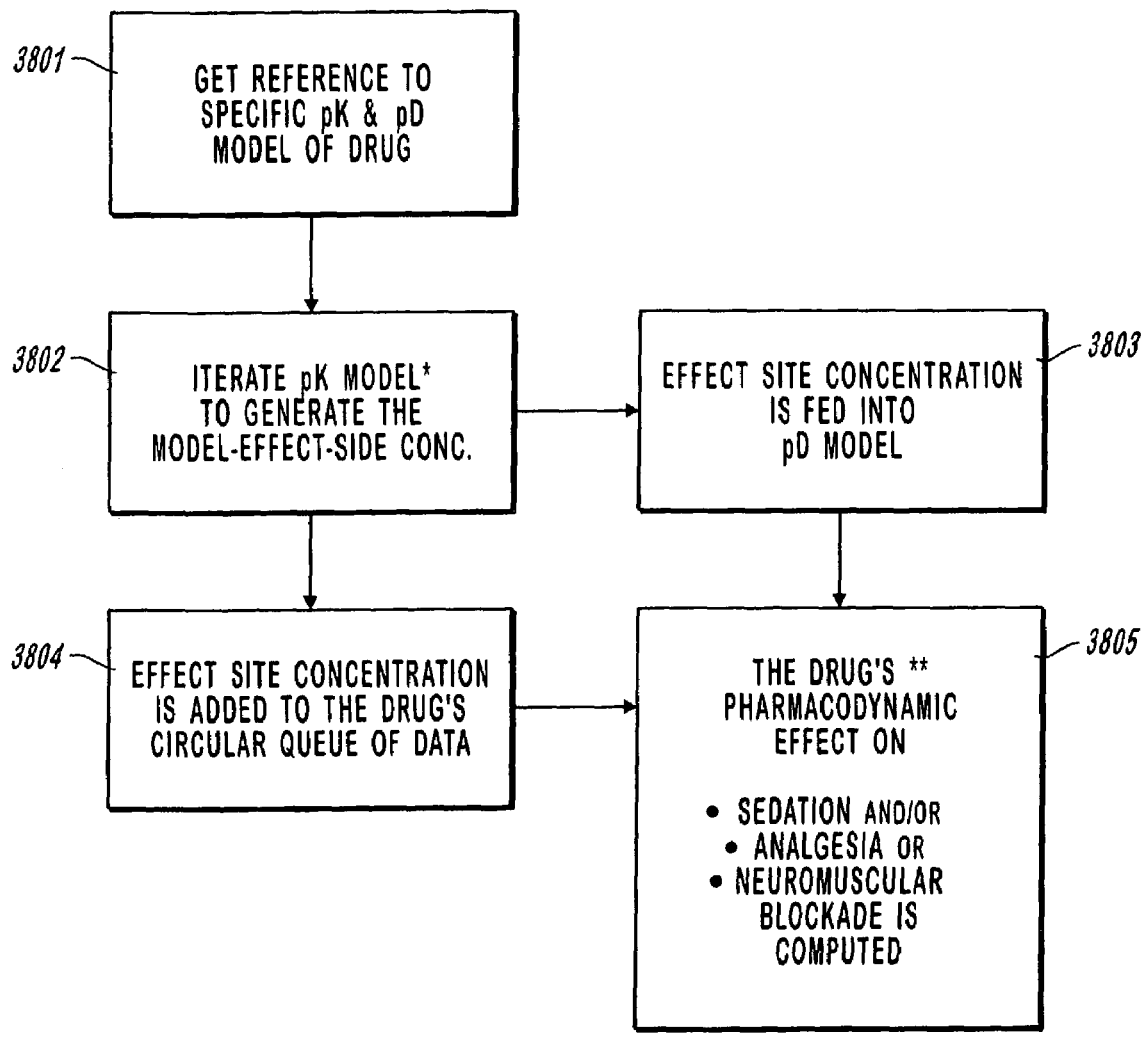
FIG. 38 is a detailed flow chart of the drug model.

FIG. 38 is a detailed flow chart of the drug model. Specific reference to the pharmacokinetic (pK) and pharmacodynamic (pD) models of a drug or drugs is obtained 3801. Wherein pK is a model algorithm used to rapidly achieve and maintain stable drug concentrations at the effect site with a computer controlled infusion pump. Shafer, S. L. and Greg, K. M., Journal of Pharmacokinetics & Bio Parmaceutics. Vol. 20(2), 1992, herein incorporated by reference in its entirety. The pD model of drugs represents drug-drug synergism. Guoming Xie's master thesis, Bioengineering, University of Utah 2000, herein incorporated by reference in its entirety. The pK model is iterated 3802 to generate the modeled effect site concentration. The process then goes to step 3803 where the effect site concentration is fed 3803 into the pD model, and/or 3804 where the effect site concentration is added 3804 the drug's circular queue of data. The drug's pD effect on sedation, analgesia and/or neuromuscular blockade is computed 3805.

Figure 39:
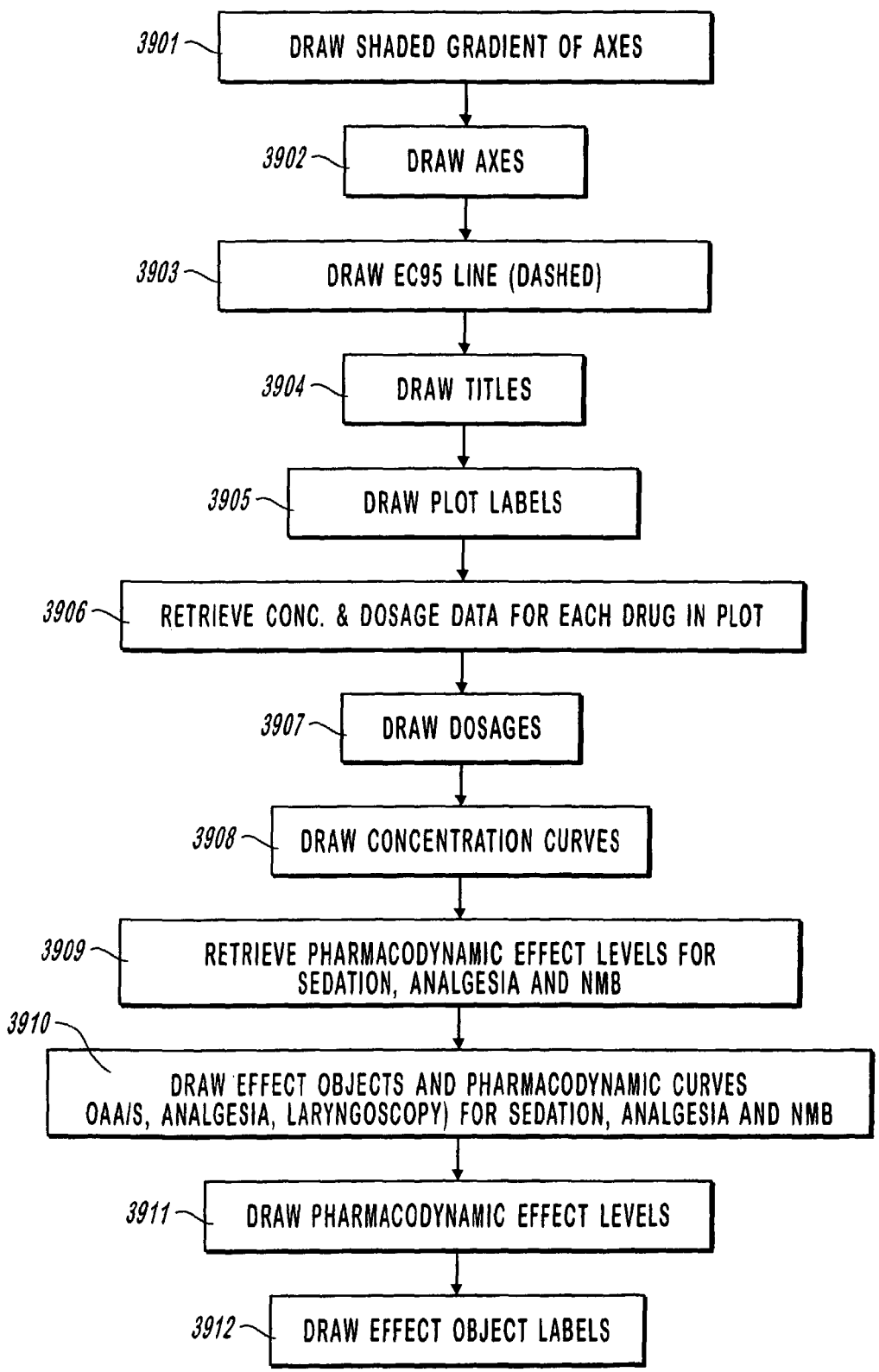
FIG. 39 is a detailed flow chart of the graphical display of infusions, effect site concentrations, and drug effects of intravenous drugs during anesthesia.

FIG. 39 is a detailed flow chart of the graphical display of infusions, effect site concentrations, and drug effects of intravenous drugs during anesthesia. The shaded gradient of axes is drawn 3901, from here the axes are drawn 3902. The EC95 wire is drawn 3903 as a dash. Titles are drawn 3904 and plot labels are drawn 3905. Concentration and dosage data for each drug in the plot is retrieved 3906 so that drug dosages can be drawn 3907. Concentration curves are drawn 3908. The pharmacodynamic effect levels for sedation, analgesia and neuromuscular blockade is retrieved 3909. The effect objects and pharmacodynamic curves (OAA/S, analgesia, laryngoscopy) for sedation, analgesia, and neuromuscular blockade are drawn 3910. The pharmacodynamic effect levels are then drawn 3911. Finally, the effect object labels are drawn 3912.

Figure 40:
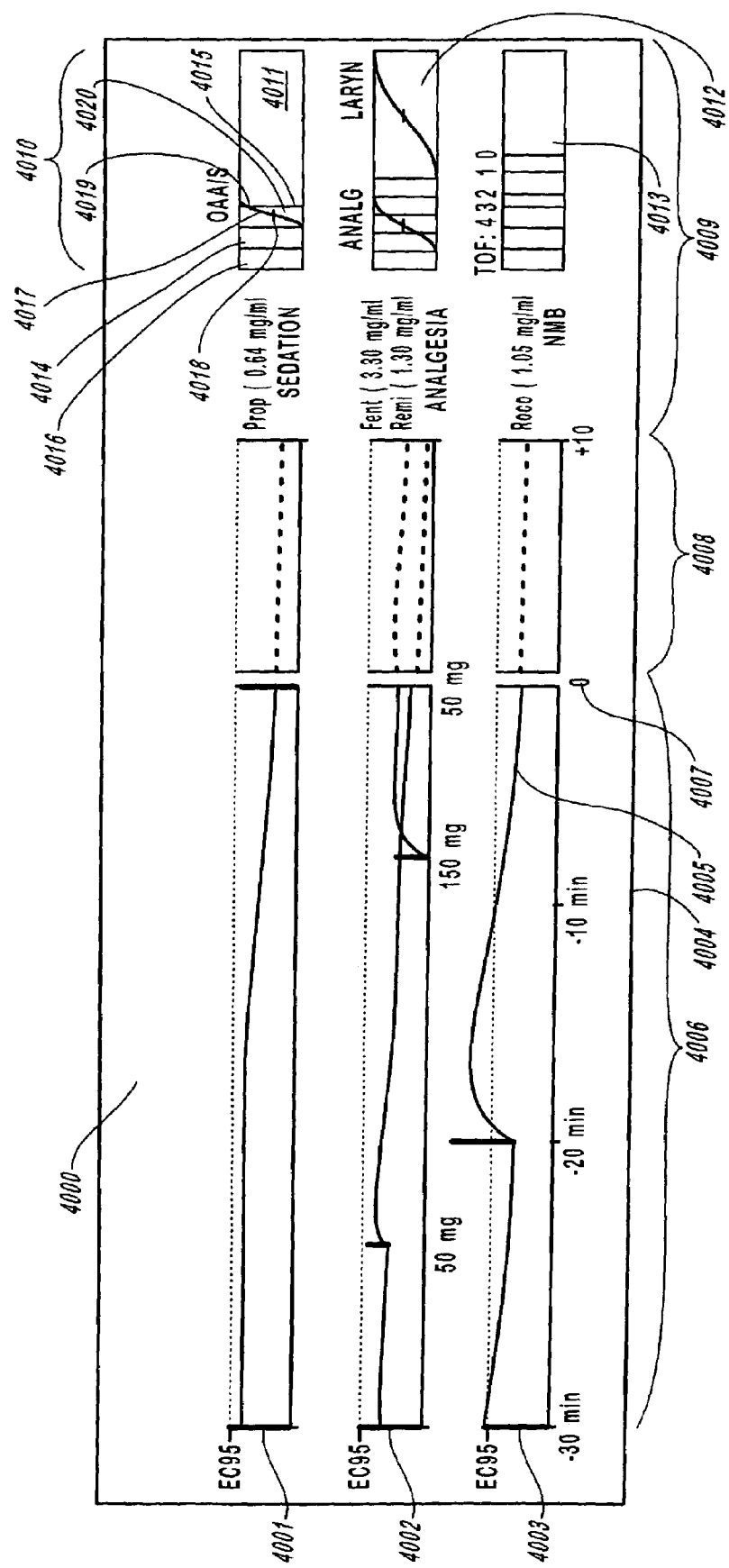
FIG. 40 is a view of a third example of the present display of the drug effects shown in this invention using a real-time graphical presentation of drug kinetics and dynamics.

FIG. 40 is a view of a third example of the preferred display 4000 of the drug effects shown in this invention using a real-time graphical presentation of drug kinetics and dynamics. There are three bar graphs indicating sedation 4001, analgesia 4002, and neuromuscular blockade 4003, wherein the x-axis 4004 provides past, present and future viewpoints measured by minute increments from the range of 30 minutes in the past to 10 minutes in the future. Effect site concentrations 4005 are indicated to show dosing history and the pharmacokinetic predictions of past 4006, current 4007 and future 4008 effect site concentrations via the time noted on the x-axis 4004. Predicted effect site concentrations 4008 are shown up to 10 minutes in the future. Infusion rates are displayed as horizontal bars and text 4009. Three concentration-effect graphs 4010 show the current pharmacodynamic model predictions of sedation 4011, analgesia 4012 and neuromuscular blockade 4013. Colored bands 4014 indicate the effects of individual drugs. The gray bars 4015 indicate the synergism of the drugs in combination. The pharmacodynamic effect scales 4016 are calibrated to clinical benchmarks such as the OAA/S scale and response to laryngoscopy. A reference frame 4017 demonstrates the predicted effect of the drugs in combination on the patient wherein the hatchmark 4018 indicates the EC50 for sedation or analgesia. The EC95 is at the top of the reference frame 4019 and the EC5 is at the bottom of the reference frame 4020.

Figure 41:
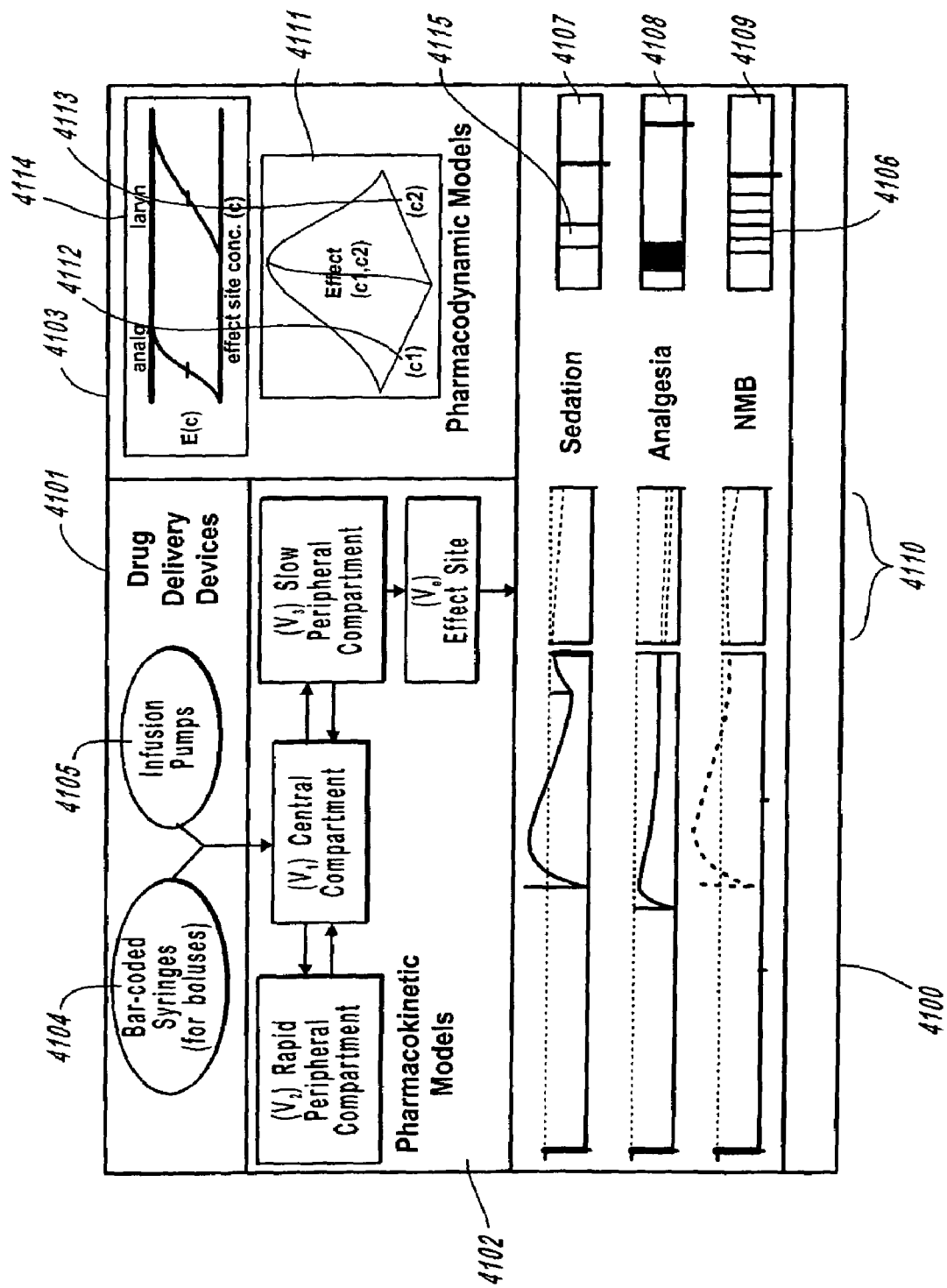
FIG. 41 is an expanded view of a third example of the preferred display of the drug effect shown in this invention, depicting the drug delivery devices, pharmocokinetic and pharmacodynamic models.

FIG. 41 is an expanded view of a third example of the preferred display of the drug effect shown in this invention, depicting the drug delivery devices 4101, pharmocokinetic 4102 and pharmacodynamic models 4103. Bar coded syringes 4104 and monitored infusion pumps 4105 constitute the hardware the tracks the drugs administered by the physician. Based on the drug input, the software programmed pharmacokinetic 4102 and pharmacodynamic models 4103 for remifentanil, propofol and rocuronium, for example, predict the effect site concentrations and the drug effects in real time. This information is then fed into the display 4000.

The drug display monitor 4100 is able to estimate, predict, and display drug dosages, infusions, effect site concentrations, and drug effects of intravenous drugs during anesthesia. The concentration and effect of drug 4106 are presented with respect to the classification of the anesthetic: sedatives (unconsciousness) 4107, analgesics (pain inhibitors) 4108, and neuromuscular blockades (muscle relaxants) 4109. Pharmacokinetic models 4102 of the anesthetic drugs, derived from the results of clinical studies, have been implemented and are used to estimate the drug concentrations at the effect site with respect to the general population of a given height, weight, gender and age. The models are typically run in real time, but in alternative embodiments or uses may be run faster or slower than real time and a prediction of the effect site concentrations 4110 shows up to 10 minutes into the future, although alternative future periods may be substituted without departing from the concept of this invention. A three-dimensional plot 4111 provides a three-dimensional view of the effect interactions of two medications 4112, 4113. A trend of the predicted effect site concentrations is shown to 30 minutes in the past, although alternative trend periods may be substituted without departing from the concept of this invention. Each drug may be color coded. Past, current, and predicted concentrations are normalized with respect to the drug's EC50 for sedation or analgesia and plotted relative to the time that it was administered. Drug administrations are shown as boluses or infusions.

The current drug effects are represented as bar graphs 4107, 4108, 4109. For sedation 4107, the effect-site concentrations drive pharmacodynamic models 4103, derived from the results of clinical studies, and present the drug effect of the "population normal" patient (normalized to height, weight, and/or gender). In the first graph 4107, as the level of sedation surpasses the OAA/S pharmacodynamic curve, the "population normal" patient is expected to become unconscious. In the analgesia bar graph 4108, the upper and lower bounds are given for the drug level required to prevent a somatic response. If the analgesia has surpassed the first pharmacodynamic curve (analgesia), then there will likely be no response to post-operative pain or surgical skin closure for the "population normal" patient. Likewise, if the analgesia level has surpassed the somatic response to a laryngoscopy (placement of an endotracial tube) 4114. In addition, mathematical models have been implemented to incorporate drug-drug synergism 4115 between propofol (sedative-hypnotic) and opiods (analgesics). The drug synergism is shown as a gray bar 4115 representing the additional effect due to the drug interactions. Finally, the neuromuscular blockade effect 4109 is shown in relation to the train-of-four twitch monitor. The bar graph 4109 relates the predicted number of twitches that would occur with a train-of-four monitor. As the drug level surpasses three twitches, then one would expect three twitches for the "population normal" patient, and as it passes zero, then no train-of-four response would be expected.

EXAMPLE 1

One embodiment of the invention includes a graphical drug display, shown as FIG. 40 used to determine the effect of such a display on the performance of anesthesiologists and nurse anesthetists (CRNAs) in the delivery of intravenous (IV) anesthetic drugs using in a full-scale patient simulation environment.

Figure 42:
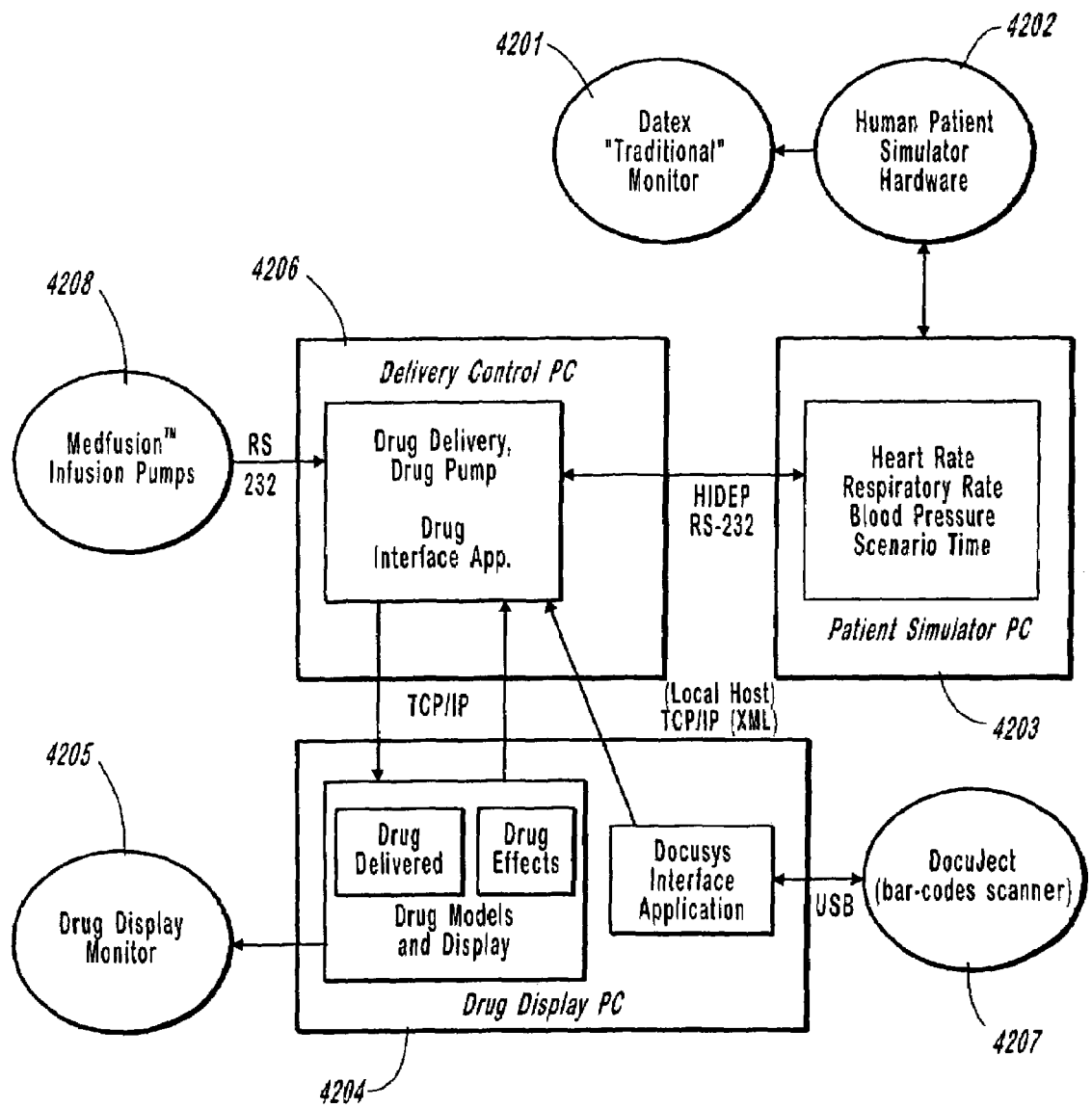
FIG. 42 is a detailed flow chart of an embodiment of the system setup.

FIG. 42 is a detailed flow chart of an embodiment of the system setup as conducted in a study. The drug display provides information about the drug doses administered, predicted effect site concentrations, predicted concentrations 10 minutes in the future, as well as model-based predictions of the synergistic effects of combined medications.

An evaluation of a beta version of this display using a computer based simulation (Anesoft Inc. Issaquah, Wash.) found an enhancement of the anesthesiologist's performance in administering drug boluses for analgesia, anesthesia, and neuromuscular blockade with use of the display. The results showed an improvement in the accuracy of drug delivery with the drug display present.

A more advanced version of the drug display has been developed, capable of presenting multiple drugs per class, model predicted interactions between different drugs, and drug administration via infusion pumps in a graphical display as shown in FIG. 40.

A study using such a graphical displayed measured drug delivery performance in a simulated high fidelity test scenario. The drug display is designed to support anesthesiologists and CRNAs delivery of drugs by providing information about drug concentrations in the past, the present, and the future. Its use is expected to result in: (1) more judicious administration of drugs, (2) better intraoperative control of sedation, analgesia, and neuromuscular blockade, (3) more rapid emergence for the simulated patient after the surgery. (4) and better postoperative pain management.

Design: In the study, a between subjects design with display conditions (traditional display only, traditional display and drug display) will be used. Analyses of all dependent variables will be based on this design.

Methods Subjects: 24 anesthesiologists and anesthetists with a range of clinical experience (CRNA, CA-2 and CA-3, and faculty) participated in the study evaluating this invention.

Materials: The METI anesthesia simulator [MET], Sarasota, Fla.) at the University of Utah Center for Patient Simulation was used to conduct the display evaluation. To evaluate the traditional display, the display is connected to an AS/3 anesthesia monitor 4201 (Datex, Helsinki, Finland) that displays the traditional electrocardiogram (ECG), arterial blood pressure (BP), pulse oximeter (SpO2), and capnogram (CO2) waveforms. Digital values for heart rate (HR), blood pressure (BP), oxygen saturation (SpO2) end-tidal carbon dioxide (FetCO2), and fraction of inspired oxygen (FiO2) is displayed via a patient simulator 4203 that is supported by patient simulator hardware 4202. The pulse oximeter tone will also be provided. All alarms will be in default mode and may be modified by the subjects according to their preferences.

The drug display of FIG. 40 provides information about drugs according to their classification, including intravenous sedatives 4001, analgesics 4002, and neuromuscular blocking agents 4003. Color-coded histogram bars show the drug boluses delivered to the patient 4010. Model predicted effect site concentrations are shown from thirty minutes in the past 4006 and ten minutes in the future 4008. The display 4000 is animated with the concentrations and dosages 4005 moving from right to left over time. Three concentration-effect graphs 4010 show the current pharmacodynamic predicted levels of sedation 4011, analgesia 4012, and neuromuscular blockade 4013 with respect to effect site concentration.

As IV drugs are administered, multi-compartment pharmacokinetic (PK) drug models 4102 predict effect site concentrations, and pharmacodynamic (PD) models 4103 use these predicted effect site concentration to predict the drug effects on the patient's levels of sedation 4011, analgesia 4012, and NMB 4013. The PK models 4103 of the drug display and the METI simulator are calibrated so that the simulated patient 4203 responds as the PD models predict it should. In instances of synergistic drug interactions (e.g. propofol-opioid), the drug display uses a PD drug interaction model to predict the combined drug effects on sedation, analgesia, and NMB (Guoming, PhD Dissertation). The default physiologic responses of the METI simulator are overridden by physiologic responses appropriate to the drug levels as predicted by the drug interaction models shown in Tables 1 and 2, below. Table 1 shows a pain scale and Table 2 shows the sedative and opioid effects on the cardiovascular system. The scenario will be constructed so elements of the patient's history make the use of cardiovascular drugs undesirable.

TABLE I

| Pain Scale | BP Max | BP Min | (P)SVR | HR Factor | HR | Stimulus |
|---|---|---|---|---|---|---|
| 1 | 110 | 80 | 1.0 | 1.00 | 78 | pre-surgery |
| 2 | 117 | 84 | 1.1 | 1.08 | 85 | |
| 3 | 123 | 89 | 1.3 | 1.17 | 91 | maintenance |
| 4 | 130 | 98 | 1.5 | 1.25 | 98 | closure |
| 5 | 137 | 98 | 1.7 | 1.33 | 104 | |
| 6 | 143 | 102 | 2.0 | 1.42 | 111 | Bankhart |
| 7 | 150 | 107 | 2.3 | 1.50 | 117 | Scope |
| 8 | 157 | 111 | 2.7 | 1.58 | 124 | |

Table 1 specifically shows the mapping of the pain scale to the METI Simulator's parameters. As the pain scale increases, a somatic response results in the increase of: blood pressure, pulmonary vascular resistance systemic vascular resistance, and heart rate. However, the analgesia drug levels may prevent these responses.

TABLE II

| Venous Capacity Factor | Blood Pressure Systolic | Blood Pressure Diastolic | V Mean Blood Pressure | Heart Rate (beats/min) | HR Factor |
|---|---|---|---|---|---|
| 1.00 | 131 | 66 | 88 | 79 | 1.00 |
| 1.20 | 130 | 65 | 87 | 75 | 0.95 |
| 1.40 | 126 | 61 | 83 | 72 | 0.91 |
| 1.60 | 125 | 60 | 82 | 69 | 0.87 |
| 1.80 | 119 | 55 | 76 | 66 | 0.84 |
| 1.90 | 114 | 52 | 73 | 64 | 0.81 |
| 2.00 | 101 | 44 | 63 | 62 | 0.78 |
| 2.05 | 95 | 40 | 58 | 60 | 0.76 |
| 2.10 | 83 | 34 | 50 | 58 | 0.73 |
| 2.15 | 77 | 30 | 46 | 55 | 0.70 |
| 2.20 | 64 | 25 | 38 | 52 | 0.66 |
| 2.25 | 58 | 22 | 34 | 49 | 0.62 |

Table 2 shows the drug levels (synergistic effects of analgesia and anesthesia) directly modulate the METI Simulator's venous capacity and heart rate factor. An increase in drug levels increases the venous capacity factor (which lowers the arterial blood pressure). The heart rate factor is decreased. An adequate level of anesthesia and analgesia can prevent or lessen the intensity of a somatic response to laryngoscopy and surgical stimuli. An "overdose" of propofol and/or opioids will result in hypotension and bradycardia. The drug display 4204 receives data from computerized IV drug delivery systems 4206. The Docuject© 4207 [DocuSys Inc. Mobile, Ala.] drug delivery system reads and records bolus doses of drugs administered via bar-coded syringes. The Medfusion™ 3010a (Medex Inc. Duluth, Ga.) infusion pumps 4208 relay IV infusion rates (mg/hr) through a serial port. For both devices, the drug concentration and amount delivered per unit time are sent to the delivery control PC 4206 and the drug interface application relays the information to the drug display 4204 and the operator of the human patient simulator via the drug display monitor 4205.

Example Scenario

The surgery involves shoulder arthroscopy (Bankart procedure) on a 62 y/o, 80 kg male. The patients past medical history is significant for coronary artery disease which has been stable since stent placement one year ago, controlled hypertension, and a family history of malignant hyperthermia (MH). The patient is known to be MH susceptible by muscle biopsy.

The patient has had total intravenous anesthesia (TIVA) for 2 prior surgical procedures and there were no anesthetic complications. The patient does mention that he had considerable postoperative pain after a previous shoulder procedure.

The surgeon has requested muscle relaxation for the procedure. The procedure will either be 20 minutes long if it only requires arthroscopy or 45 minutes if an open repair is needed.

For the scenario, TIVA will be required. To provide sedation, propofol will be available via bolus and continuous infusion. Remifentanyl (bolus and infusion) and fentanyl (bolus only) will be available for analgesia. Rocuronium (bolus only) is the available neuromuscular blocking agent.

Following intubation and transition of the patient to a semi-Fowler's position, the surgeon attempts to determine whether the Bankart procedure will be necessary via an exploratory evaluation. After 5 minutes, the surgeon announces that it will be necessary to convert to and open joint Bank art procedure. It is requested that the patient continues to have complete NMB for the duration of the surgery. Because the procedure is invasive and painful, the analgesic requirement increases (Table 2). Ten minutes into the surgery, the surgeon announces that the procedure is going very well and expects to close in approximately 10 minutes. Ideally, after skin closure, the patient should rapidly recover from the sedation and the NMB while having an appropriate amount of analgesia to relieve post-operative pain.

Measures. During the simulated surgery, predicted effect site concentrations of all administered drugs and model predicted levels of sedation, analgesia, and NMB will be recorded at two-second intervals. The values of the vital signs will be recorded at four-second intervals. Heart rate and blood pressure values will be extracted and sent to a spreadsheet.

Drug management performance will be calculated by comparing the predicted level of analgesia provided versus the simulated level of surgical stimulation. Because the simulator has been calibrated such that the physiologic responses match the pharmacodynamic predictions, a two-by-two repeated measurement analysis of variance (ANOVA) will be used to analyze tracking performance for the pharmacodynamic prediction of analgesia and the level of surgical stimulation (with or without the display). A criterion value of $p<0.05$ will be used for all analyses. Data will be presented as a mean standard deviation of the difference. The precision of drug administration will be measured as the standard deviation and the root-mean-square error (RMSE) between the predicted drug effect and the simulated level of surgical pain.

A train-of-four stimulus will be measured at 10-minute intervals and prior to removal of the endotracheal tube to assess the level of neuromuscular blockade. A t-test will be used to examine differences in the number of adjustments in propofol and remifentanil drug administration during maintenance.

Deviations from the preinduction heart rate (HR) and systolic blood pressure (SYS) will be used to determine the patient's responses to pain. The criteria for inadequate anesthesia will be a SYS more than 15 mmHg above the baseline and tachycardia higher than 90 beats/min, in the absence of hypovolemia (Ausems, Anesth 68:851-61, 1988). Excessive level of anesthesia will be SYS more than 15 mmHG below the baseline and bradycardia lower than 40 beats/min. For this analysis, the time interval during which heart rate or systolic blood pressure deviates from these thresholds will be computed. The baseline values for the vital signs will be determined by averaging vital sign data of the first 36 seconds of simulation, prior to intubation and drug administration. Vital sign differences between the two display conditions will be analyzed using an ANOVA test. Differences at the end of maintenance will be analyzed using a Fisher's exact test.

Patient vital signs will be recorded for 15 minutes following extubation. Minimum, maximum, mean, and percent deviations from baseline will be calculated. The time duration from completion of skin closure to awakening (spontaneous respiration and eye opening) and extubation will be recorded. Anesthetic records, vital sign measurements, and drug delivery information will be reviewed by three experienced anesthesiologists and scored on a scale of 0-100 according to their expert ratings of the quality of anesthesia provided by each subject.

Upon completion of the scenario, subjects will complete questionnaires related to measures of cognitive workload (NASA-TLX) satisfaction", and subjective utility of the drug display. A t-test <<-ill be used to determine differences between the experimental conditions.

Evaluation Procedure. When each subject arrives for the experiment, they will complete a questionnaire describing experience level, length of time working prior to the study. caffeine consumption, sleep history, and whether or not they require vision correction. Subjects will then be instructed about the general task in the experiment, i.e. that they have to administer anesthesia during a standard surgery. All participants will be instructed in the use of the METI simulator, interpretation of the drug display, Docuject, and the Medfusion 3010a pumps. Subjects will then induce anesthesia, intubate the trachea, care for the simulated patient throughout the procedure, and extubate the patient following skin closure and awakening.

Evaluation Training. A minimum amount of training is required with the high fidelity simulator because most subjects are familiar with the simulator as part of their training. Subjects will receive information about the simulator and be encouraged to ask questions about the simulator and its function. In both conditions, subjects will be asked if they are familiar with the set up of the standard monitoring equipment. All subjects will be instructed in the use of the Docuject and Medfusion 3010a drug delivery systems. Each subject will then use these devices to demonstrate the administration of a fixed infusion and three specified bolus doses of sterile eater representing the medications to be depicted in the simulation. Training for the simulator is completed when the subject reports feeling comfortable with administration of the anesthesic agents in the simulated patient.

A computerized tutorial will be presented in order to provide standardized training in use of the drug display for all subjects. Subjects will be shown static screen shots of the drug display monitor depicting the effect site concentrations and current effects of propofol, remifentanil, and rocuronium on sedation, analgesia and NMB. The display will be explained in detail including: axes, labels, drug classifications, effect site concentrations according to EC95. the effect bars. effect site concentration and its relation to drug effect, predicted, past, and present concentrations. The participants will be told that the display shows estimated effect site concentrations and drug effects generated from pharmacodynamic models.

In both conditions, after explaining the simulator, the subjects will be reminded that they have to administer anesthesia and provide care for the simulator patient. All questions concerning the use of the monitors, the procedure, etc will be answered immediately by the experimenter. On average, the training is expected to take 10 minutes. One-half of the subjects will be assigned randomly to the drug display condition and the remaining one-half will be assigned to the control condition, with equal numbers of attending anesthesiologists assigned to each group.

Evaluation Testing. The subject will be given a new anesthetic record and will be asked to fill it out during the course of the test scenario. Prior to starting the simulation, the subjects will be given the patient's preanesthetic evaluation form which includes: the patient's medical and surgical history, labs, baseline vital signs, planed surgical procedure, and the expected duration of the surgery. The patient will be presented as having arrived in the operating room without prior sedation or pre-oxygenation; however, ECG electrodes, an IV, an arterial line, and a non-invasive blood pressure cuff will already be in place. The subject will be reminded that they may administer boluses or continuous infusions of propofol and remifentanil, as well as bolus doses of fentanyl and rocuronium. Antagonist drugs will not be available for use. The subjects will be asked to administer anesthesia such that the patient is awake and spontaneously breathing as quickly as possible after the surgery with minimal post-operative pain. The simulation will end when the surgeon has finished closing and the patient is extubated. A video camera will record the training and the testing phases of the experiment.

After completing the experiment, the subjects will answer a NASA-TLX questionnaire and a short questionnaire about the drug display (see Appendix). Each study session is expected to last approximately one hour, and the subjects will be compensated $50 for their participation.

Procedure to compute the patient state: 1.Get the pain scale from the simulator scenario: painScale=computePainScale( ); 2.Get the analgesia drug scale from the models in the drug display: drugscale=getDrugScale( ); 3.Get the sedation drug level from the models in the drug display: sedationLevel=getSedationLevel( ); 4.Compute the resulting heart rate:hrPainFactor=getPainHRFactor(painScale) hrDrugFactor=getDrugHRFactor(drugScale) hr=80.0*hrPainFactor* hrDrug,Factor; 5.Compute the resulting SVR and PVR:svrPainFactor=getPainSVR(painScale):svrDrugFactor=getDrup-ISVR(drueScale); svrFactor=svrPainFactor*svrDrug-Factor;(same for PVR) 6Systolic and Diastolic BP due to pain is encoded within the scenario (derived from painScale) 7.Compute the resulting venous capacity factor (offsets the somatic responses due to the drug) VcFactor=getVcFactor(drugScale); 8.Compute the Respiratory rate RR=getRespRate(sedationLevel); 9.Compute the "Eyes Open or Closed" ResponseEyes=getEyes(sedationLevel); 10.Set using HiDEP. the following parameters for the simulator SvrFactor. pvrFactor, vcFactor, hr. eyes, and rr.

EXAMPLE 2

A study was performed to determine if in the presence of the drug display, the anesthesiologist's delivery of drugs will be more judicious and efficient, resulting in better control of the patient's vital signs and depth of anesthesia during the surgery.

Material and Methods. Subjects. After obtaining approval from the institutional review board at the University of Utah, we evaluated 14 resident/attending anesthesiologist "teams" as they performed 3 TIVAs (total intravenous anesthetics) in the operating room. Residents were CA-2, CA-3 or chief residents. Study Design: The teams were evaluated during 42 laparoscopic surgeries (cholecystectomy, hernirraphy, tubal ligation) for ASA Class I, II and III patients with informed consent. Teams were limited in their choice of intravenous anesthetic agents: propofol for sedation, remifentanil, fentanyl, and sufentanil for analgesia, and rocuronium as a muscle relaxant. However, the anesthesiologists administered intravenous reversal agents and cardiovascular drugs as necessary.

All participating anesthesiologists used the Docuject (DocuSys Inc, Theodore Ala.) intravenous drug delivery system 4207 for administering bolus doses of drugs. All bolus anesthetic and reversal agents as well as cardiovascular drugs were administered using the Docuject system 4207. In addition, the teams administered drug infusions with two Medfusion (Medex Inc, Duluth Ga.) 2010i infusion pumps. Half of the participating teams (7 teams, 21 surgeries) had the University of Utah drug display presented alongside the standard OR monitors to help guide them during the anesthetic. A between subject design was used. That is, the teams that had use of the drug display presented did not participate as subjects for the condition without the drug display. The "no drug display" condition was executed first, and the teams were allowed to us the display in the second condition.

Training. All teams were trained to use the Docuject drug delivery system. The Medfusion intravenous pumps 4208 are the standard pumps used in the operating room, and no training was necessary. In addition, the teams assigned to the drug display experimental condition were trained to use the drug display.

Because the Docuject drug delivery system is a new medical device, a brief training session on its use was necessary. Each team was trained to use the Docuject system in the operating room before their first case in the study. First, a short, scripted, demonstration was given by one of the experimenters. The experimenter explained the Docuject system: the syringe, the barcode, the technology to read the barcode and present the drug information, the technology to compute the amount of drug administered, and how to properly insert the syringe into the injection port of the IV-line. Teams learned to use the device with three sterilized mock syringes (propofol, fentanyl, rocuronium) that were affixed with barcodes representing the drugs used in the case. Anesthesiologists filled the syringes with sterile water and administered the drug to an IV port connected to an empty IV bag using the Docuject system. The experimenter answered all questions about the Docuject system. Both members of the team were tested to criterion by successfully administering specified amounts of the 3 mock drugs. On the day prior to using the drug display in the experimental condition, the team was trained to use the display. Each member of the team was trained separately. First, a digital video of the drug display was shown. The video described all of the graphical and numerical aspects of the display. In addition, the video displays an animation of a mock anesthetic was shown in accelerated time (20 times faster than real-time) with a numeric clearly showing the time. Finally the video described the limitations of the drug display: only modeled data for a population, does not incorporate reversal agents or cardiovascular drugs.

Next clinicians used a software program designed to simulate the bolus and infusion delivery of drugs (propofol, fentanyl, remifentanil, sufentanil, and rocuronium). Clinicians were asked to use the drug display in conjunction with the drug delivery simulator to titrate intravenous drugs for a young and healthy, 70-kg male undergoing an intra-abdominal surgery (with a large surgical incision). The anesthesiologist was asked to administer drugs to obtain adequate analgesia for the following stimuli: a laryngoscopy, surgical incision, surgical closure, patient wake-up, and post-operative analgesia. Questionnaires: After each case, the members of the team were required to use a NASA-TLX questionnaire to score their perceived physical, mental, and temporal demand for the surgery. After the team had fulfilled their quota of 3 TIVAs, they were given additional questionnaires on the utility and added value of the drug display and the Docuject systems.

Procedure Before starting surgery for the day, the Docuject and Drug Display system was set up in the designated operating room. The sterilized Docuject and the two Medfusion pumps attached to an IV pole. The infusion pumps could be moved according to the anesthesiologist's preference. A desktop PC on a cart ran software that coordinated the drug information with the drug delivery systems and the drug display, with digital output (Docuject—USB, Medfusion—RS-232) being sent to the PC. All intravenous drug delivery and predicted effect-site concentration data were saved to a file, with the time calibrated to the nearest minute of the time shown on the traditional monitors. When the drug display was shown, it was presented on a laptop PC next to the traditional monitors (or according to the anesthesiologist's preference). When the drug display was not shown, the pharmacokinetic and pharmacodynamic models used by the drug display were executed in order to predict and store the effect-site concentrations for later analysis. Before the first case, a standardized checklist of system tests was used to ensure all software and hardware was working properly.

After each case, a table of vital sign trends recorded at one minute intervals was acquired from the traditional monitor (Datex and Eagle) were collected. All digital data stored on the experimenter's desktop PC were saved to a file for subsequent analysis. In addition, NASA-TLX questionnaire was given to both the resident and the attending anesthesiologist to complete. After the team had completed three TIVAs in the study, they completed the questionnaires on the utility and value of the drug display and the Docuject system.

Data Recording and Analysis After completion of the 42 cases, the data were analyzed: 1.Record the total dose/kg and average dose/kg/unit time of all drugs administered. The costs of the drugs for the anesthetic were computed and differences in cost with regard to experimental condition were analyzed. 2. The variance in the following vital signs were analyzed during the case: •heart rate,•non-invasive BP (one to three minute intervals). 3.The differences between conditions were measured. Several variables were analyzed with respect to the patient's time to recovery. We measured the time from the point at which sutures were in place to the time of:•wake up,•spontaneous breathing, •removal of endotrachial tube, •ready for discharge in the PACU•Aldrete scores in the PACU (30 min and 2 hours post surgery). 4.Reversal agents used, time administered, and amount given.

5.Experts rated the performance of each anesthetic: The impact of the drug display on performance to deliver anesthesia was evaluated. Three experts judged the anesthesiologists" performance.

To evaluate the performance the experts used the anesthesia record, a record of monitored heart rate, blood pressure and SaO2, and the drugs administered. They judged whether anesthesiologists responded in a timely manner to changes in the vital signs, appropriate and efficient administration of drugs, and overall performance. The experts rated the performance with regard to these variables on a scale from 0-100, with 0 worst performance possible and 100 best performance possible. The ratings were used to assess performance independently from the measured variables (such as vital signs). It is to be understood that the above-described embodiments and examples are merely illustrative of numerous and varied other embodiments and applications which may constitute applications of the principles of the invention. These above-described embodiments are provided to teach the present best mode of the invention only, and should not be interpreted to limit the scope of the claims. Such other embodiments, may use somewhat different steps and routines which may be readily devised by those skilled in the art without departing from the spirit or scope of this invention and it is our intent that they are deemed to be within the scope of this invention.

The invention claimed is:

1. A system for modeling and predicting anesthesia drug effects on a patient, comprising:
   a drug delivery system configured to deliver anesthesia drugs into the patient;
   a data stream device, in communication with the drug delivery system
   a simulator in communication with the drug delivery system, the simulator being configured to simulate drug administration effects and simulate infusion drugs by representing drug effects over time as a multi-dimensional visualization;
   a drug display monitor in communication with the data stream device and including:
      a data decoder receiving data from the data stream device;
      a dosage calculator receiving decoded data from the data decoder;
      a drug modeler and normalizer receiving calculated data from the data decoder;
      the drug modeler configured to determine a present and future probability of effectiveness of at least one drug introduced into the subject by the drug delivery system, wherein the present and future probabilities of drug effectiveness include a correlation of modeled pharamacokinetic data and modeled pharmacodynamic data; and
   a display generator that produces a display of:
      the present and future probabilities of effectiveness including predicted pharamacokinetic effect side concentrations depicted as a percent of a concentration value corresponding to a known pharmacodynamic probability of causing a particular bodily effect;
      a three-dimensional plot configured to provide a three-dimensional view of the effect of interactions of at least two anesthesia medicines;
   a bar graph and drug synergism is shown as an additional bar on the bar graph representing the additional effect on the patient due to drug interactions as the simulator simulates anesthetic drugs from the multi-dimensional visualization
   a probability of effectiveness of at least one drug administered, including at least one of:
   a probability that a subject will be rendered unconscious by at least one drug having a sedative effect;
   a probability that a subject will not exhibit pain from laryngoscopy, incision, or post-operative recovery of surgery by at least one drug having and analgesic effect; and a probability that a subject will not exhibit a response to a train-of-four electrical muscle stimulation by at least one drug having a neuromuscular blocking effect, the probability of effectiveness determined based upon the model.

2. The system recited in claim 1, wherein the drug delivery system includes:
   an infusion pump;
   an anesthetic administration machine; and
   one or more bar coded syringes.

3. The system recited in claim 1,
wherein the drug delivery system includes a simulator, which simulates drug effects.

4. The system recited in claim 3,
wherein the simulator simulates bolus drugs, infusion drugs, anesthetic drugs, sedative drugs, analgesic drugs and neuromuscular blocking drugs.

5. A system for modeling and predicting anesthesia drug effects on a patient, comprising:
a processor, computing drug models, producing an internal representation of drug display data and decoding a data stream, wherein the processor is configured to determine a present and future probability effectiveness of at least one drug introduced into the subject by the drug delivery system, wherein the present and future probabilities of effectiveness include a correlation of a predicted drug effect site concentration based on modeled pharmacokinetic data and modeled pharmacodynamic data;
wherein the future probability of effectiveness of the at least one drug is represented in real time, comprising:
(A) a graph depicting a probability of effectiveness of at least one sedative, referenced according to a measure of consciousness;
(B) a graph depicting a probability of effectiveness of at least one analgesic, referenced according to a measure of surgical stimuli and according to a measure of laryngoscopy; and
(C) a graph depicting a probability of effectiveness of at least one neuromuscular blocking agent, referenced according to a measure of neuromuscular blocking,
a memory unit in communication with the processor;
a long term memory unit in communication with the processor;
a graphics adapter in communication with the processor; and
a display monitor, in communication with the graphics adapter, configured to graphically depict:
a mode of administration of at least one drug, with different modes of administration being readily identifiable and readily distinguishable from one another,
a three-dimensional plot configured to provide a three-dimensional view of the effect of interactions of at local two anesthesia medicine;
a bar graph wherein drug synergism is shown as an additional bar on the bar graph representing the additional effect on the patient due to drug interactions; and further configured to depict, in substantially real time, the present and future probabilities of effectiveness including predicted pharmacokinetic effect site concentrations depleted as a percent of a concentration value corresponding to a known pharmacodynamic probability of causing a particular bodily effect.

6. The system recited in claim 5,
wherein the display monitor is configured to depict a graph representing an additional effect,
wherein the additional effect results from drug interactions, comprising a system for executing a multi-dimensional pharmacodynamic mathematical model to simulate the interactive pharmacokinetic and pharmacodynamic effects between sedatives and analgesics.

7. The system recited in claim 6, wherein the processor processes:
information regarding receiving the potency of a drug;
a calculator calculating the relative potency of a drug in a class of drugs; and
a merge function combining the relative potencies of two or more drugs to calculate the total effect of the two or more drugs.

8. The system recited in claim 5,
wherein the display monitor is configured to depict a graph representing an additional effect,
wherein the additional effect results from drug interactions, comprising a system for data representation that maps multi-dimensional drug effect surfaces, generated by a pharmocodynamic model, to a respective graph of the drug class with sedative and analgesia drug effect site concentrations as input.

9. The system recited in claim 8, wherein the processor processes:
information relating the sedative and analgesic volumes of a drug;
a calculator for calculating a combination effect of the drug with other drugs; and
a correlator for mapping the combination effect to a two-dimensional graph.

10. The system recited in claim 5, wherein the display monitor is configured to depict a graph representing an additional effect, wherein the additional effect results from drug interactions, comprising a system for differentiating the individual and interactive components for estimated drug effects in the data representation.

11. The system recited in claim 10, further comprising: a calculator for calculating an effect of a first drug acting alone; a display for displaying a first drug effect; a calculator for calculating an effect of a second drug acting alone; a display for displaying the second drug effect; a calculator for calculating a combined effect of the first and the second drug effects; and a display for displaying the combined effect.

12. The system recited in claim 1, wherein the display generator produces a display of probabilities of effectiveness of at least two drug effects.

13. The system recited in claim 1, wherein the display generator produces a display of probabilities of effectiveness of at least two drugs.

14. The system recited in claim 13,
wherein the display generator produces a display of probabilities of effectiveness of at least one sedative, at least one analgesic, and at least one neuromuscular blocker.

15. A method for modeling and predicting drug anesthesia drug effects on a patient, comprising:
determining a present and future probability of effectiveness of at least one drug introduced into a subject by a drug delivery system, wherein the present and future probabilities of effectiveness include a correlation of a predicted drug effect site concentration based on modeled pharmacokinetic data and a probability of achieving a bodily effect on the patient based on modeled pharmacodynamic, pharmacokinetic and pharmacodynamic drug interactions, and a predictive pharmacodynamic model including a three-dimensional surface developed from data corresponding to pharmacodynamic effectiveness of the at least one drug on a plurality of individuals to whom the at least one drug was previously administered;
converting the three-dimensional surface to a simplified two-dimensional model;
displaying a bar graph and drug synergism is shown as an additional bar on the bar graph representing the additional effect on the patient due to drug interactions; and
displaying the two-dimensional model on a display; including at least one indicator of the probability of effectiveness of the at least one drug and including predicted pharamacokinetic effect site concentrations depicted as a percent of a concentration value corresponding to a known pharmacodynamic probability of causing a particular bodily effect, wherein the two-dimensional model includes indicators of at least one of:
- a probability that a subject will be rendered unconscious by at least one drug having a sedative effect;
- a probability that a subject will not exhibit pain from laryngoscopy, incision, or post-operative recovery of surgery by at least one drug having and analgesic effect; and
- a probability that a subject will not exhibit a response to a train-of-four electrical muscle stimulation by at least one drug having a neuromuscular blocking effect.

16. The method recited in claim 15, wherein displaying comprises displaying the two-dimensional model with indicators of probabilities of different levels of effectiveness.

17. The method recited in claim 16, wherein displaying comprises displaying the two-dimensional model with indicators of probabilities that a subject will not exhibit pain from at least two of laryngoscopy, incision, and post-operative recovery of surgery.

18. The system recited in claim 5, wherein the mode of administration the at least one drug comprises a bolus which is represented as a vertical bar.

19. The system recited in claim 18, wherein a height of the vertical bar represents an amount of the at least one drug administered to a subject.

20. The system recited in claim 5, wherein the mode of administration of the at least one drug comprises infusion, which is represented as a horizontal line.

21. The system recited in claim 20, wherein a length of the horizontal line represents a duration of the infusion.

22. The system recited in claim 20, wherein at least one of a thickness and a vertical location of the horizontal line represents an amount of the infusion.

23. The system recited in claim 1, wherein the drug modeler and normalizer is further configured to normalize the individual drug concentrations based on a pharmacodynamic value.

24. The system recited in claim 23, wherein the pharamacodynamic value is the value at which 95% of the population would experience a particular pharmacodynamic effect corresponding to the classification of the corresponding individual drug.

25. The system recited in claim 1, wherein the present and future probability of effectiveness of at least drug introduced into the subject by the drug delivery system is based on a correlation of all of the individual drug concentrations, drug interactions, and the pharmacodynamic effectiveness data previously obtained from a plurality of individuals.

26. The system recited in claim 5, wherein the depicted modes of administration include a bolus injection and an infusion pump.

27. The system recited in claim 5, wherein the present and future probability of effectiveness of at least drug introduced into the subject by the drug delivery system is based on a correlation of all of the individual drug concentrations, drug interactions, and the pharmacodynamic effectiveness data previously obtained from a plurality of individuals.

* * * * *